US012767940B2

(12) United States Patent
Fu et al.

(10) Patent No.: US 12,767,940 B2
(45) Date of Patent: Oct. 20, 2026

(54) AAV-IDUA VECTOR FOR TREATMENT OF MPS I

(71) Applicant: The University of North Carolina at Chapel Hill, Chapel Hill, NC (US)

(72) Inventors: Haiyan Fu, Durham, NC (US); Tierra Bobo, Mebane, NC (US); Hyoukbum Kwon, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 237 days.

(21) Appl. No.: 18/704,645

(22) PCT Filed: Oct. 27, 2022

(86) PCT No.: PCT/US2022/078746

§ 371 (c)(1),
(2) Date: Apr. 25, 2024

(87) PCT Pub. No.: WO2023/076972

PCT Pub. Date: May 4, 2023

(65) Prior Publication Data

US 2026/0132393 A1 May 14, 2026

Related U.S. Application Data

(60) Provisional application No. 63/272,501, filed on Oct. 27, 2021.

(51) Int. Cl.

| | |
|---|---|
| ***C12N 9/24*** | (2006.01) |
| ***A61K 38/47*** | (2006.01) |
| ***A61K 48/00*** | (2006.01) |
| ***A61P 5/00*** | (2006.01) |
| ***C12N 15/86*** | (2006.01) |

(52) U.S. Cl.

CPC ............ *C12N 9/2402* (2013.01); *A61K 38/47* (2013.01); *A61K 48/005* (2013.01); *A61P 5/00* (2018.01); *C12N 15/86* (2013.01); *C12Y 302/01076* (2013.01); *C12N 2750/14143* (2013.01); *C12N 2750/14152* (2013.01); *C12N 2830/50* (2013.01)

(58) Field of Classification Search

None

See application file for complete search history.

(56) References Cited

U.S. PATENT DOCUMENTS

| | | | | |
|---|---|---|---|---|
| 2013/0259924 | A1* | 10/2013 | Bancel ............... | A61K 48/0066 530/358 |
| 2018/0185495 | A1 | 7/2018 | Heller et al. | |
| 2018/0371440 | A1 | 12/2018 | Koeberl et al. | |
| 2019/0048363 | A1 | 2/2019 | Hirsch et al. | |

FOREIGN PATENT DOCUMENTS

| | | | |
|---|---|---|---|
| WO | 2017136500 | A1 | 8/2017 |
| WO | 2018144441 | A1 | 8/2018 |
| WO | 2021081217 | A1 | 4/2021 |
| WO | 2021091217 | A1 | 5/2021 |
| WO | 2021127655 | A1 | 6/2021 |

OTHER PUBLICATIONS

International Search Report and the Written Opinion of the International Searching Authority corresponding to International Patent Application No. PCT/US2022/078746 (14 pages) (mailed Mar. 2, 2023).

"International Preliminary Report on Patentability corresponding to International Patent Application No. PCT/US2022/078746 mailed May 10, 2024".

"Extended European Search Report corresponding to European Application No. 22888480.5 dated Nov. 13, 2025".

Bobo, et al., "Targeting the Root Cause of Mucopolysaccharidosis IIIA with a New scAAV9 Gene Replacement Vector", Molecular Therapy—Methods & Clinical Development 19:474-485 (Dec. 1, 2020).

Buck, et al., "Recombinant Adeno-Associated Viral Vectors (rAAV)-Vector Elements in Ocular Gene Therapy Clinical Trials and Transgene Expression and Bioactivity Assays", Int. J. Mol. Sci. 21:4197 (Jun. 12, 2020) 52 pages.

Hinderer, et al., "Neonatal Systemic AAV Induces Tolerance to CNS Gene Therapy in MPS I Dogs and Nonhuman Primates", Molecular Therapy 23(8):1298-1307 (Aug. 1, 2015).

Mauro, et al., "A critical analysis of codon optimization in human therapeutics", Trends in Molecular Medicine 20 (11):604-613 (Nov. 1, 2014).

Mcfarland, et al., "Evaluation of a novel short polyadenylation signal as an alternative to the SV40 polyadenylation signal", Plasmid 56(1):62-67 (Jul. 1, 2006).

Meadows, et al., "Functional correction of mucopolysaccharidosis I in adult mice by a systemic rAAV9-IDUA gene delivery", Molecular Genetics and Metabolism 117(2):S79 (Feb. 1, 2016) 1 page.

* cited by examiner

*Primary Examiner* — Allison M Fox
*Assistant Examiner* — Gina Pronzati
(74) *Attorney, Agent, or Firm* — Myers Bigel, P.A.

(57) ABSTRACT

This invention relates to viral vectors for delivery of alpha-L-iduronidase to a subject and methods of using the same for treatment and prevention of mucopolysaccharidosis I in a subject, including codon optimized and/or truncated human IDUA nucleotide sequences. Moreover, the invention relates to an AAV vector genome comprising the nucleic acid of the invention, an AAV particle comprising the AAV vector genome, and a pharmaceutical composition comprising the AAV particle.

19 Claims, 12 Drawing Sheets

Specification includes a Sequence Listing.

SEQUENCE LISTING

Sequence total quantity: 8
SEQ ID NO: 1 moltype = DNA length = 1962
FEATURE Location/Qualifiers
source 1..1962
mol_type = other DNA
organism = synthetic construct
SEQUENCE: 1

```
atgcgacctc tgaggccacg ggctgcgttg ttggctcttt tggcgtccct gttggccgca  60
ccgcctgtcg ctccagcaga agcaccccac ctcgtgcatg ttgatgcagc acgagcactg  120
tggccgcttc ggaggttttg gaggtcaacg gggttctgtc ctccattgcc acactctcaa  180
gcggatcagt atgtgttgtc ttgggatcag caactgaacc tggcctatgt cggtgccgta  240
cctcatcgcg gaattaaaca ggttcgaacc cattggctcc ttgagttggt tacgacacgg  300
ggcagcacag gaaggggact ctcttacaat ttcactcact tggacggata ccttgacctc  360
ctgcgagaga atcagctgct tcccggtttc gagttgatgg ggtcagctag cggacacttc  420
actgatttcg aggataagca acaagttttt gagtggaaag acctcgtgtc atcacttgcc  480
cggaggtata tagggcgcta cgggcttgcg cacgtaagta agtggaactt tgagacgtgg  540
aatgagcctg atcaccacga ttttgacaat gtttctatga cgatgcaggg ctttctcaac  600
tactatgacg cgtgttctga aggactgaga gcagccagtc cggcactccg cctgggggc  660
ccaggggact ccttccacac accgcctcgg tccccgcttt cttgggggct gttgcgacac  720
tgtcatgacg gtacgaactt ttttacagga gaagcgggcg tccgcctcga ttatatttct  780
ctgcatcgaa aaggtgcgag gtcctcaatc tctatcctgg agcaggagaa ggtcgtggca  840
caacaaatta gacaactctt tcctaaattt gccgacaccc ctatctataa tgatgaggcc  900
gaccctcttg tgggttggtc acttccgcaa ccctggcggg cggatgtgac atatgcagca  960
atggtagtca aagtgatcgc gcaacatcaa aacttgctcc tggcaaacac gacatccgct  1020
tttccgtatg ccttgctttc aaacgataac gctttccttt cataccaccc gcatcccttt  1080
gcacagcgaa ccctcacagc gcggttccag gtcaataaca cacgacctcc tcacgtccag  1140
ttgttgagaa aacctgtgct tactgccatg ggacttctgg cacttctcga cgaggaacag  1200
ctgtgggcgg aggtatctca agcagggact gtattggata gcaaccacac cgtaggggtc  1260
ctcgcctccg cgcacaggcc acaaggacct gctgatgctt ggcgagctgc agttctgatc  1320
tacgccagtg acgacactag ggcccatccg aacagatcag tcgcggtgac gctgaggctc  1380
cgcggagtgc cccctggtcc cggtctcgtt tacgtcactc gctacctcga caacggactc  1440
tgttctccgg atggcgagtg gagaagactt ggacggcctg ttttcccgac cgcggaacaa  1500
ttccggcgaa tgagggccgc tgaggaccca gtagcggcag cgccaagacc tctccccgct  1560
gggggccgcc tcacccttag acccgctctc aggctcccca gtcttctctt ggtacacgta  1620
tgtgcccgac ctgagaaacc ccctggccag gtcactcgct tgcgagctct tcctttgact  1680
caaggacaac ttgtcctcgt ttggagcgac gagcatgtgg gctctaaatg cctctggact  1740
tatgaaatac agttctcaca agatggcaaa gcatacaccc cggtatctag gaaaccctca  1800
acgttcaacc tgtttgtatt ctcccccgac acgggagccg tgtcaggctc ctaccgagtt  1860
cgggccttgg actactgggc taggcccggc cccttctccg atccagtccc atatttggag  1920
gtccctgttc cgcgcggacc ccccagcccg ggcaatccct ga                    1962
```

SEQ ID NO: 2 moltype = DNA length = 1947
FEATURE Location/Qualifiers
source 1..1947
mol_type = other DNA
organism = synthetic construct
SEQUENCE: 2

```
atgcgtcccc tgcgcccccg cgccgcgctg ctggcgctcc tggcctcgct cctggccgcg  60
cccccggtgg ccccggccga ggccccgcac ctggtgcatg tggacgcggc ccgcgcgctg  120
tggcccctgc ggcgcttctg gaggagcaca ggcttctgcc ccccgctgcc acacagccag  180
gctgaccagt acgtcctcag ctgggaccag cagctcaacc tcgcctatgt gggcgccgtc  240
cctcaccgcg gcatcaagca ggtccggacc cactggctgc tggagcttgt caccaccagg  300
gggtccactg gacggggcct gagctacaac ttcacccacc tggacgggta cctggacctt  360
ctcagggaga accagctcct cccagggttt gagctgatgg gcagcgcctc gggccacttc  420
actgactttg aggacaagca gcaggtgttt gagtggaagg acttggtctc cagcctggcc  480
aggagataca tcggtaggta cggactggcg catgtttcca agtggaactt cgagacgtgg  540
aatgagccag accaccacga ctttgacaac gtctccatga ccatgcaagg cttcctgaac  600
tactacgatg cctgctcgga gggtctgcgc gccgccagcc ccgccctgcg gctgggaggc  660
cccggcgact ccttccacac cccaccgcga tccccgctga gctggggcct cctgcgccac  720
tgccacgacg gtaccaactt cttcactggg gaggcgggcg tgcggctgga ctacatctcc  780
ctccacagga agggtgcgcg cagctccatc tccatcctgg agcaggagaa ggtcgtcgcg  840
cagcagatcc ggcagctctt ccccaagttc gcggacaccc ccatttacaa cgacgaggcg  900
gacccgctgg tgggctggtc cctgccacag ccgtggaggg cggacgtgac ctacgcggcc  960
atggtggtga aggtcatcgc gcagcatcag aacctgctac tggccaacac cacctccgcc  1020
ttcccctacg cgctcctgag caacgacaat gccttcctga gctaccaccc gcaccccttc  1080
gcgcagcgca cgctcaccgc gcgcttccag gtcaacaaca cccgcccgcc gcacgtgcag  1140
ctgttgcgca agccggtgct cacggccatg gggctgctgg cgctgctgga tgaggagcag  1200
ctctgggccg aagtgtcgca ggccgggacc gtcctggaca gcaaccacac ggtgggcgtc  1260
ctggccagcg cccaccgccc ccagggcccg gccgacgcct ggcgcgccgc ggtgctgatc  1320
tacgcgagcg acgacacccg cgcccacccc aaccgcagcg tcgcggtgac cctgcggctg  1380
cgcggggtgc cccccggccc gggcctggtc tacgtcacgc gctacctgga caacgggctc  1440
tgcagccccg acggcgagtg gcggcgcctg ggccggcccg tcttccccac ggcagagcag  1500
ttccggcgca tgcgcgcggc tgaggacccg gtggccgcgg cgccccgccc cttacccgcc  1560
ggcggccgcc tgaccctgcg ccccgcgctg cggctgccgt cgcttttgct ggtgcacgtg  1620
tgtgcgcgcc ccgagaagcc gcccgggcag gtcacgcggc tccgcgccct gcccctgacc  1680
caagggcagc tggttctggt ctggtcggat gaacacgtgg gctccaagtg cctgtggaca  1740
tacgagatcc agttctctca ggacggtaag gcgtacaccc cggtcagcag gaagccatcg  1800
accttcaacc tctttgtgtt cagcccagac acaggtgctg tctctggctc ctaccgagtt  1860
```

```
cgagccctgg actactgggc ccgaccaggc cccttctcgg accctgtgcc gtacctggag  1920
gtccctgtgt ccccgggcaa tccatga                                      1947

SEQ ID NO: 3            moltype = DNA  length = 1947
FEATURE                 Location/Qualifiers
source                  1..1947
                        mol_type = other DNA
                        organism = synthetic construct
SEQUENCE: 3
atgcgacctc tgaggccacg ggctgcgttg ttggctcttt tggcgtccct gttggccgca  60
ccgcctgtcg ctccagcaga agcaccccac ctcgtgcatg ttgatgcagc acgagcactg  120
tggccgcttc ggaggtttg gaggtcaacg gggttctgtc ctccattgcc acactctcaa  180
gcggatcagt atgtgttgtc ttgggatcag caactgaacc tggcctatgt cggtgccgta  240
cctcatcgcg gaattaaaca ggttcgaacc cattggctcc ttgagttggt tacgacacgg  300
ggcagcacag gaaggggact ctcttacaat ttcactcact tggacggata ccttgacctc  360
ctgcgagaga atcagctgct tcccggtttc gagttgatgg ggtcagctag cggacacttc  420
actgatttcg aggataagca acaagttttt gagtggaaag acctcgtgtc atcacttgcc  480
cggaggtata tagggcgcta cgggcttgcg cacgtaagta agtggaactt tgagacgtgg  540
aatgagcctg atcaccacga ttttgacaat gtttctatga cgatgcaggg ctttctcaac  600
tactatgacg cgtgttctga aggactgaga gcagccagtc cggcactccg cctgggggc  660
ccaggggact ccttccacac accgcctcgg tccccgcttt cttgggggct gttgcgacac  720
tgtcatgacg gtacgaactt ttttacagga gaagcgggcg tccgcctcga ttatatttct  780
ctgcatcgaa aggtgcgag gtcctcaatc tctatcctgg agcaggagaa ggtcgtggca  840
caacaaatta gacaactctt tcctaaattt gccgacaccc ctatctataa tgatgaggcc  900
gaccctcttg tgggttggtc acttccgcaa ccctggcggg cggatgtgac atatgcagca  960
atggtagtca aagtgatcgc gcaacatcaa aacttgctcc tggcaaacac gacatccgct  1020
tttccgtatg ccttgctttc aaacgataac gctttccttt cataccaccc gcatcccttt  1080
gcacagcgaa ccctcacagc gcggttccag gtcaataaca cacgacctcc tcacgtccag  1140
ttgttgagaa aacctgtgct tactgccatg ggacttctgg cacttctcga cgaggaacag  1200
ctgtgggcgg aggtatctca agcagggact gtattggata gcaaccacac cgtaggggtc  1260
ctcgcctccg cgcacaggcc acaaggacct gctgatgctt ggcgagctgc agttctgatc  1320
tacgccagtg acgacactag ggcccatccg aacagatcag tcgcggtgac gctgaggctc  1380
cgcggagtgc cccctggtcc cggtctcgtt tacgtcactc gctacctcga caacggactc  1440
tgttctccgg atggcgagtg gagaagactt ggacggcctg ttttcccgac cgcggaacaa  1500
ttccggcgaa tgagggccgc tgaggaccca gtagcggcag cgccaagacc tctccccgct  1560
gggggccgcc tcacccttag acccgctctc aggctcccca gtcttctctt ggtacacgta  1620
tgtgcccgac ctgagaaacc ccctggccag gtcactcgct tgcgagctct tcctttgact  1680
caaggacaac ttgtcctcgt ttggagcgac gagcatgtgg gctctaaatg cctctggact  1740
tatgaaatac agttctcaca agatggcaaa gcatacaccc cggtatctag gaaaccctca  1800
acgttcaacc tgtttgtatt ctcccccgac acgggagccg tgtcaggctc ctaccgagtt  1860
cgggccttgg actactgggc taggcccggc cccttctccg atccagtccc atatttggag  1920
gtccctgtta gcccgggcaa tccctga                                      1947

SEQ ID NO: 4            moltype = DNA  length = 6059
FEATURE                 Location/Qualifiers
source                  1..6059
                        mol_type = other DNA
                        organism = synthetic construct
SEQUENCE: 4
cagcagctgc gcgctcgctc gctcactgag gccgcccggg caaagcccgg gcgtcgggcg  60
acctttggtc gcccggcctc agtgagcgag cgagcgcgca gagagggagt ggggttattt  120
cgtattttat ttagatctga tggtcaggga ttgcccgggc taacagggac ctccaaatat  180
gggactggat cggagaaggg gccgggccta gcccagtagt ccaaggcccg aactcggtag  240
gagcctgaca cggctcccgt gtcgggggag aatacaaaca ggttgaacgt tgagggtttc  300
ctagataccg ggtgtatgc tttgccatct tgtgagaact gtatttcata agtccagagg  360
catttagagc ccacatgctc gtcgctccaa acgaggacaa gttgtccttg agtcaaagga  420
agagctcgca agcgagtgac ctggccaggg ggtttctcag gtcgggcaca tacgtgtacc  480
aagagaagac tggggagcct gagagcgggt ctaagggtga ggcggccccc agcggggaga  540
ggtcttggcg ctgccgctac tgggtcctca gcggccctca ttcgccggaa ttgttccgcg  600
gtcgggaaaa caggccgtcc aagtcttctc cactcgccat ccggagaaca gagtccgttg  660
tcgaggtagc gagtgacgta aacgagaccg ggaccagggg gcactccgcg gagcctcagc  720
gtcaccgcga ctgatctgtt cggatgggcc ctagtgtcgt cactggcgta gatcagaact  780
gcagctcgcc aagcatcagc aggtccttgt ggcctgtgcg cggaggcgag gacccctacg  840
gtgtggttgc tatccaatac agtccctgct tgagatacct ccgcccacag ctgttcctcg  900
tcgagaagtg ccagaagtcc catggcagta agcacaggtt ttctcaacaa ctggacgtga  960
ggaggtcgtg tgttattgac ctggaaccgc gctgtgaggg ttcgctgtgc aaagggatgc  1020
gggtggtatg aaaggaaagc gttatcgttt gaaagcaagg catacggaaa agcggatgtc  1080
gtgtttgcca ggagcaagtt ttgatgttgc gcgatcactt tgactaccat tgctgcatat  1140
gtcacatccg cccgccaggg ttgcggaagt gaccaaccca caagagggtc ggcctcatca  1200
ttatagatag gggtgtcggc aaatttagga aagagttgtc taatttgttg tgccacgacc  1260
ttctcctgct ccaggataga gattgaggac ctcgcacctt ttcgatgcag agaaatataa  1320
tcgaggcgga cgcccgcttc tcctgtaaaa aagttcgtac cgtcatgaca gtgtcgcaac  1380
agcccccaag aaagcgggga ccgaggcggt gtgtggaagg agtcccctgg gccccccagg  1440
cggagtgccg gactggctgc tctcagtcct tcagaacacg cgtcatagta gttgagaaag  1500
ccctgcatcg tcatagaaac attgtcaaaa tcgtggtgat caggctcatt ccacgtctca  1560
aagttccact tacttacgtg cgcaagcccg tagcgcccta tatacctccg ggcaagtgat  1620
gacacgaggt ctttccactc aaaaacttgt tgcttatcct cgaaatcagt gaagtgtccg  1680
ctagctgacc ccatcaactc gaaaccggga agcagctgat tctctcgcag gaggtcaagg  1740
tatccgtcca agtgagtgaa attgtaagag agtccccttc ctgtgctgcc ccgtgtcgta  1800
```

```
accaactcaa ggagccaatg ggttcgaacc tgtttaattc cgcgatgagg tacggcaccg  1860
acataggcca ggttcagttg ctgatcccaa gacaacacat actgatccgc ttgagagtgt  1920
ggcaatggag gacagaaccc cgttgacctc caaaacctcc gaagcggcca cagtgctcgt  1980
gctgcatcaa catgcacgag gtggggtgct tctgctggag cgacaggcgg tgcggccaac  2040
agggacgcca aaagagccaa caacgcagcc cgtggcctca gaggtcgcat ggcgaccggt  2100
cgagcggttc actaaacgag ctctgcttat atagacctcc caccgtacac gcctaccgcc  2160
catttgcgtc aatggggcgg agttgttacg acattttgga aagtcccgtt gattttggtg  2220
ccaaaacaaa ctcccattga cgtcaatggg gtggagactt ggaaatcccc gtgagtccgg  2280
gggtcgttgg gcggtcagcc aggcgggcca tttaccgtaa gttatgtaac gaaagcttcc  2340
taggaacccc tagtgatgga gttggccact ccctctctgc gcgctcgctc gctcactgag  2400
gccgggcgac caaaggtcgc ccgacgcccg ggctttgccc gggcggcctc agtgagcgag  2460
cgagcgcgca gctggcgtaa tagcgaagag gcccgcaccg atcgcccttc ccaacagttg  2520
cgcagcctga atggcgaatg gcgattccgt tgcaatggct ggcggtaata ttgttctgga  2580
tattaccagc aaggccgata gtttgagttc ttctactcag gcaagtgatg ttattactaa  2640
tcaaagaagt attgcgacaa cggttaattt gcgtgatgga cagactcttt tactcggtgg  2700
cctcactgat tataaaaaca cttctcagga ttctggcgta ccgttcctgt ctaaaatccc  2760
tttaatcggc ctcctgttta gctcccgctc tgattctaac gaggaaagca cgttatacgt  2820
gctcgtcaaa gcaaccatag tacgcgccct gtagcggcgc attaagcgcg gcgggtgtgg  2880
tggttacgcg cagcgtgacc gctacacttg ccagcgccct agcgcccgct cctttcgctt  2940
tcttcccttc ctttctcgcc acgttcgccg gctttccccg tcaagctcta aatcgggggc  3000
tccctttagg gttccgattt agtgctttac ggcacctcga ccccaaaaaa cttgattagg  3060
gtgatggttc acgtagtggg ccatcgccct gatagacggt ttttcgccct ttgacgttgg  3120
agtccacgtt ctttaatagt ggactcttgt tccaaactgg aacaacactc aaccctatct  3180
cggtctattc ttttgattta taagggattt tgccgatttc ggcctattgg ttaaaaaatg  3240
agctgattta acaaaaattt aacgcgaatt ttaacaaaat attaacgctt acaatttaaa  3300
tatttgctta tacaatcttc ctgtttttgg ggcttttctg attatcaacc ggggtacata  3360
tgattgacat gctagtttta cgattaccgt tcatcgattc tcttgtttgc tccagactct  3420
caggcaatga cctgatagcc tttgtagaga cctctcaaaa atagctaccc tctccggcat  3480
gaatttatca gctagaacgg ttgaatatca tattgatggt gatttgactg tctccggcct  3540
ttctcacccg tttgaatctt tacctacaca ttactcaggc attgcattta aaatatatga  3600
gggttctaaa aatttttatc cttgcgttga aataaaggct tctcccgcaa aagtattaca  3660
gggtcataat gtttttggta caaccgattt agctttatgc tctgaggctt tattgcttaa  3720
ttttgctaat tctttgcctt gcctgtatga tttattggat gttggaatcg cctgatgcgg  3780
tattttctcc ttacgcatct gtgcggtatt tcacaccgca tatggtgcac tctcagtaca  3840
atctgctctg atgccgcata gttaagccag ccccgacacc cgccaacacc cgctgacgcg  3900
ccctgacggg cttgtctgct cccggcatcc gcttacagac aagctgtgac cgtctccggg  3960
agctgcatgt gtcagaggtt ttcaccgtca tcaccgaaac gcgcgagacg aaagggcctc  4020
gtgatacgcc tatttttata ggttaatgtc atgataataa tggtttctta gacgtcaggt  4080
ggcacttttc ggggaaatgt gcgcggaacc cctatttgtt tatttttcta aatacattca  4140
aatatgtatc cgctcatgag acaataaccc tgataaatgc ttcaataata ttgaaaaagg  4200
aagagtatga gtattcaaca tttccgtgtc gcccttattc ccttttttgc ggcattttgc  4260
cttcctgttt ttgctcaccc agaaacgctg gtgaaagtaa aagatgctga agatcagttg  4320
ggtgcacgag tgggttacat cgaactggat ctcaacagcg gtaagatcct tgagagtttt  4380
cgccccgaag aacgttttcc aatgatgagc acttttaaag ttctgctatg tggcgcggta  4440
ttatcccgta ttgacgccgg gcaagagcaa ctcggtcgcc gcatacacta ttctcagaat  4500
gacttggttg agtactcacc agtcacagaa aagcatctta cggatggcat gacagtaaga  4560
gaattatgca gtgctgccat aaccatgagt gataacactg cggccaactt acttctgaca  4620
acgatcggag gaccgaagga gctaaccgct tttttgcaca acatggggga tcatgtaact  4680
cgccttgatc gttgggaacc ggagctgaat gaagccatac caaacgacga gcgtgacacc  4740
acgatgcctg tagcaatggc aacaacgttg cgcaaactat taactggcga actacttact  4800
ctagcttccc ggcaacaatt aatagactgg atggaggcgg ataaagttgc aggaccactt  4860
ctgcgctcgg cccttccggc tggctggttt attgctgata aatctggagc cggtgagcgt  4920
gggtctcgcg gtatcattgc agcactgggg ccagatggta agccctcccg tatcgtagtt  4980
atctacacga cggggagtca ggcaactatg gatgaacgaa atagacagat cgctgagata  5040
ggtgcctcac tgattaagca ttggtaactg tcagaccaag tttactcata tatactttag  5100
attgatttaa aacttcattt ttaatttaaa aggatctagg tgaagatcct ttttgataat  5160
ctcatgacca aaatccctta acgtgagttt tcgttccact gagcgtcaga ccccgtagaa  5220
aagatcaaag gatcttcttg agatcctttt tttctgcgcg taatctgctg cttgcaaaca  5280
aaaaaaccac cgctaccagc ggtggtttgt ttgccggatc aagagctacc aactcttttt  5340
ccgaaggtaa ctggcttcag cagagcgcag ataccaaata ctgttcttct agtgtagccg  5400
tagttaggcc accacttcaa gaactctgta gcaccgccta catacctcgc tctgctaatc  5460
ctgttaccag tggctgctgc cagtggcgat aagtcgtgtc ttaccgggtt ggactcaaga  5520
cgatagttac cggataaggc gcagcggtcg ggctgaacgg ggggttcgtg cacacagccc  5580
agcttggagc gaacgaccta caccgaactg agatacctac agcgtgagct atgagaaagc  5640
gccacgcttc ccgaagggag aaaggcggac aggtatccgg taagcggcag ggtcggaaca  5700
ggagagcgca cgagggagct tccaggggga aacgcctggt atctttatag tcctgtcggg  5760
tttcgccacc tctgacttga gcgtcgattt ttgtgatgct cgtcaggggg gcggagccta  5820
tggaaaaacg ccagcaacgc ggccttttta cggttcctgg ccttttgctg gccttttgct  5880
cacatgttct ttcctgcgtt atcccctgat tctgtggata accgtattac cgcctttgag  5940
tgagctgata ccgctcgccg cagccgaacg accgagcgca gcgagtcagt gagcgaggaa  6000
gcggaagagc gcccaatacg caaaccgcct ctccccgcgc gttggccgat tcattaatg   6059
```

```
SEQ ID NO: 5           moltype = DNA  length = 6074
FEATURE                Location/Qualifiers
source                 1..6074
                       mol_type = other DNA
                       organism = synthetic construct
SEQUENCE: 5
cagcagctgc gcgctcgctc gctcactgag gccgcccggg caaagcccgg gcgtcgggcg  60
```

-continued

```
acctttggtc gcccggcctc agtgagcgag cgagcgcgca gagagggagt ggggttattt  120
cgtattttat ttagatctga tggtcaggga ttgcccgggc tggggggtcc gcgcggaaca  180
gggacctcca aatatgggac tggatcggag aaggggccgg gcctagccca gtagtccaag  240
gcccgaactc ggtaggagcc tgacacggct cccgtgtcgg gggagaatac aaacaggttg  300
aacgttgagg gtttcctaga taccggggtg tatgctttgc catcttgtga gaactgtatt  360
tcataagtcc agaggcattt agagcccaca tgctcgtcgc tccaaacgag gacaagttgt  420
ccttgagtca aaggaagagc tcgcaagcga gtgacctggc caggggggttt ctcaggtcgg  480
gcacatacgt gtaccaagag aagactgggg agcctgagag cgggtctaag ggtgaggcgg  540
cccccagcgg ggagaggtct tggcgctgcc gctactgggt cctcagcggc cctcattcgc  600
cggaattgtt ccgcggtcgg gaaaacaggc cgtccaagtc ttctccactc gccatccgga  660
gaacagagtc cgttgtcgag gtagcgagtg acgtaaacga gaccgggacc agggggcact  720
ccgcggagcc tcagcgtcac cgcgactgat ctgttcggat gggccctagt gtcgtcactg  780
gcgtagatca gaactgcagc tcgccaagca tcagcaggtc cttgtggcct gtgcgcggag  840
gcgaggaccc ctacggtgtg gttgctatcc aatacagtcc ctgcttgaga tacctccgcc  900
cacagctgtt cctcgtcgag aagtgccaga agtcccatgg cagtaagcac aggttttctc  960
aacaactgga cgtgaggagg tcgtgtgtta ttgacctgga accgcgctgt gagggttcgc  1020
tgtgcaaagg gatgcgggtg gtatgaaagg aaagcgttat cgtttgaaag caaggcatac  1080
ggaaaagcgg atgtcgtgtt tgccaggagc aagttttgat gttgcgcgat cactttgact  1140
accattgctg catatgtcac atccgcccgc cagggttgcg gaagtgacca acccacaaga  1200
gggtcggcct catcattata gataggggtg tcggcaaatt taggaaagag ttgtctaatt  1260
tgttgtgcca cgaccttctc ctgctccagg atagagattg aggacctcgc accttttcga  1320
tgcagagaaa tataatcgag gcggacgccc gcttctcctg taaaaaagtt cgtaccgtca  1380
tgacagtgtc gcaacagccc ccaagaaagc ggggaccgag gcggtgtgtg gaaggagtcc  1440
cctgggcccc ccaggcggag tgccggactg gctgctctca gtccttcaga acacgcgtca  1500
tagtagttga gaaagccctg catcgtcata gaaacattgt caaaatcgtg gtgatcaggc  1560
tcattccacg tctcaaagtt ccacttactt acgtgcgcaa gcccgtagcg ccctatatac  1620
ctccgggcaa gtgatgacac gaggtctttc cactcaaaaa cttgttgctt atcctcgaaa  1680
tcagtgaagt gtccgctagc tgaccccatc aactcgaaac cgggaagcag ctgattctct  1740
cgcaggaggt caaggtatcc gtccaagtga gtgaaattgt aagagagtcc ccttcctgtg  1800
ctgccccgtg tcgtaaccaa ctcaaggagc caatgggttc gaacctgttt aattccgcga  1860
tgaggtacgg caccgacata ggccaggttc agttgctgat cccaagacaa cacatactga  1920
tccgcttgag agtgtggcaa tggaggacag aaccccgttg acctccaaaa cctccgaagc  1980
ggccacagtg ctcgtgctgc atcaacatgc acgaggtggg gtgcttctgc tggagcgaca  2040
ggcggtgcgg ccaacaggga cgccaaaaga gccaacaacg cagcccgtgg cctcagaggt  2100
cgcatggcga ccggtcgagc ggttcactaa acgagctctg cttatataga cctcccaccg  2160
tacacgccta ccgcccattt gcgtcaatgg ggcggagttg ttacgacatt ttggaaagtc  2220
ccgttgattt tggtgccaaa acaaactccc attgacgtca atggggtgga gacttggaaa  2280
tccccgtgag tccgggggtc gttgggcggt cagccaggcg ggccatttac cgtaagttat  2340
gtaacgaaag cttcctagga accccctagtg atggagttgg ccactccctc tctgcgcgct  2400
cgctcgctca ctgaggccgg gcgaccaaag gtcgcccgac gcccgggctt tgcccgggcg  2460
gcctcagtga gcgagcgagc gcgcagctgg cgtaatagcg aagaggcccg caccgatcgc  2520
ccttcccaac agttgcgcag cctgaatggc gaatggcgat tccgttgcaa tggctggcgg  2580
taatattgtt ctggatatta ccagcaaggc cgatagtttg agttcttcta ctcaggcaag  2640
tgatgttatt actaatcaaa gaagtattgc gacaacggtt aatttgcgtg atggacagac  2700
tcttttactc ggtggcctca ctgattataa aaacacttct caggattctg gcgtaccgtt  2760
cctgtctaaa atccctttaa tcggcctcct gtttagctcc cgctctgatt ctaacgagga  2820
aagcacgtta tacgtgctcg tcaaagcaac catagtacgc gccctgtagc ggcgcattaa  2880
gcgcggcggg tgtggtggtt acgcgcagcg tgaccgctac acttgccagc gccctagcgc  2940
ccgctccttt cgctttcttc ccttcctttc tcgccacgtt cgccggcttt ccccgtcaag  3000
ctctaaatcg gggctccct ttagggttcc gatttagtgc tttacggcac ctcgacccca  3060
aaaaacttga ttagggtgat ggttcacgta gtgggccatc gccctgatag acggtttttc  3120
gccctttgac gttggagtcc acgttcttta atagtggact cttgttccaa actggaacaa  3180
cactcaaccc tatctcggtc tattcttttg atttataagg gattttgccg atttcggcct  3240
attggttaaa aaatgagctg atttaacaaa aatttaacgc gaattttaac aaaatattaa  3300
cgcttacaat ttaaatattt gcttatacaa tcttcctgtt tttggggctt ttctgattat  3360
caaccggggt acatatgatt gacatgctag ttttacgatt accgttcatc gattctcttg  3420
tttgctccag actctcaggc aatgacctga tagcctttgt agagacctct caaaaatagc  3480
taccctctcc ggcatgaatt tatcagctag aacggttgaa tatcatattg atggtgattt  3540
gactgtctcc ggcctttctc acccgtttga atctttacct acacattact caggcattgc  3600
atttaaaata tatgagggtt ctaaaaattt ttatccttgc gttgaaataa aggcttctcc  3660
cgcaaaagta ttacagggtc ataatgtttt tggtacaacc gatttagctt tatgctctga  3720
ggctttattg cttaatttg ctaattcttt gccttgcctg tatgatttat tggatgttgg  3780
aatcgcctga tgcggtattt tctccttacg catctgtgcg gtatttcaca ccgcatatgg  3840
tgcactctca gtacaatctg ctctgatgcc gcatagttaa gccagccccg acacccgcca  3900
acacccgctg acgcgccctg acgggcttgt ctgctcccgg catccgctta cagacaagct  3960
gtgaccgtct ccgggagctg catgtgtcag aggttttcac cgtcatcacc gaaacgcgcg  4020
agacgaaagg gcctcgtgat acgcctattt ttataggtta atgtcatgat aataatggtt  4080
tcttagacgt caggtggcac ttttcgggga aatgtgcgcg gaacccctat ttgtttattt  4140
ttctaaatac attcaaatat gtatccgctc atgagacaat aaccctgata aatgcttcaa  4200
taatattgaa aaaggaagag tatgagtatt caacatttcc gtgtcgccct tattcccttt  4260
tttgcggcat tttgccttcc tgtttttgct cacccagaaa cgctggtgaa agtaaaagat  4320
gctgaagatc agttgggtgc acgagtgggt tacatcgaac tggatctcaa cagcggtaag  4380
atccttgaga gttttcgccc cgaagaacgt tttccaatga tgagcacttt taaagttctg  4440
ctatgtggcg cggtattatc ccgtattgac gccgggcaag agcaactcgg tcgccgcata  4500
cactattctc agaatgactt ggttgagtac tcaccagtca cagaaaagca tcttacggat  4560
ggcatgacag taagagaatt atgcagtgct gccataacca tgagtgataa cactgcggcc  4620
aacttacttc tgacaacgat cggaggaccg aaggagctaa ccgctttttt gcacaacatg  4680
gggatcatg taactcgcct tgatcgttgg gaaccggagc tgaatgaagc cataccaaac  4740
gacgagcgtg acaccacgat gcctgtagca atggcaacaa cgttgcgcaa actattaact  4800
```

```
ggcgaactac ttactctagc ttcccggcaa caattaatag actggatgga ggcggataaa  4860
gttgcaggac cacttctgcg ctcggccctt ccggctggct ggtttattgc tgataaatct  4920
ggagccggtg agcgtgggtc tcgcggtatc attgcagcac tggggccaga tggtaagccc  4980
tcccgtatcg tagttatcta cacgacgggg agtcaggcaa ctatggatga acgaaataga  5040
cagatcgctg agataggtgc ctcactgatt aagcattggt aactgtcaga ccaagtttac  5100
tcatatatac tttagattga tttaaaactt catttttaat ttaaaaggat ctaggtgaag  5160
atcctttttg ataatctcat gaccaaaatc ccttaacgtg agttttcgtt ccactgagcg  5220
tcagaccccg tagaaaagat caaaggatct tcttgagatc cttttttttct gcgcgtaatc  5280
tgctgcttgc aaacaaaaaa accaccgcta ccagcggtgg tttgtttgcc ggatcaagag  5340
ctaccaactc tttttccgaa ggtaactggc ttcagcagag cgcagatacc aaatactgtt  5400
cttctagtgt agccgtagtt aggccaccac ttcaagaact ctgtagcacc gcctacatac  5460
ctcgctctgc taatcctgtt accagtggct gctgccagtg gcgataagtc gtgtcttacc  5520
gggttggact caagacgata gttaccggat aaggcgcagc ggtcgggctg aacggggggt  5580
tcgtgcacac agcccagctt ggagcgaacg acctacaccg aactgagata cctacagcgt  5640
gagctatgag aaagcgccac gcttcccgaa gggagaaagg cggacaggta tccggtaagc  5700
ggcagggtcg gaacaggaga gcgcacgagg gagcttccag ggggaaacgc ctggtatctt  5760
tatagtcctg tcgggtttcg ccacctctga cttgagcgtc gatttttgtg atgctcgtca  5820
gggggggcgga gcctatggaa aaacgccagc aacgcggcct ttttacggtt cctggccttt  5880
tgctggcctt ttgctcacat gttctttcct gcgttatccc ctgattctgt ggataaccgt  5940
attaccgcct ttgagtgagc tgataccgct cgccgcagcc gaacgaccga gcgcagcgag  6000
tcagtgagcg aggaagcgga agagcgccca atacgcaaac cgcctctccc cgcgcgttgg  6060
ccgattcatt aatg                                                   6074

SEQ ID NO: 6           moltype = DNA  length = 6074
FEATURE                Location/Qualifiers
source                 1..6074
                       mol_type = other DNA
                       organism = synthetic construct
SEQUENCE: 6
cagcagctgc gcgctcgctc gctcactgag gccgcccggg caaagcccgg gcgtcgggcg  60
acctttggtc gcccggcctc agtgagcgag cgagcgcgca gagagggagt ggggttattt  120
cgtattttat ttagatctga tggtcatgga ttgcccgggg atgggggccc tcttggcaca  180
gggacctcca ggtacggcac agggtccgag aagggggcctg gtcgggccca gtagtccagg  240
gctcgaactc ggtaggagcc agagacagca cctgtgtctg ggctgaacac aaagaggttg  300
aaggtcgatg gcttcctgct gaccggggtg tacgccttac cgtcctgaga gaactggatc  360
tcgtatgtcc acaggcactt ggagcccacg tgttcatccg accagaccag aaccagctgc  420
ccttgggtca ggggcagggc gcggagccgc gtgacctgcc cgggcggctt ctcggggcgc  480
gcacacacgt gcaccagcaa aagcgacggc agccgcagcg cggggcgcag ggtcaggcgg  540
ccgccggcgg gtaaggggcg gggcgccgcg gccaccgggt cctcagccgc gcgcatgcgc  600
cggaactgct ctgccgtggg gaagacgggc cggcccaggc gccgccactc gccgtcgggg  660
ctgcagagcc cgttgtccag gtagcgcgtg acgtagacca ggcccgggcc ggggggcacc  720
ccgcgcagcc gcagggtcac cgcgacgctg cggttggggt gggcgcgggt gtcgtcgctc  780
gcgtagatca gcaccgcggc gcgccaggcg tcggccgggc cctgggggcg gtgggcgctg  840
gccaggacgc ccaccgtgtg gttgctgtcc aggacggtcc cggcctgcga cacttcggcc  900
cagagctgct cctcatccag cagcgccagc agccccatgg ccgtgagcac cggcttgcgc  960
aacagctgca cgtgcggcgg gcgggtgttg ttgacctgga agcgcgcggt gagcgtgcgc  1020
tgcgcgaagg ggtgcgggtg gtagctcagg aaggcattgt cgttgctcag gagcgcgtag  1080
gggaaggcgg aggtggtgtt ggccagtagc aggttctgat gctgcgcgat gaccttcacc  1140
accatggccg cgtaggtcac gtccgccctc cacggctgtg gcagggacca gcccaccagc  1200
gggtccgcct cgtcgttgta aatgggggtg tccgcgaact tggggaagag ctgccggatc  1260
tgctgcgcga cgaccttctc ctgctccagg atggagatgg agctgcgcgc acccttcctg  1320
tggagggaga tgtagtccag ccgcacgccc gcctccccag tgaagaagtt ggtaccgtcg  1380
tggcagtggc gcaggaggcc ccagctcagc ggggatcgcg gtggggtgtg gaaggagtcg  1440
ccggggcctc ccagccgcag ggcggggctg gcggcgcgca gaccctccga gcaggcatcg  1500
tagtagttca ggaagccttg catggtcatg gagacgttgt caaagtcgtg gtggtctggc  1560
tcattccacg tctcgaagtt ccacttggaa acatgcgcca gtccgtacct accgatgtat  1620
ctcctggcca ggctggagac caagtccttc cactcaaaca cctgctgctt gtcctcaaag  1680
tcagtgaagt ggcccgaggc gctgcccatc agctcaaacc ctgggaggag ctggttctcc  1740
ctgagaaggt ccaggtaccc gtccaggtgg gtgaagttgt agctcaggcc ccgtccagtg  1800
gaccccctgg tggtgacaag ctccagcagc cagtgggtcc ggacctgctt gatgccgcgg  1860
tgagggacgg cgcccacata ggcgaggttg agctgctggt cccagctgag gacgtactgg  1920
tcagcctggc tgtgtggcag cggggggcag aagcctgtgc tcctccagaa gcgccgcagg  1980
ggccacagcg cgcgggccgc gtccacatgc accaggtgcg gggcctcggc cggggccacc  2040
gggggcgcgg ccaggagcga ggccaggagc gccagcagcg cggcgcgggg gcgcagggga  2100
cgcatggcga ccggtcgagc ggttcactaa acgagctctg cttatataga cctcccaccg  2160
tacacgccta ccgcccattt gcgtcaatgg ggcggagttg ttacgacatt ttggaaagtc  2220
ccgttgattt tggtgccaaa acaaactccc attgacgtca atggggtgga gacttggaaa  2280
tccccgtgag tccgggggtc gttgggcggt cagccaggcg ggccatttac cgtaagttat  2340
gtaacgaaag cttcctagga accccctagtg atggagttgg ccactccctc tctgcgcgct  2400
cgctcgctca ctgaggccgg gcgaccaaag gtcgcccgac gcccgggctt tgcccgggcg  2460
gcctcagtga gcgagcgagc gcgcagctgg cgtaatagcg aagaggcccg caccgatcgc  2520
ccttcccaac agttgcgcag cctgaatggc gaatggcgat tccgttgcaa tggctggcgg  2580
taatattgtt ctggatatta ccagcaaggc cgatagtttg agttcttcta ctcaggcaag  2640
tgatgttatt actaatcaaa gaagtattgc gacaacggtt aatttgcgtg atggacagac  2700
tcttttactc ggtggcctca ctgattataa aaacacttct caggattctg gcgtaccgtt  2760
cctgtctaaa atccctttaa tcggcctcct gtttagctcc cgctctgatt ctaacgagga  2820
aagcacgtta tacgtgctcg tcaaagcaac catagtacgc gccctgtagc ggcgcattaa  2880
gcgcggcggg tgtggtggtt acgcgcagcg tgaccgctac acttgccagc gccctagcgc  2940
ccgctccttt cgctttcttc ccttcctttc tcgccacgtt cgccggcttt ccccgtcaag  3000
```

```
ctctaaatcg ggggctccct ttagggttcc gatttagtgc tttacggcac ctcgacccca  3060
aaaaacttga ttagggtgat ggttcacgta gtgggccatc gccctgatag acggtttttc  3120
gccctttgac gttggagtcc acgttcttta atagtggact cttgttccaa actggaacaa  3180
cactcaaccc tatctcggtc tattcttttg atttataagg gattttgccg atttcggcct  3240
attggttaaa aaatgagctg atttaacaaa aatttaacgc gaattttaac aaaatattaa  3300
cgcttacaat ttaaatattt gcttatacaa tcttcctgtt tttggggctt ttctgattat  3360
caaccggggt acatatgatt gacatgctag ttttacgatt accgttcatc gattctcttg  3420
tttgctccag actctcaggc aatgacctga tagcctttgt agagacctct caaaaatagc  3480
taccctctcc ggcatgaatt tatcagctag aacggttgaa tatcatattg atggtgattt  3540
gactgtctcc ggcctttctc acccgtttga atctttacct acacattact caggcattgc  3600
atttaaaata tatgagggtt ctaaaaattt ttatccttgc gttgaaataa aggcttctcc  3660
cgcaaaagta ttacagggtc ataatgtttt tggtacaacc gatttagctt tatgctctga  3720
ggctttattg cttaattttg ctaattcttt gccttgcctg tatgatttat tggatgttgg  3780
aatcgcctga tgcggtattt tctccttacg catctgtgcg gtatttcaca ccgcatatgg  3840
tgcactctca gtacaatctg ctctgatgcc gcatagttaa gccagccccg acacccgcca  3900
acacccgctg acgcgccctg acgggcttgt ctgctcccgg catccgctta cagacaagct  3960
gtgaccgtct ccgggagctg catgtgtcag aggttttcac cgtcatcacc gaaacgcgcg  4020
agacgaaagg gcctcgtgat acgcctattt ttataggtta atgtcatgat aataatggtt  4080
tcttagacgt caggtggcac ttttcgggga aatgtgcgcg gaacccctat ttgtttattt  4140
ttctaaatac attcaaatat gtatccgctc atgagacaat aaccctgata aatgcttcaa  4200
taatattgaa aaaggaagag tatgagtatt caacatttcc gtgtcgccct tattcccttt  4260
tttgcggcat tttgccttcc tgtttttgct cacccagaaa cgctggtgaa agtaaaagat  4320
gctgaagatc agttgggtgc acgagtgggt tacatcgaac tggatctcaa cagcggtaag  4380
atccttgaga gttttcgccc cgaagaacgt tttccaatga tgagcacttt taaagttctg  4440
ctatgtggcg cggtattatc ccgtattgac gccgggcaag agcaactcgg tcgccgcata  4500
cactattctc agaatgactt ggttgagtac tcaccagtca cagaaaagca tcttacggat  4560
ggcatgacag taagagaatt atgcagtgct gccataacca tgagtgataa cactgcggcc  4620
aacttacttc tgacaacgat cggaggaccg aaggagctaa ccgctttttt gcacaacatg  4680
ggggatcatg taactcgcct tgatcgttgg gaaccggagc tgaatgaagc cataccaaac  4740
gacgagcgtg acaccacgat gcctgtagca atggcaacaa cgttgcgcaa actattaact  4800
ggcgaactac ttactctagc ttcccggcaa caattaatag actggatgga ggcggataaa  4860
gttgcaggac cacttctgcg ctcggccctt ccggctggct ggtttattgc tgataaatct  4920
ggagccggtg agcgtgggtc tcgcggtatc attgcagcac tggggccaga tggtaagccc  4980
tcccgtatcg tagttatcta cacgacgggg agtcaggcaa ctatggatga acgaaataga  5040
cagatcgctg agataggtgc ctcactgatt aagcattggt aactgtcaga ccaagtttac  5100
tcatatatac tttagattga tttaaaactt catttttaat ttaaaaggat ctaggtgaag  5160
atcctttttg ataatctcat gaccaaaatc ccttaacgtg agttttcgtt ccactgagcg  5220
tcagaccccg tagaaaagat caaaggatct tcttgagatc ctttttttct gcgcgtaatc  5280
tgctgcttgc aaacaaaaaa accaccgcta ccagcggtgg tttgtttgcc ggatcaagag  5340
ctaccaactc tttttccgaa ggtaactggc ttcagcagag cgcagatacc aaatactgtt  5400
cttctagtgt agccgtagtt aggccaccac ttcaagaact ctgtagcacc gcctacatac  5460
ctcgctctgc taatcctgtt accagtggct gctgccagtg gcgataagtc gtgtcttacc  5520
gggttggact caagacgata gttaccggat aaggcgcagc ggtcgggctg aacggggggt  5580
tcgtgcacac agcccagctt ggagcgaacg acctacaccg aactgagata cctacagcgt  5640
gagctatgag aaagcgccac gcttcccgaa gggagaaagg cggacaggta tccggtaagc  5700
ggcagggtcg gaacaggaga gcgcacgagg gagcttccag ggggaaacgc ctggtatctt  5760
tatagtcctg tcgggtttcg ccacctctga cttgagcgtc gatttttgtg atgctcgtca  5820
ggggggcgga gcctatggaa aaacgccagc aacgcggcct ttttacggtt cctggccttt  5880
tgctggcctt ttgctcacat gttctttcct gcgttatccc ctgattctgt ggataaccgt  5940
attaccgcct ttgagtgagc tgataccgct cgccgcagcc gaacgaccga gcgcagcgag  6000
tcagtgagcg aggaagcgga agagcgccca atacgcaaac cgcctctccc cgcgcgttgg  6060
ccgattcatt aatg                                                    6074

SEQ ID NO: 7           moltype = DNA  length = 228
FEATURE                Location/Qualifiers
source                 1..228
                       mol_type = other DNA
                       organism = synthetic construct
SEQUENCE: 7
cggttcacta aacgagctct gcttatatag acctcccacc gtacacgcct accgcccatt  60
tgcgtcaatg gggcggagtt gttacgacat tttggaaagt cccgttgatt ttggtgccaa  120
aacaaactcc cattgacgtc aatggggtgg agacttggaa atccccgtga gtccgggggt  180
cgttgggcgg tcagccaggc gggccattta ccgtaagtta tgtaacga                228

SEQ ID NO: 8           moltype = DNA  length = 16
FEATURE                Location/Qualifiers
source                 1..16
                       mol_type = other DNA
                       organism = synthetic construct
SEQUENCE: 8
aaataaaata cgaaat                                                  16
```

AAV-IDUA VECTOR FOR TREATMENT OF MPS I

STATEMENT OF PRIORITY

This patent application is a 35 U.S.C. § 371 national phase application of PCT Application PCT/US2022/078746, filed Oct. 27, 2022, which claims the benefit of U.S. Provisional Application Ser. No. 63/272,501, filed Oct. 27, 2021, the entire contents of each of which are incorporated by reference herein.

FIELD OF THE INVENTION

This invention relates to viral vectors for delivery of alpha-L-iduronidase to a subject and methods of using the same for treatment of mucopolysaccharidosis I in a subject.

BACKGROUND OF THE INVENTION

Mucopolysaccharidosis I (MPS I) is an autosomal recessive lysosomal storage disorder (LSD) caused by a defect in α-L-iduronidase (IDUA), a lysosomal enzyme essential for the stepwise degradation of biologically important glycosaminoglycans (GAGs), heparan sulfates (HS) and dermatan sulfates (DS). The lack of or reduced IDUA activity results in the accumulation of undegraded or partially degraded HS and DS GAGs in cells in virtually all organs, leading to progressive multisystem disorders. Infants with MPS I appear normal at birth, but deteriorate rapidly between the ages of 4 months and 2 years. While the severity of the disease varies widely among individuals, clinically, there are 2 forms of MPS I, attenuated (Scheie syndrome) and severe (Hurler syndrome). While MPS I presents a spectrum of clinical phenotypes with heterogeneous mutations, all forms of the disease are biochemically indistinguishable, with progressive multisystem disorders. The severe form of MPS I (MPS IH) represents up to 80% of known cases. Children with MPS IH usually die of neurological deterioration and cardiorespiratory failure before 10 years of age, though some with attenuated MPS I (MPS IS) can live to adulthood.

Current MPS I treatments include IDUA enzyme replacement therapy (ERT) (ALDURAZYMER) delivered intravenously (IV) weekly, with demonstrated improvements in somatic symptoms in both severe and attenuated patients. A more promising treatment relies on allogeneic hematopoietic stem cell transplantation (HSCT) which has been used for the past 2-3 decades in MPS I patients. HSCT also benefits the somatic disorders of MPS I, with neurological impacts if performed early (<age 2 years). Otherwise, in general, no treatment is currently available to treat the CNS disorders in MPS IH.

Gene therapy targeting the lack of or reduced IDUA activity with broad delivery is ideal for treating MPS I if delivered to CNS and peripheral tissues, because of the potential for long-term endogenous production of recombinant enzymes and the by-stander effect of IDUA. The endogenous mannose-6-phosphate-mediated lysosomal trafficking pathway allows the secretion of 5-20% IDUA (and other lysosomal hydrolases), leading to a therapeutic by-stander effect/cross-correction on neighboring cells. Only a very low level of enzyme activity (1-10%) is needed to normalize metabolic function. Therefore, near optimal therapeutic benefit can be achieved by gene transfer to a minority of CNS cells as long as the distribution is homogeneous, without the need to treat every cell. Among the gene therapy strategies, recombinant adeno-associated virus (rAAV) is a potential vector for this application because the target tissue is largely post-mitotic. The demonstrated trans-blood brain barrier (BBB)-neurotropic AAV9 has offered a gene delivery tool for treating monogenic neurological diseases, targeting the root cause of these diseases. To date, systemic rAAV9) gene replacement and their associated gene therapy products have been demonstrated to be functionally beneficial with the potential for cure in animal models with neuropathic LSDs.

AAV normally packages as a single-stranded (ss) DNA genome that must be converted to double-stranded (ds) DNA after infection. Constructs less than half of the normal wild-type (WT) AAV genome size can be packaged as dimeric inverted repeat DNA molecules. These self-complementary (sc) genomes fold into ds DNA as soon as they are released from the capsid, bypassing the requirement for DNA synthesis by the host cells to convert the ss vector genome (vg) into active double-stranded DNA and providing faster and more efficient transduction.

There is a need in the art for improved viral vectors for expressing IDUA and treating MPS I.

SUMMARY OF THE INVENTION

This invention is based on the finding that the use of self-complementary AAV vectors for delivery of IDUA to subjects with MPS I is effective to express IDUA, thereby treating MPS I. The invention further relates to a highly effective codon-optimized nucleotide sequence for IDUA. Thus, one aspect of the invention relates to a recombinant nucleic acid comprising a nucleotide sequence encoding human IDUA, wherein the nucleotide sequence has been codon-optimized for expression in human cells.

A further aspect of the invention relates to the use of a 228 bp truncated miniature cytomegalovirus promoter (mCMV), a 16 bp soluble neuropilin-1 (sNRP-1) Poly A signal, and miniaturized hIDUA$^{op}$ cDNA (ΔhIDUA$^{op}$) or non-optimized, miniaturized hIDUA cDNA (ΔhIDUA), which enables the successful packaging of scAAV-ΔhIDUA$^{op}$ or scAAV-ΔhIDUA, respectively.

Another aspect of the invention relates to an AAV vector genome comprising the nucleic acid of the invention, an AAV particle comprising the AAV vector genome, and a pharmaceutical composition comprising the AAV particle.

A further aspect of the invention relates to a method of producing a recombinant AAV particle, the method comprising: providing a cell in vitro with AAV Cap and AAV Rep coding sequences, the AAV vector genome of the invention, and helper functions for generating a productive AAV infection; and allowing assembly of the recombinant AAV particle and encapsidating the AAV vector genome.

An additional aspect of the invention relates to a method of delivering IDUA to a subject, comprising administering to the subject an effective amount of an AAV particle that expresses IDUA, thereby delivering IDUA to the subject.

Another aspect of the invention relates to a method of treating or delaying the onset of MPS I in a subject in need thereof, comprising administering to the subject a therapeutically effective amount of an AAV particle that expresses IDUA, thereby treating or delaying the onset of MPS I—in the subject.

These and other aspects of the invention are set forth in more detail in the description of the invention below.

dITR: AAV2 terminal repeat with deletion of terminal resolution site to force generation of self-complementary dimeric genomes; hIDUA: human Iduronidase cDNA (1,962 bp); $hIDUA^{op}$: codon-optimized hIDUA cDNA (1,962 bp); $\Delta hIDUA^{op}$: miniaturized $hIDUA^{op}$ cDNA (1,947 bp); mCMV: truncated miniaturized human CMV promoter (228 bp); PA: sNRP-1 polyadenylation signals (16 bp).

Figure 2A:
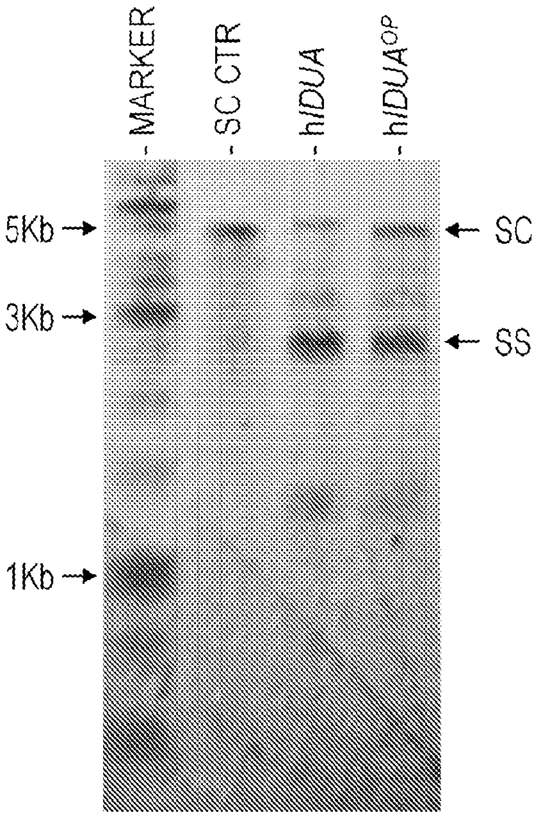
Figure 2B:
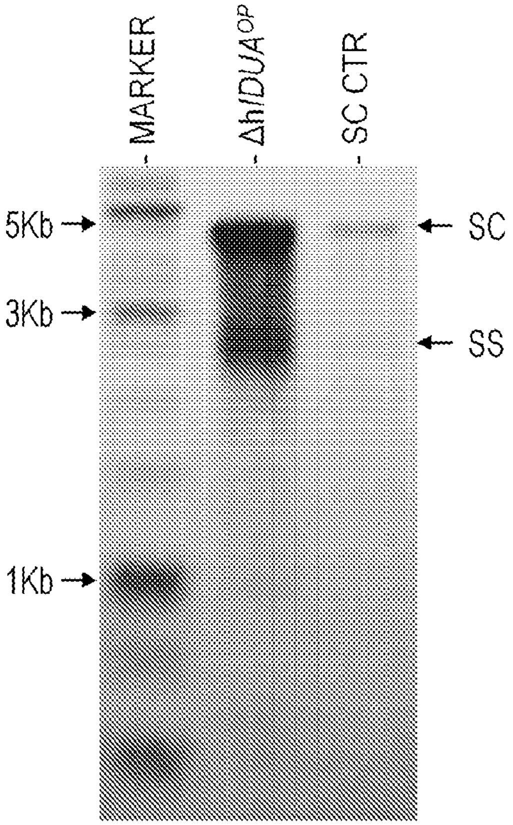

FIGS. 2A-2B are gels showing the generation of scAAV9-mCMV-hIDUA vectors. HEK293 cells were co-transfected by ptrs-mCMV-hIDUA, ptrs-mCMV-$hIDUA^{op}$, or ptrs-mCMV-$\Delta hIDUA^{op}$, and the helper plasmids pHELP and pAAV2/9. Purified AAV9 vector products were analyzed by alkaline denaturing gel electrophoresis. sc Ctr: a known scAAV9 vector; hIDUA: AAV9-mCMV-hIDUA; $hIDUA^{op}$: AAV9-mCMV-$hIDUA^{op}$; $\Delta hIDUA^{op}$: AAV9-mCMV-$\Delta hIDUA^{op}$; sc: scAAV vector genome; ss: single-stranded control vector genome.

Figure 3A:
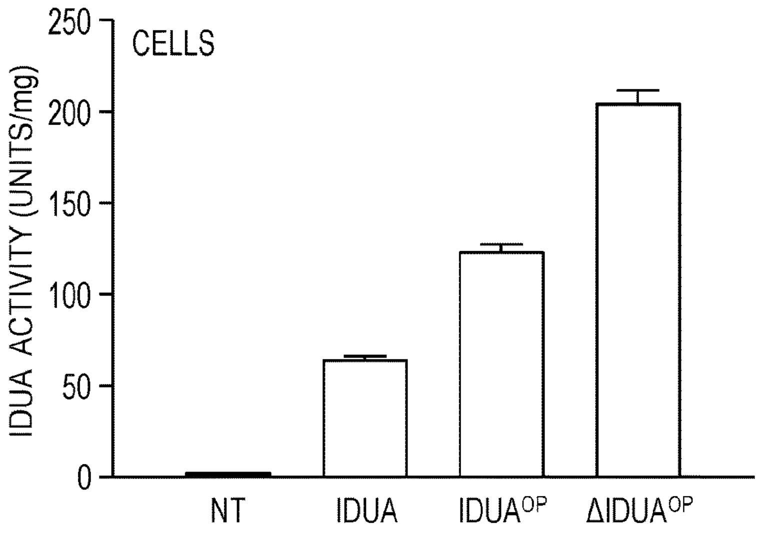
Figure 3B:
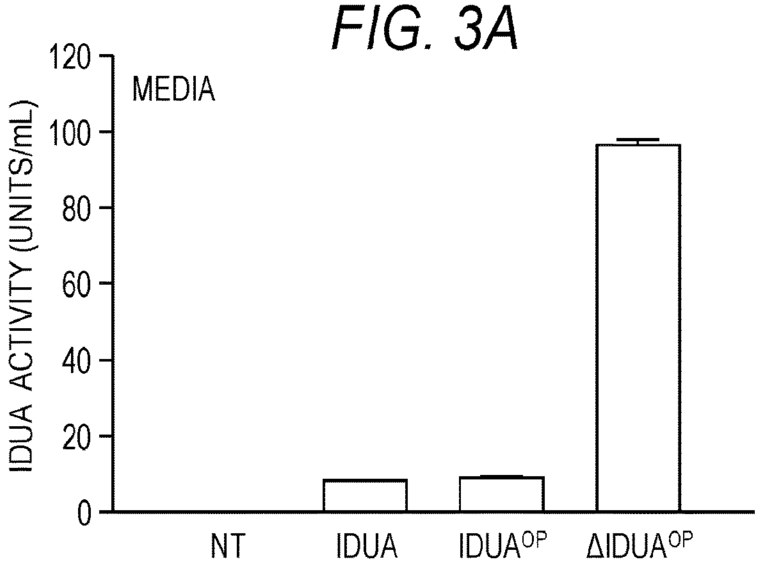
Figure 3C:
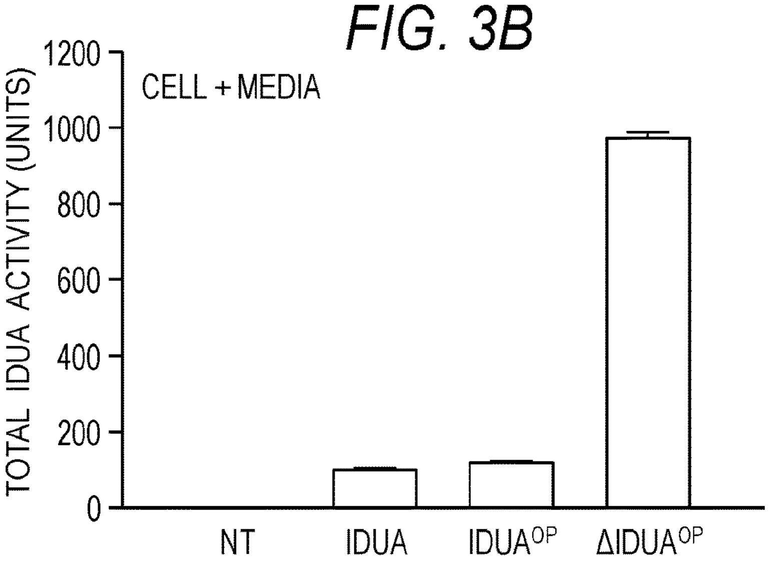

FIGS. 3A-3C show AAV-$hIDUA^{op}$ mediated enhanced expression and secretion of rIDUA in vitro. HeLa cell cultures were transfected in duplicates with 1 μg plasmid of ptrs-mCMV-hIDUA, ptrs-mCMV-$hIDUA^{op}$ or ptrs-mCMV-$\Delta hIDUA^{op}$. Controls were non-transfected HeLa cells. Cell lysates and media were assayed in duplicates for IDS activity at 48 hours post transfection. IDUA activity is expressed as units/mg protein (cells) or units/ml (media), 1 unit=1 nmol 4MU released/hr. NT:non-transfected HeLa cells; IDUA:HeLa cells transfected with ptrs-mCMV-hIDUA; IDUA-op: HeLa cells transfected with ptrs-mCMV-$hIDUA^{op}$; IDUA-op: HeLa cells transfected with ptrs-mCMV-$\Delta hIDUA^{op}$.

Figure 4:
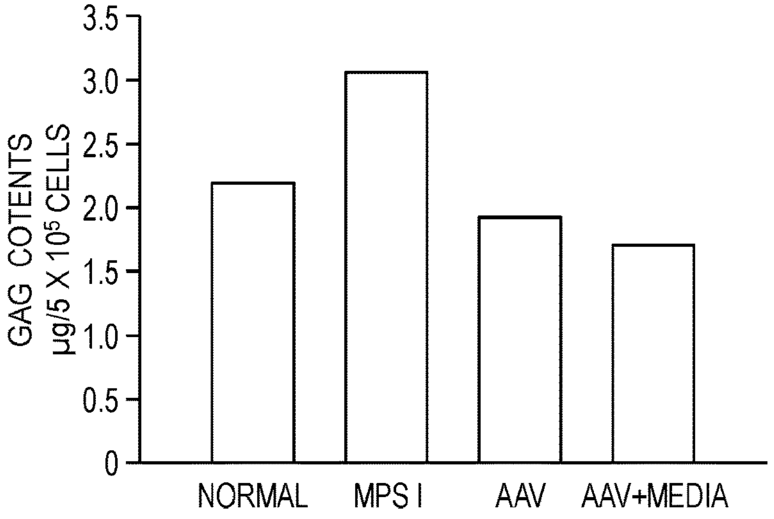

FIG. 4 shows AAV-mediated correction of GAG storage in vitro in human MPS I skin fibroblasts (GM01257). 10 cm plates were transfected in duplicate with ptrs-mCMV-$\Delta hIDUA^{op}$ plasmid (7 μg/plate). 48 hours later, cell lysates were assayed in duplicate for GAG content. Media from the transfected cells were applied to non-treated GM01257 cells, and after 48 hours incubation, cell lysates were assayed in duplicate for GAG content. GAG contents are expressed as μg/$5\times10^5$ cells. Normal: healthy human fibroblasts (GM00969) cells; MPS I: non-treated GM01257 cells; AAV: GM01257 cells transfected with ptrs-mCMV-$\Delta hIDUA^{op}$ plasmid; AAV+media: GM01257 cells incubated with media from ptrs-mCMV-$\Delta hIDUA^{op}$ transfected GM01257 cells.

Figure 5A:
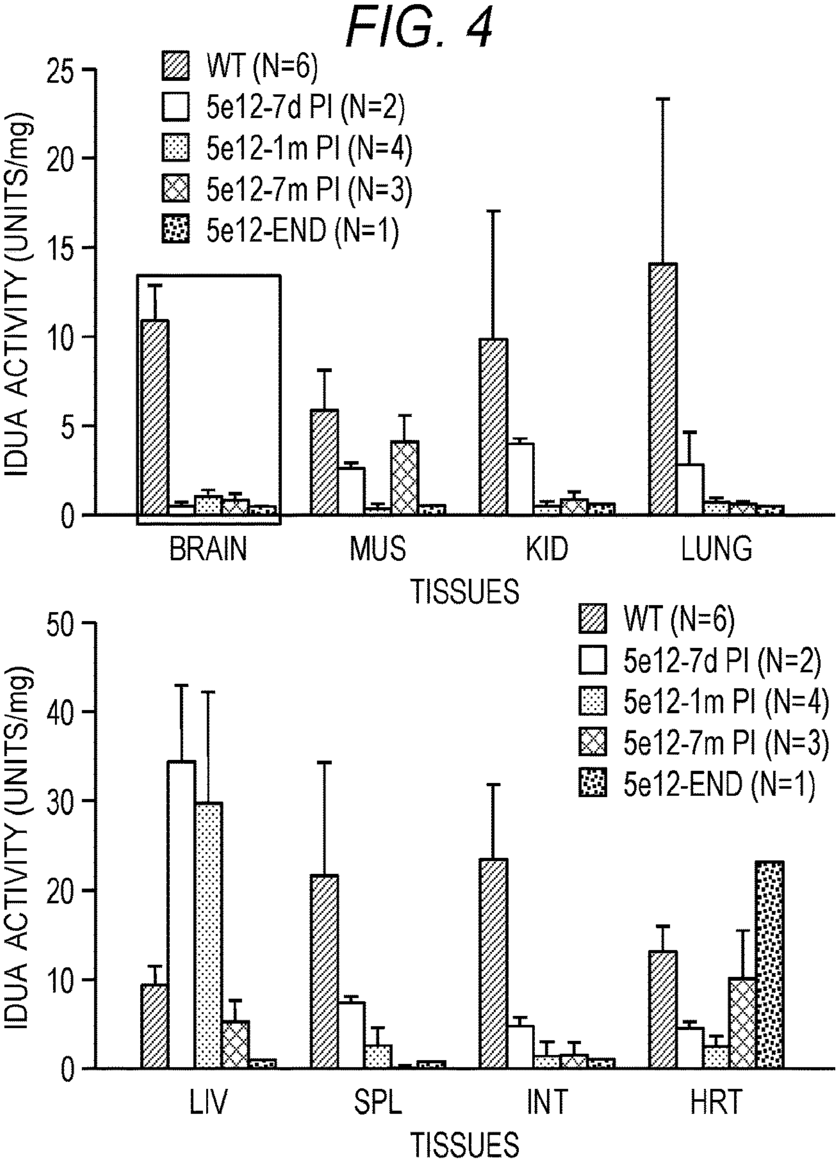
Figure 5B:
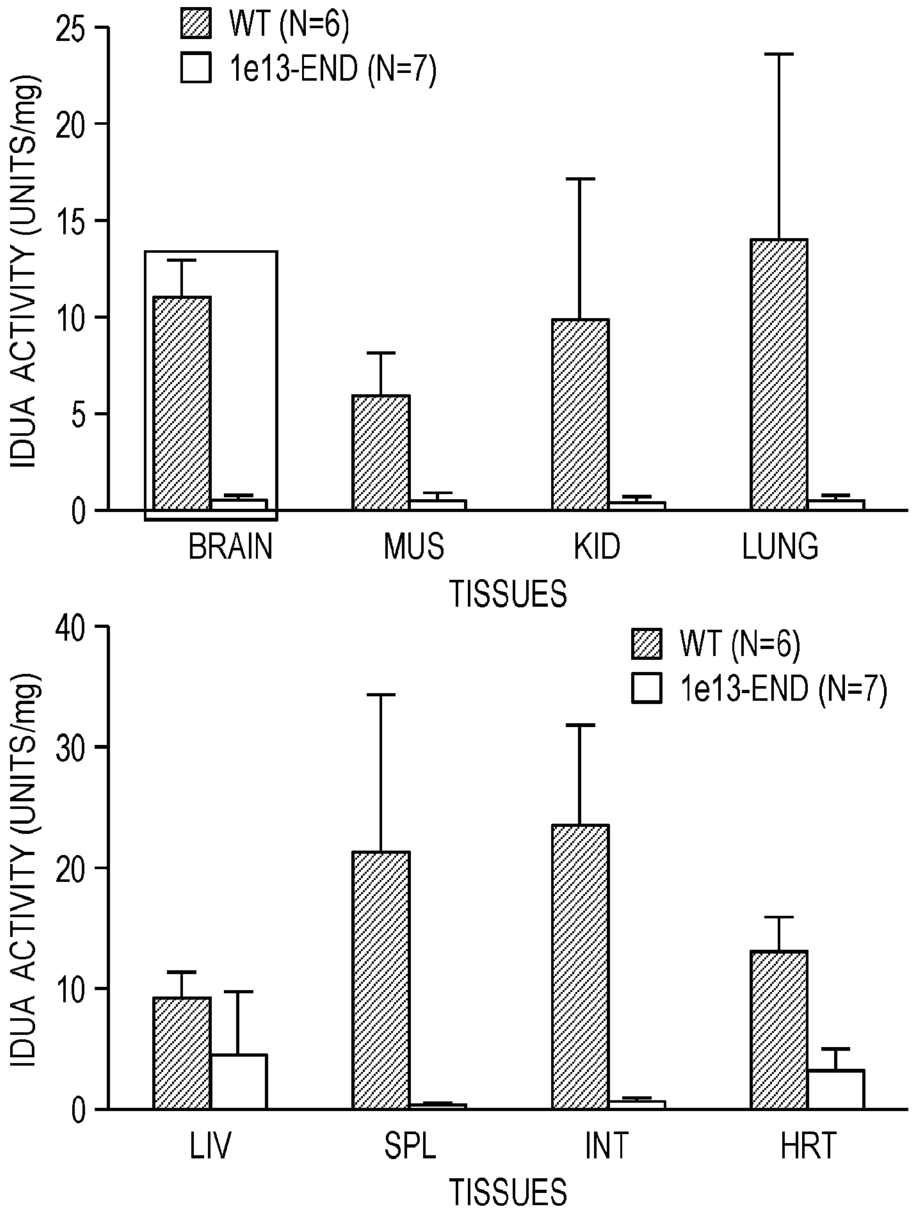
Figure 5C:
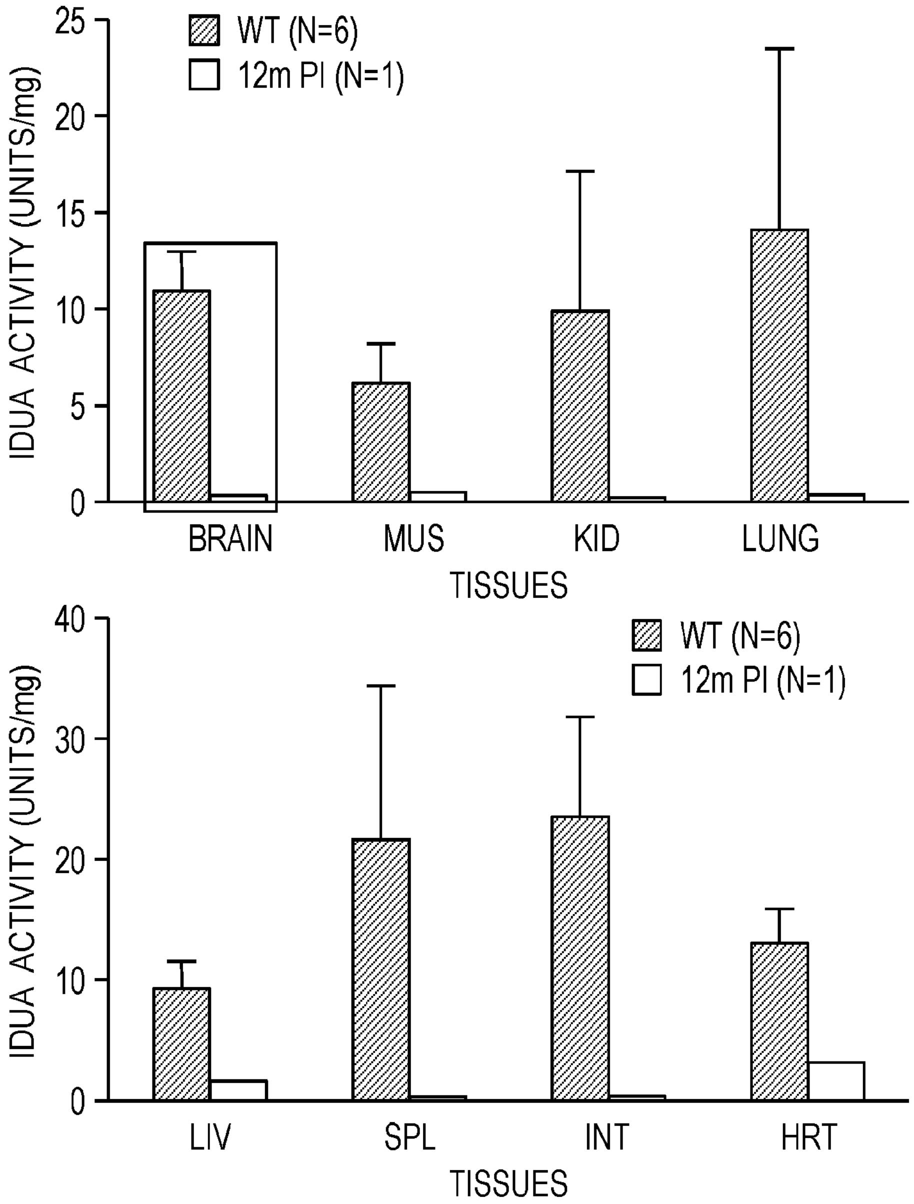

FIGS. 5A-5C show persistent rIDUA expression in the CNS and peripheral tissues after a systemic rAAV9-hIDUA gene delivery. MPS I mice were treated at ages 1 month or 6 months with an IV injection of A) $5\times10^{12}$ vg/kg, B) $1\times10^{13}$ vg/kg, or C) $2\times10^{12}$ vg/kg, rAAV9-mCMV-hIDUA vector. Tissues were assayed for IDUA activity at 7 days, 1 month, 7 months, post vector injection (5A), or humane endpoint (5B), or 12 months post vector injection (5C). IDUA activity is expressed as units/mg protein, 1 unit=nmol 4MU released/hr. *No detectable IDUA activity in tissues of non-treated MPS I mice.

Figure 6A:
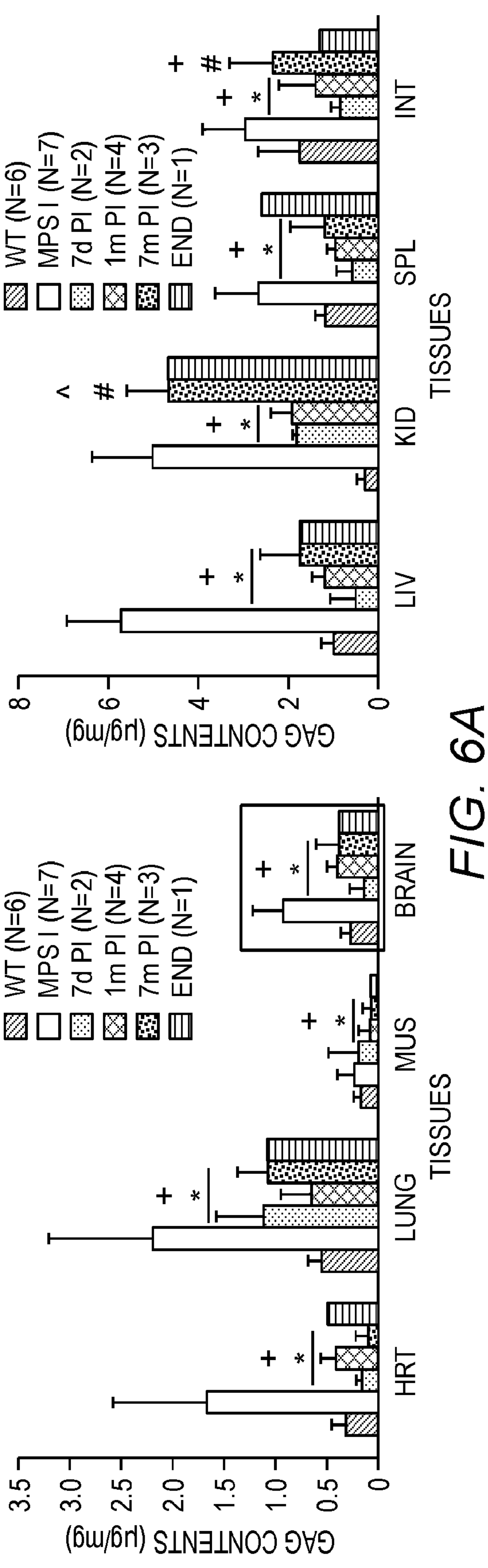
Figure 6B:
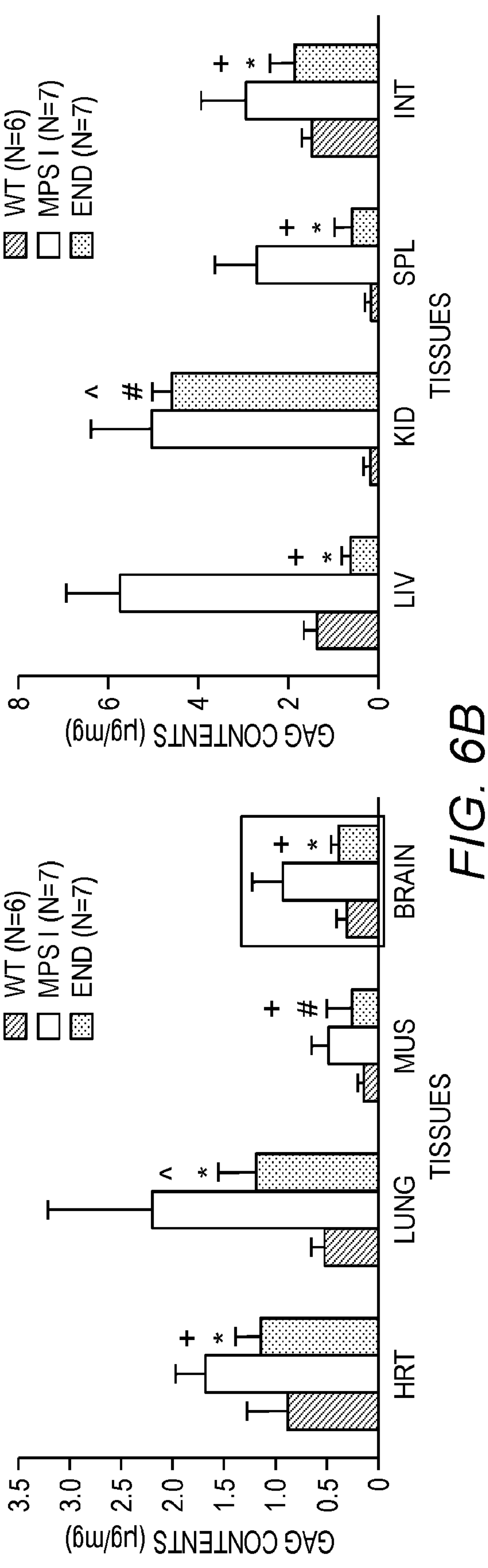

FIGS. 6A-6B show significant reduction of GAG content in the CNS and peripheral tissues in MPS I mice following a systemic rAAV9-hIDUA gene delivery. MPS I mice were treated at age 1 month with an IV injection of rAAV9-mCMV-hIDUA at A) $5\times10^{12}$ vg/kg or B) age 6 months at $1\times10^{13}$ vg/kg. Tissues were assayed for GAG contents at 7 days, 1 month, 7 months post vector injection, or humane endpoint. GAG content is expressed as μg/mg wet tissue. *: $p<0.05$ vs. MPS I; #: $p>0.05$ vs. MPS I; +: $p>0.05$ vs. WT; ^: $p<0.05$ vs. WT.

FIGS. 7A-7D show correction of lysosomal storage and astrocytosis in MPS I mice following a systemic rAAV9-hIDUA vector delivery. MPS I mice were treated with an IV injection of $5\times10^{12}$ vg/kg rAAV9-mCMV-hIDUA at 1 month of age. Tissues were assayed at 7 months post-injection by immunofluorescence for LAMP 1 (red fluorescence) and GFP (green fluorescent protein). MPS I: non-treated MPS I controls; MPS I+AAV9: vector-treated MPS I mouse. A) brain: CTX: cerebral cortex; TH: thalamus: B) retina of eye: RET: retina; ON: outer nuclear layer; IN: inner nuclear layer; C) intestine: INT: small intestine; ME: muscularis externa; Small arrows: neurons of myenteric plexus; Large arrows: lamina propria; D) Other tissues: LIV: liver; LUNG: lung; HRT: heart; CIL: ciliary body of eye; IRIS: iris of eye; Scale bar: 50 μm.

Figure 8A:
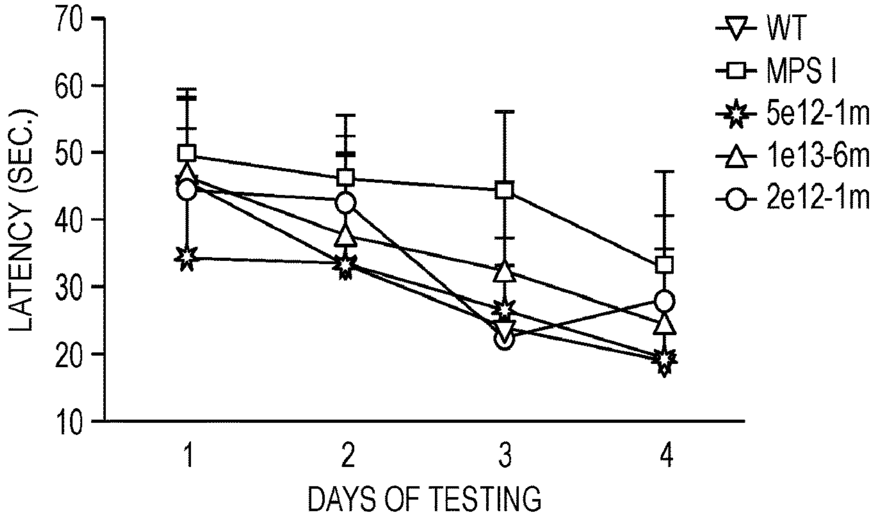
Figure 8B:
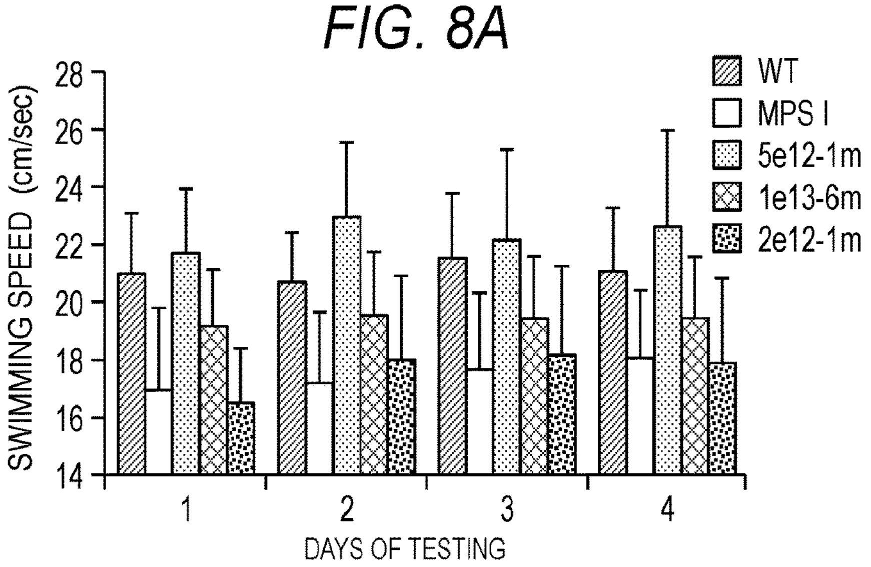
Figure 8C:
Figure 9A:
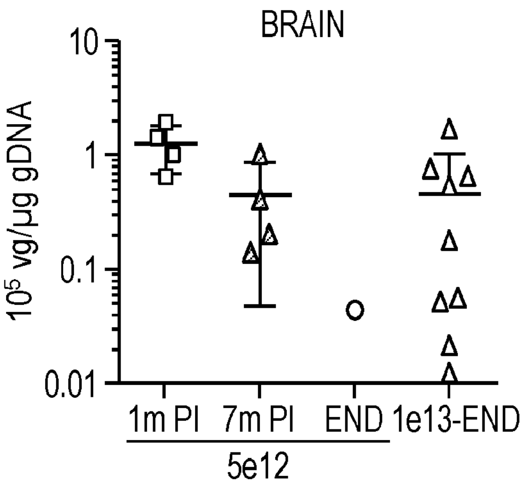
Figure 9B:
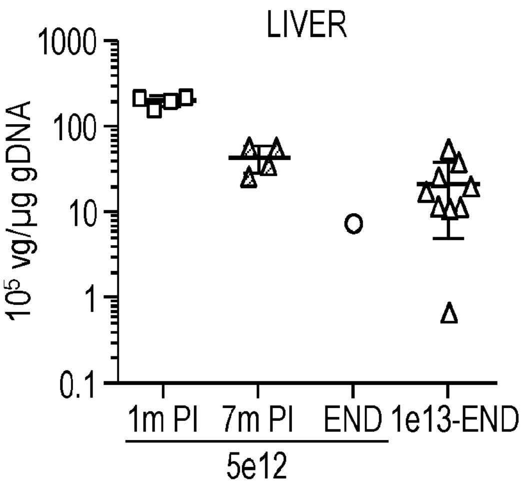
Figure 9C:
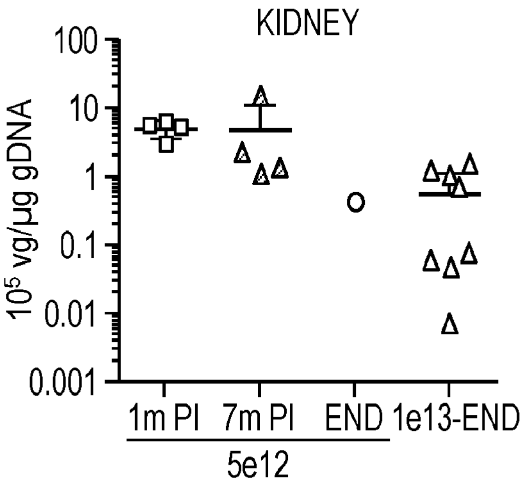
Figure 9D:
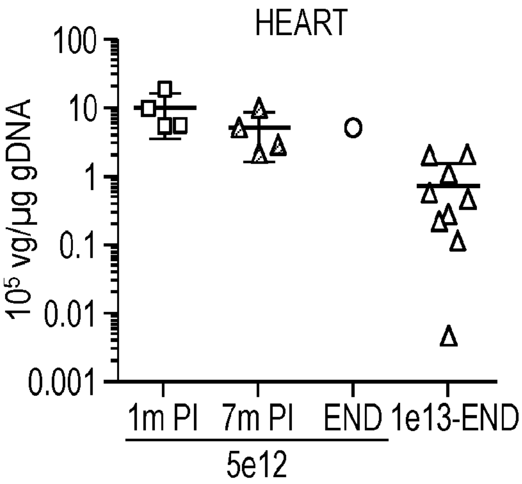
Figure 9E:
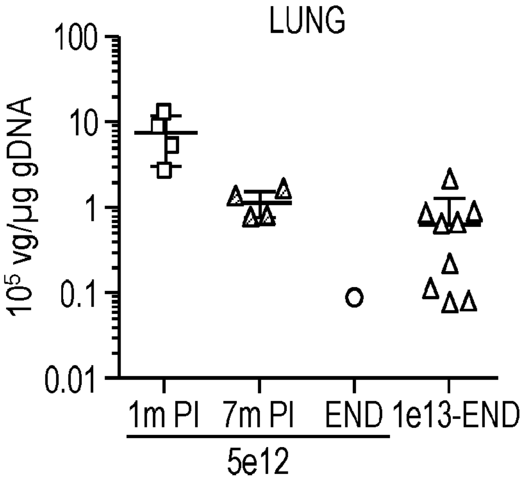
Figure 9F:
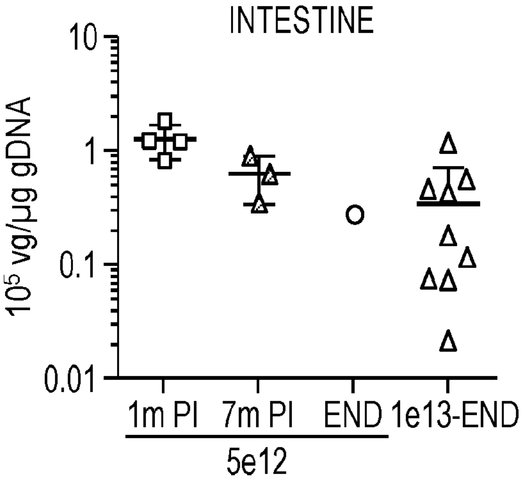
Figure 9G:
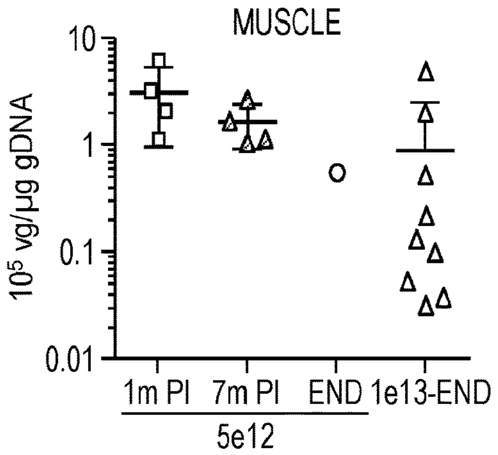
Figure 9H:
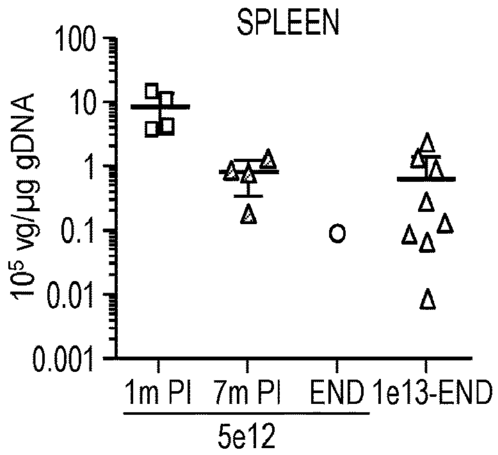

FIGS. 8A-8C show significantly improved behavior performance and extended survival in MPS I mice after a systemic rAAV9-mCMV-hIDUA vector delivery. MPS I mice were treated with an IV injection of rAAV9-mCMV-hIDUA at age 1 month at $2\times10^{12}$ vg/kg or $5\times10^{12}$ vg/kg, or at age 6 months at $1\times10^{13}$ vg/kg. Animals were tested for behavior performance in a hidden task in Morris water maze when they were 7 months old (n=8-29/group), and data were A) latency to find a hidden platform and B) swimming ability. C) Subsets of mice were observed for longevity.

FIGS. 9A-9H show differential biodistribution of systemically delivered rAAV9-mCMV-hIDUA vector in MPS I mice. MPS I mice were treated at age 1 month with an IV injection of $5\times10^{12}$ vg/kg rAAV9-mCMV-hIDUA, or at age 6 months with an IV injection of $1\times10^{13}$ vg/kg rAAV9-mCMV-hIDUA. Tissues were assayed by qPCR for scAAV9-hIDUA vector genome at 1 month post vector injection, 7 months post-injection, or humane endpoint (n=1-9/group). *$<0.001\times10^5$ vg/μg gDNA were detected in tissues from non-treated MPS I mice.

Figure 10A:
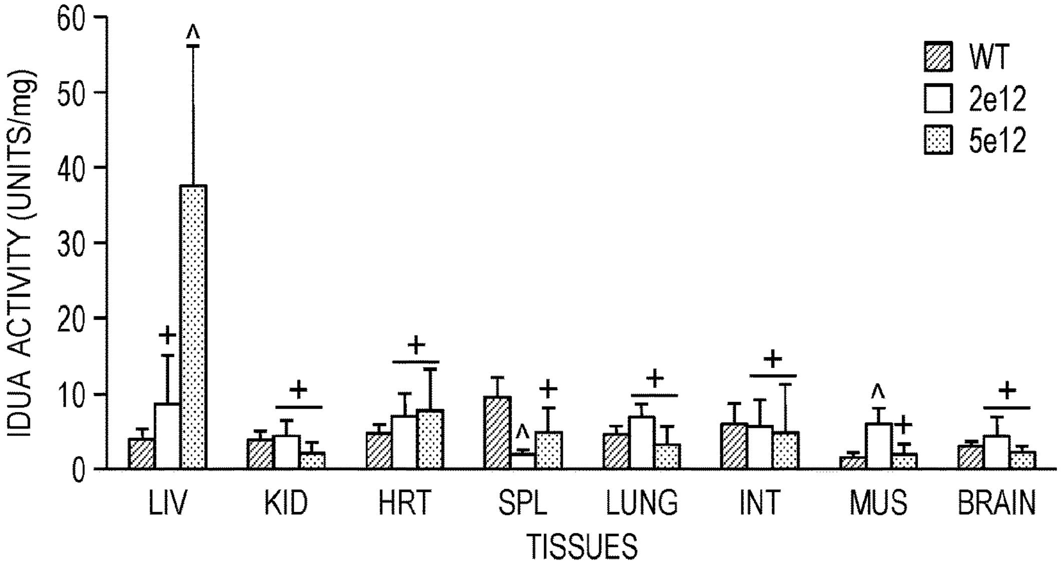
Figure 10B:
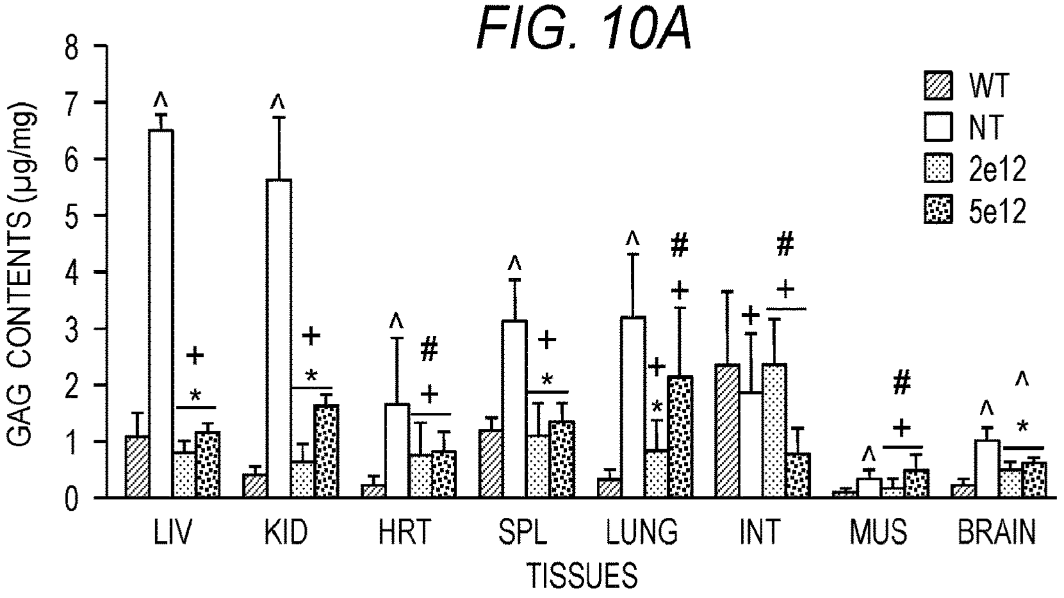

FIGS. 10A-10B show quick restoration of IDUA activity and clearance of GAG contents in the CNS and peripheral organs in MPS I mice following an IV scAAV9-$\Delta hIDUA^{op}$ delivery. MPS I mice were treated at age 1 month with an IV injection of $2\times10^{12}$ vg/kg or $5\times10^{12}$ vg/kg scAAV9-mCMV-$\Delta hIDUA^{op}$ vector. At 1 month pi, tissues (n=4/group) were assayed for IDUA activity (A) and GAG contents (B). IDUA activity is expressed as units/mg protein, 1 unit=nmol 4MU released/hr. GAG content is expressed as μg/mg wet tissue. WT: wildtype mice; NT: non-treated MPS I mice. 2e12/5e12: vector-treated MPS I mice. ^: $p<0.05$ vs. WT; +: $p>0.05$ vs. WT; *: $p<0.05$ vs. NT; #: $p>0.05$ vs. NT.

Figure 11:
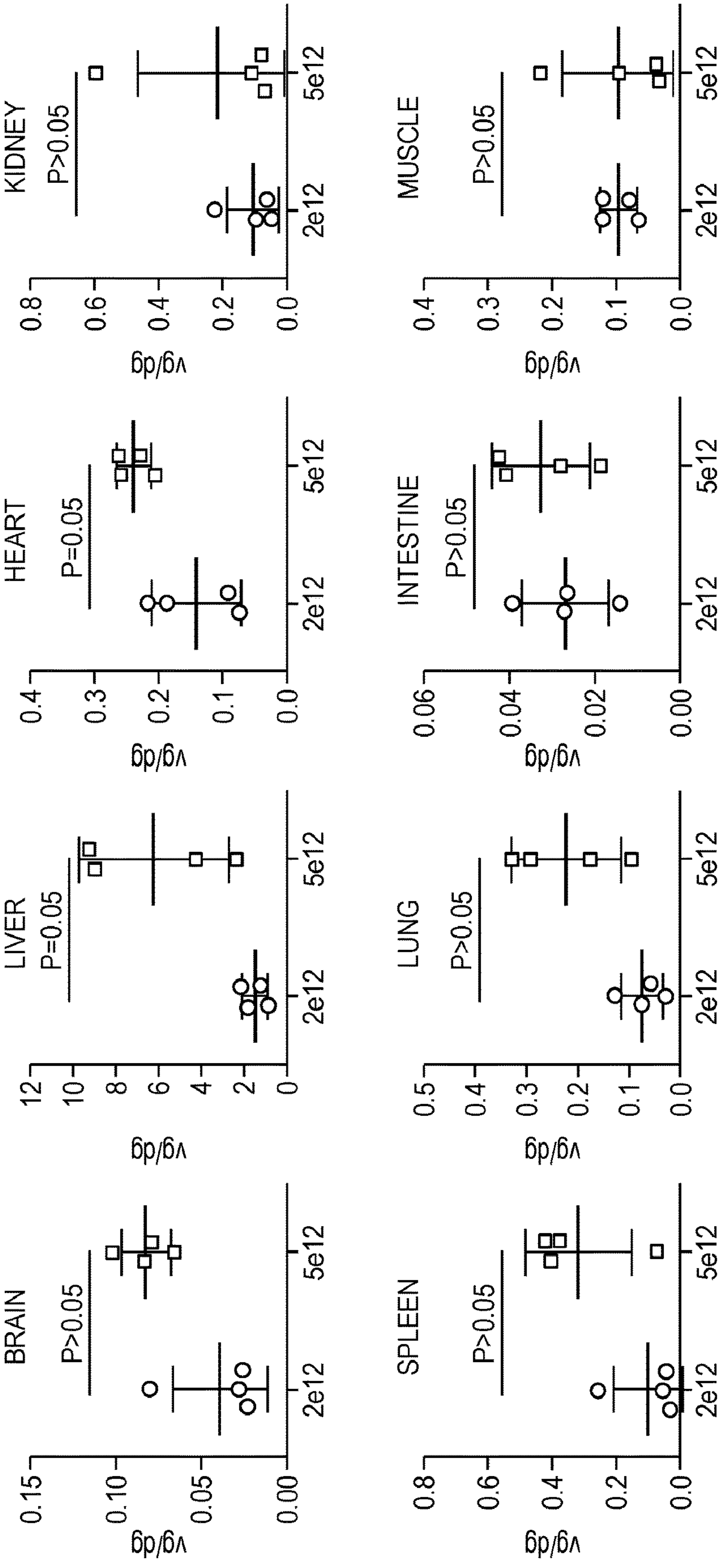

FIG. 11 shows differential biodistribution of systemically delivered scAAV9-mCMV-$\Delta hIDUA^{op}$ vector in MPS I mice. MPS I mice were treated at age 1 month with an IV injection of $2\times10^{12}$ or $5\times10^{12}$ vg/kg scAAV9-mCMV-ΔhIDUA vector. Tissues (n=4/group) were assayed by qPCR for scAAV9-$\Delta hIDUA^{op}$ vector genome at 1 month pi. Data was vg/dg (diploid genome). *<0.002 vg/dg gDNA were detected in tissues from non-treated MPS I mice.

DETAILED DESCRIPTION OF THE INVENTION

The present invention will now be described with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 CFR § 1.822 and established usage. See, e.g., *PatentIn User Manual,* 99-102 (November 1990) (U.S. Patent and Trademark Office).

Except as otherwise indicated, standard methods known to those skilled in the art may be used for the construction of recombinant parvovirus and AAV (rAAV) constructs, packaging vectors expressing the parvovirus Rep and/or Cap sequences, and transiently and stably transfected packaging cells. Such techniques are known to those skilled in the art. See. e.g., SAMBROOK et al., MOLECULAR CLONING: A LABORATORY MANUAL 4th Ed. (Cold Spring Harbor, NY, 2012); AUSUBEL et al., CURRENT PROTOCOLS IN MOLECULAR BIOLOGY (Green Publishing Associates, Inc. and John Wiley & Sons, Inc., New York).

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination. To illustrate further, if, for example, the specification indicates that a particular amino acid can be selected from A, G, I, L and/or V, this language also indicates that the amino acid can be selected from any subset of these amino acid(s) for example A, G, I or L; A, G, I or V; A or G; only L; etc. as if each such subcombination is expressly set forth herein. Moreover, such language also indicates that one or more of the specified amino acids can be disclaimed. For example, in particular embodiments the amino acid is not A, G or I; is not A; is not G or V; etc. as if each such possible disclaimer is expressly set forth herein.

Definitions

The following terms are used in the description herein and the appended claims.

The singular forms "a" and "an" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of 10%, 5%, 1%, 0.5%, or even 0.1% of the specified amount.

Also as used herein, "and/or" refers to and encompasses any and all possible combinations of one or more of the associated listed items, as well as the lack of combinations when interpreted in the alternative ("or").

As used herein, the transitional phrase "consisting essentially of" is to be interpreted as encompassing the recited materials or steps and those that do not materially affect the basic and novel characteristic(s) of the claimed invention (e.g., rAAV replication). Thus, the term "consisting essentially of" as used herein should not be interpreted as equivalent to "comprising."

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence such that the function of the polynucleotide or polypeptide is not materially altered. The total of ten or less additional nucleotides or amino acids includes the total number of additional nucleotides or amino acids on both ends added together. The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in enzymatic activity of at least about 50% or more as compared to the activity of a polypeptide consisting of the recited sequence.

The term "parvovirus" as used herein encompasses the family Parvoviridae, including autonomously-replicating parvoviruses and dependoviruses. The autonomous parvoviruses include members of the genera Parvovirus, Erythrovirus, Densovirus, Iteravirus, and Contravirus. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, snake parvovirus, and B19 virus. Other autonomous parvoviruses are known to those skilled in the art. See, e.g., FIELDS et al., VIROLOGY, volume 2, chapter 69 (4th ed., Lippincott-Raven Publishers).

The genus Dependovirus contains the adeno-associated viruses (AAV), including but not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, avian AAV, bovine AAV, canine AAV, goat AAV, snake AAV, equine AAV, and ovine AAV. See, e.g., FIELDS et al., VIROLOGY, volume 2, chapter 69 (4th ed., Lippincott-Raven Publishers); and Table 1.

TABLE 1

| Complete Genomes | GenBank Accession Number |
|---|---|
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |
| Adeno-associated virus 6 | NC_001862 |
| Avian AAV ATCC VR-865 | AY186198, AY629583, NC_004828 |
| Avian AAV strain DA-1 | NC_006263, AY629583 |
| Bovine AAV | NC_005889, AY388617 |

TABLE 1-continued

| Complete Genomes | GenBank Accession Number |
|---|---|
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B | |
| Hu. 19 | AY530584 |
| Hu. 20 | AY530586 |
| Hu 23 | AY530589 |
| Hu22 | AY530588 |
| Hu24 | AY530590 |
| Hu21 | AY530587 |
| Hu27 | AY530592 |
| Hu28 | AY530593 |
| Hu 29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |

TABLE 1-continued

| Complete Genomes | GenBank Accession Number |
|---|---|
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| Hu14 (AAV9) | AY530579 |
| Hu31 | AY530596 |
| Hu32 | AY530597 |
| Clonal Isolate | |
| AAV5 | Y18065, AF085716 |
| AAV 3 | NC_001729 |
| AAV 3B | NC_001863 |
| AAV4 | NC_001829 |
| Rh34 | AY243001 |
| Rh33 | AY243002 |
| Rh32 | AY243003 |

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, snake AAV, avian AAV, bovine AAV, canine AAV, equine AAV, ovine AAV, goat AAV, shrimp AAV, and any other AAV now known or later discovered. See, e.g., FIELDS et al., VIROLOGY, volume 2, chapter 69 (4th ed., Lippincott-Raven Publishers). A number of relatively new AAV serotypes and clades have been identified (See, e.g., Gao et al., (2004) *J. Virol.* 78:6381; Moris et al., (2004) *Virol.* 33-:375; and Table 1.

The parvovirus vectors, particles, and genomes of the present invention can be from, but are not limited to, AAV. The genomic sequences of various serotypes of AAV and the autonomous parvoviruses, as well as the sequences of the native ITRs, Rep proteins, and capsid subunits are known in the art. Such sequences may be found in the literature or in public databases such as GenBank. See, e.g., GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, AY631966, AX753250, EU285562, NC_001358, NC_001540, AF513851, AF513852 and AY530579; the disclosures of which are incorporated by reference herein for teaching parvovirus and AAV nucleic acid and amino acid sequences. See also, e.g., Bantel-Schaal et al., (1999) *J. Virol.* 73:939; Chiorini et al., (1997) *J. Virol.* 71:6823; Chiorini et al., (1999) *J. Virol.* 73:1309; Gao et al., (2002) *Proc. Nat. Acad. Sci. USA* 99:11854; Moris et al., (2004) *Virol.* 33-:375-383; Mori et al., (2004) *Virol.* 330: 375; Muramatsu et al., (1996) *Virol.* 221:208; Ruffing et al., (1994) *J. Gen. Virol.* 75:3385; Rutledge et al., (1998) *J. Virol.* 72:309; Schmidt et al., (2008) *J. Virol.* 82:8911; Shade et al., (1986) *J. Virol.* 58:921; Srivastava et al., (1983) *J. Virol.* 45:555; Xiao et al., (1999) *J. Virol.* 73:3994; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 1. An early description of the AAV1, AAV2 and AAV3 ITR sequences is provided by Xiao, X., (1996), "Characterization of Adeno-associated virus (AAV) DNA replication and integration," Ph.D. Dissertation, University of Pittsburgh, Pittsburgh, PA (incorporated herein in its entirety).

The term "tropism" as used herein refers to entry of the virus into the cell, optionally and preferably followed by expression (e.g., transcription and, optionally, translation) of sequences carried by the viral genome in the cell, e.g., for a recombinant virus, expression of the heterologous nucleotide sequences(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of AAV, gene expression from the viral genome may be from a stably integrated provirus, from a non-integrated episome, as well as any other form in which the virus may take within the cell.

As used herein, "transduction" of a cell by parvovirus or AAV refers to parvovirus/AAV-mediated transfer of genetic material into the cell. See, e.g., FIELDS et al., VIROLOGY, volume 2, chapter 69 (3d ed., Lippincott-Raven Publishers).

The terms "5' portion" and "3' portion" are relative terms to define a spatial relationship between two or more elements. Thus, for example, a "3' portion" of a polynucleotide indicates a segment of the polynucleotide that is downstream of another segment. The term "3' portion" is not intended to indicate that the segment is necessarily at the 3' end of the polynucleotide, or even that it is necessarily in the 3' half of the polynucleotide, although it may be. Likewise, a "5' portion" of a polynucleotide indicates a segment of the polynucleotide that is upstream of another segment. The term "5' portion" is not intended to indicate that the segment is necessarily at the 5' end of the polynucleotide, or even that it is necessarily in the 5' half of the polynucleotide, although it may be.

As used herein, the terms "protein" and "polypeptide" are used interchangeably and encompass both peptides and proteins, unless indicated otherwise.

As used herein, "nucleic acid," "nucleotide sequence," and "polynucleotide" are used interchangeably and encompass both RNA and DNA, including cDNA, genomic DNA, mRNA, synthetic (e.g., chemically synthesized) DNA or RNA and chimeras of RNA and DNA (including both naturally occurring and non-naturally occurring nucleotides), and can be either single or double stranded DNA sequences. The term polynucleotide, nucleotide sequence, or nucleic acid refers to a chain of nucleotides without regard to length of the chain. The nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

The term "enhance" or "increase" refers to an increase in the specified parameter of at least about 1.25-fold, 1.5-fold, 2-fold, 3-fold, 4-fold, 5-fold, 6-fold, 8-fold, 10-fold, twelve-fold, or even fifteen-fold.

The term "inhibit" or "reduce" or grammatical variations thereof as used herein refers to a decrease or diminishment in the specified level or activity of at least about 15%, 25%, 35%, 40%, 50%, 60%, 75%, 80%, 90%, 95% or more. In particular embodiments, the inhibition or reduction results in little or essentially no detectible activity (at most, an insignificant amount, e.g., less than about 10% or even 5%).

As used herein, "complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A: T) in the case of DNA, or adenine paired with uracil (A: U) in the case of RNA. For example, the sequence "A-G-T" binds to the complementary sequence "T-C-A." It is understood that two polynucleotides may hybridize to each other even if they are not completely complementary to each other, provided that each has at least one region that is substantially complementary to the other.

As used herein, the term "substantially identical" or "corresponding to" means that two nucleic acid sequences have at least 60%, 70%, 80% or 90% sequence identity. In some embodiments, the two nucleic acid sequences can have at least 85%, 90%, 95%, 96%, 97%, 98%, 99% or 100% of sequence identity.

An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence.

The term "sequence identity," as used herein, has the standard meaning in the art. As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, *Adv. Appl. Math.* 2:482 (1981), by the sequence identity alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, WI), the Best Fit sequence program described by Devereux et al., *Nucl. Acid Res.* 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351 (1987); the method is similar to that described by Higgins & Sharp, *CABIOS* 5:151 (1989).

Another example of a useful algorithm is the BLAST algorithm, described in Altschul et al., *J. Mol. Biol.* 215:403 (1990) and Karlin et al., *Proc. Natl. Acad. Sci. USA* 90:5873 (1993). A particularly useful BLAST program is the WU-BLAST-2 program which was obtained from Altschul et al., *Meth. Enzymol.,* 266:460 (1996); blast.wustl/edu/blast/README.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer nucleotides than the polynucleotides specifically disclosed herein, it is understood that in one embodiment, the percentage of sequence identity will be determined based on the number of identical nucleotides in relation to the total number of nucleotides. Thus, for example, sequence identity of sequences shorter than a sequence specifically disclosed herein, will be determined using the number of nucleotides in the shorter sequence, in one embodiment. In percent identity calculations relative weight is not assigned to various manifestations of sequence variation, such as insertions, deletions, substitutions, etc.

The percent of sequence identity can be determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *J Mol. Biol.* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Adv. Appl. Math.,* 2:482-489, 1981, Smith et al., *Nucleic Acids Res.* 11:2205-2220, 1983).

Useful methods for determining sequence identity are also disclosed in Guide to Huge Computers (Martin J. Bishop, ed., Academic Press, San Diego (1994)), and Carillo, H., and Lipton, D., (*Applied Math* 48:1073 (1988)). More particularly, preferred computer programs for determining sequence identity include but are not limited to the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; (Altschul et al., *J. Mol. Biol.* 215:403-410 (1990)); version 2.0 or higher of BLAST programs allows the introduction of gaps (deletions and insertions) into alignments; for peptide sequence BLASTX can be used to determine sequence identity; and, for polynucleotide sequence BLASTN can be used to determine sequence identity.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

An "isolated polynucleotide" is a nucleotide sequence (e.g., DNA or RNA) that is not immediately contiguous with nucleotide sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to a coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant DNA that is part of a hybrid nucleic acid encoding an additional polypeptide or peptide sequence. An isolated polynucleotide that includes a gene is not a fragment of a chromosome that includes such gene, but rather includes the coding region and regulatory regions associated with the gene, but no additional genes naturally found on the chromosome.

The term "isolated" can refer to a nucleic acid, nucleotide sequence or polypeptide that is substantially free of cellular material, viral material, and/or culture medium (when produced by recombinant DNA techniques), or chemical precursors or other chemicals (when chemically synthesized). Moreover, an "isolated fragment" is a fragment of a nucleic acid, nucleotide sequence or polypeptide that is not naturally occurring as a fragment and would not be found in the natural state. "Isolated" does not mean that the preparation is technically pure (homogeneous), but it is sufficiently pure to provide the polypeptide or nucleic acid in a form in which it can be used for the intended purpose.

The term "fragment," as applied to a polypeptide, will be understood to mean an amino acid sequence of reduced length relative to a reference polypeptide or amino acid sequence and comprising, consisting essentially of, and/or consisting of an amino acid sequence of contiguous amino acids identical or almost identical (e.g., 90%, 92%, 95%, 98%, 99% identical) to the reference polypeptide or amino acid sequence. Such a polypeptide fragment according to the invention may be, where appropriate, included in a larger polypeptide of which it is a constituent. In some embodiments, such fragments can comprise, consist essentially of, and/or consist of peptides having a length of at least about 4, 6, 8, 10, 12, 15, 20, 25, 30, 35, 40, 45, 50, 75, 100, 150, 200, or more consecutive amino acids of a polypeptide or amino acid sequence according to the invention.

As used herein, a "functional" polypeptide or "functional fragment" is one that substantially retains at least one biological activity normally associated with that peptide (e.g., degradation of glycosaminoglycans, heparan sulfates, and/or dermatan sulfates). In particular embodiments, the "functional" polypeptide or "functional fragment" substantially retains all of the activities possessed by the unmodified polypeptide. By "substantially retains" biological activity, it is meant that the peptide retains at least about 50%, 60%, 75%, 85%, 90%, 95%, 97%, 98%, 99%, or more, of the biological activity of the native polypeptide (and can even have a higher level of activity than the native peptide). A "non-functional" peptide is one that exhibits little or essentially no detectable biological activity normally associated with the peptide (e.g., at most, only an insignificant amount, e.g., less than about 10% or even 5%). Biological activities such as degradation of glycosaminoglycans, heparan sulfates, and/or dermatan sulfates can be measured using assays that are well known in the art and as described herein.

An "isolated cell" refers to a cell that is separated from other components with which it is normally associated in its natural state. For example, an isolated cell can be a cell in culture medium and/or a cell in a pharmaceutically acceptable carrier of this invention. Thus, an isolated cell can be delivered to and/or introduced into a subject. In some embodiments, an isolated cell can be a cell that is removed from a subject and manipulated as described herein ex vivo and then returned to the subject.

As used herein, the term "modified," as applied to a polynucleotide or polypeptide sequence, refers to a sequence that differs from a wild-type sequence due to one or more deletions, additions, substitutions, or any combination thereof.

As used herein, by "isolate" or "purify" (or grammatical equivalents) a virus vector, it is meant that the virus vector is at least partially separated from at least some of the other components in the starting material.

A "therapeutically effective" amount as used herein is an amount that provides some improvement or benefit to the subject. Alternatively stated, a "therapeutically effective" amount is an amount that will provide some alleviation, mitigation, or decrease in at least one clinical symptom in the subject (e.g., in the case of MPS I, reduction in symptoms related to heart disease, skeletal problems, and central nervous system complications, prevention of respiratory tract infections, prevention of corneal clouding, or increase in survival time). Those skilled in the art will appreciate that the therapeutic effects need not be complete or curative, as long as some benefit is provided to the subject.

By the terms "treat," "treating," or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing," and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom (s) in the subject and/or the severity of onset is less than what would occur in the absence of the present invention.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

By the term "express" or "expression" of a polynucleotide coding sequence, it is meant that the sequence is transcribed, and optionally, translated. Typically, according to the present invention, expression of a coding sequence of the invention will result in production of the polypeptide of the invention. The entire expressed polypeptide or fragment can also function in intact cells without purification.

As used herein, the term "gene" refers to a nucleic acid molecule capable of being used to produce mRNA, antisense RNA, miRNA, and the like. Genes may or may not be capable of being used to produce a functional protein. Genes can include both coding and non-coding regions (e.g., introns, regulatory elements, promoters, enhancers, termination sequences and 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within a virion. Alternatively, in some contexts, the term "vector" may be used to refer to the vector genome/vDNA alone or a plasmid.

The virus vectors of the invention can further be duplexed parvovirus particles as described in international patent publication WO 01/92551 (the disclosure of which is incorporated herein by reference in its entirety). Thus, in some embodiments, double stranded (duplex) genomes can be packaged.

A "rAAV vector genome" or "rAAV genome" is an AAV genome (i.e., vDNA) that comprises one or more heterologous nucleic acid sequences. rAAV vectors generally require only the 145 base ITR in cis to generate virus. All other viral sequences are dispensable and may be supplied in trans (Muzyczka (1992) *Curr. Topics Microbiol. Immunol.* 158: 97). Typically, the rAAV vector genome will only retain the one or more ITR sequence so as to maximize the size of the transgene that can be efficiently packaged by the vector. The structural and non-structural protein coding sequences may be provided in trans (e.g., from a vector, such as a plasmid, or by stably integrating the sequences into a packaging cell). In embodiments of the invention the rAAV vector genome comprises at least one ITR sequence (e.g., AAV ITR sequence), optionally two ITRs (e.g., two AAV ITRs), which typically will be at the 5' and 3' ends of the vector genome and flank the heterologous nucleic acid, but need not be contiguous thereto. The ITRs can be the same or different from each other.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The ITR can be an AAV ITR or a non-AAV ITR. For example, a non-AAV ITR sequence such as those of other parvoviruses (e.g., canine parvovirus, bovine parvovirus, mouse parvovirus, porcine parvovirus, human parvovirus B-19) or the SV40 hairpin that serves as the origin of SV40 replication can be used as an ITR, which can further be modified by truncation, substitution, deletion, insertion and/or addition. Further, the ITR can be partially or completely synthetic, such as the "double-D sequence" as described in U.S. Pat. No. 5,478,745 to Samulski et al.

Parvovirus genomes have palindromic sequences at both their 5' and 3' ends. The palindromic nature of the sequences leads to the formation of a hairpin structure that is stabilized by the formation of hydrogen bonds between the complementary base pairs. This hairpin structure is believed to adopt a "Y" or a "T" shape. See, e.g., FIELDS et al., VIROLOGY, volume 2, chapters 69 & 70 (4th ed., Lippincott-Raven Publishers).

An "AAV inverted terminal repeat" or "AAV ITR" may be from any AAV, including but not limited to serotypes 1, 2, 3a, 3b, 4, 5, 6, 7, 8, 9, 10, 11, or 13, snake AAV, avian AAV, bovine AAV, canine AAV, equine AAV, ovine AAV, goat AAV, shrimp AAV, or any other AAV now known or later discovered (see, e.g., Table 1). An AAV ITR need not have the native terminal repeat sequence (e.g., a native AAV ITR sequence may be altered by insertion, deletion, truncation and/or missense mutations), as long as the terminal repeat mediates the desired functions, e.g., replication, virus packaging, persistence, and/or provirus rescue, and the like.

The virus vectors of the invention can further be "targeted" virus vectors (e.g., having a directed tropism) and/or a "hybrid" parvovirus (i.e., in which the viral ITRs and viral capsid are from different parvoviruses) as described in international patent publication WO 00/28004 and Chao et al., (2000) *Mol. Therapy* 2:619.

Further, the viral capsid or genomic elements can contain other modifications, including insertions, deletions and/or substitutions.

The term "template" or "substrate" is used herein to refer to a polynucleotide sequence that may be replicated to produce the parvovirus viral DNA. For the purpose of vector production, the template will typically be embedded within a larger nucleotide sequence or construct, including but not limited to a plasmid, naked DNA vector, bacterial artificial chromosome (BAC), yeast artificial chromosome (YAC) or a viral vector (e.g., adenovirus, herpesvirus, Epstein-Barr Virus, AAV, baculoviral, retroviral vectors, and the like). Alternatively, the template may be stably incorporated into the chromosome of a packaging cell.

As used herein, parvovirus or AAV "Rep coding sequences" indicate the nucleic acid sequences that encode the parvoviral or AAV non-structural proteins that mediate viral replication and the production of new virus particles. The parvovirus and AAV replication genes and proteins have been described in, e.g., FIELDS et al., VIROLOGY, volume 2, chapters 69 & 70 (4th ed., Lippincott-Raven Publishers).

The "Rep coding sequences" need not encode all of the parvoviral or AAV Rep proteins. For example, with respect to AAV, the Rep coding sequences do not need to encode all four AAV Rep proteins (Rep78, Rep 68, Rep52 and Rep40), in fact, it is believed that AAV5 only expresses the spliced Rep68 and Rep40 proteins. In representative embodiments, the Rep coding sequences encode at least those replication proteins that are necessary for viral genome replication and packaging into new virions. The Rep coding sequences will generally encode at least one large Rep protein (i.e., Rep78/68) and one small Rep protein (i.e., Rep52/40). In particular embodiments, the Rep coding sequences encode the AAV Rep78 protein and the AAV Rep52 and/or Rep40 proteins. In other embodiments, the Rep coding sequences encode the Rep68 and the Rep52 and/or Rep40 proteins. In a still further embodiment, the Rep coding sequences encode the Rep68 and Rep52 proteins, Rep68 and Rep40 proteins, Rep78 and Rep52 proteins, or Rep78 and Rep40 proteins.

As used herein, the term "large Rep protein" refers to Rep68 and/or Rep78. Large Rep proteins of the claimed invention may be either wild-type or synthetic. A wild-type large Rep protein may be from any parvovirus or AAV, including but not limited to serotypes 1, 2, 3a, 3b, 4, 5, 6, 7, 8, 9, 10, 11, or 13, or any other AAV now known or later discovered (see, e.g., Table 1). A synthetic large Rep protein may be altered by insertion, deletion, truncation and/or missense mutations.

Those skilled in the art will further appreciate that it is not necessary that the replication proteins be encoded by the same polynucleotide. For example, for MVM, the NS-1 and NS-2 proteins (which are splice variants) may be expressed independently of one another. Likewise, for AAV, the p19 promoter may be inactivated and the large Rep protein(s) expressed from one polynucleotide and the small Rep protein(s) expressed from a different polynucleotide. Typically, however, it will be more convenient to express the replication proteins from a single construct. In some systems, the viral promoters (e.g., AAV p19 promoter) may not be recognized by the cell, and it is therefore necessary to express the large and small Rep proteins from separate expression cassettes. In other instances, it may be desirable to express the large Rep and small Rep proteins separately, i.e., under the control of separate transcriptional and/or translational control elements. For example, it may be desirable to control expression of the large Rep proteins, so as to decrease the ratio of large to small Rep proteins. In the case of insect cells, it may be advantageous to down-regulate expression of the large Rep proteins (e.g., Rep78/68) to avoid toxicity to the cells (see, e.g., Urabe et al., (2002) *Human Gene Therapy* 13:1935).

As used herein, the parvovirus or AAV "cap coding sequences" encode the structural proteins that form a functional parvovirus or AAV capsid (i.e., can package DNA and infect target cells). Typically, the cap coding sequences will encode all of the parvovirus or AAV capsid subunits, but less than all of the capsid subunits may be encoded as long as a functional capsid is produced. Typically, but not necessarily, the cap coding sequences will be present on a single nucleic acid molecule.

The capsid structure of autonomous parvoviruses and AAV are described in more detail in BERNARD N. FIELDS et al., VIROLOGY, volume 2, chapters 69 & 70 (4th ed., Lippincott-Raven Publishers).

Parvovirus Vectors Expressing IDUA

To address the unmet needs for optimal therapeutic potential, the inventors have developed novel self-complementary (sc) AAV9 gene therapy products expressing human IDUA gene (hIDUA) for the treatment of MPS I. To accommodate the limited packaging capacity of scAAV vectors, the disclosed product was constructed using a 228 bp truncated miniature CMV promoter (mCMV), a 16 bp soluble neuropilin-1 (sNRP-1) Poly A signal, and miniaturized hIDUA$^{op}$ cDNA (ΔhIDUA$^{op}$), which enabled the successful packaging of scAAV-ΔhIDUA$^{op}$ Miniaturized hIDUA$^{op}$ (ΔhIDUA$^{op}$) was constructed by deleting 15 bp of non-coding sequence from near the 3'-end. These changes in the ΔhIDUA$^{op}$ construct have resulted in an 8-fold increase in the expression and 10-fold increase in the secretion of rIDUA in comparison to the inventors' previous ssAAV-hIDUA$^{op}$ construct, which increased by approximately 25% in total IDUA activity compared to a vector comprising a WT IDUA encoding sequence (ptrs-mCMV-hIDUA). This side-by-side comparison was made using plasmid transfection to eliminate any effects of differential transduction efficiency and suggests that the 15 bp deletion itself had a beneficial effect on expression levels. This scAAV-ΔhIDUA$^{op}$ is the first scAAV-IDUA vector to date, and because the scAAV vector bypasses the requirement for DNA synthesis by the host cells to convert the single-stranded (ss) vg into active double-stranded DNA, there may be further transduction benefits which will independently multiply the effects of the changes in the transgene construct itself. These results support the great therapeutic potential of scAAV9-hIDUA$^{op}$ via systemic delivery for treating MPS I in humans.

The present invention provides parvovirus vectors, e.g., AAV vectors, that comprise a nucleotide sequence encoding IDUA and are capable of expressing IDUA in a subject.

One aspect of the invention relates to a recombinant nucleic acid comprising a nucleotide sequence encoding human IDUA or a functional fragment thereof, wherein the nucleotide sequence has been codon-optimized for expression in human cells. In some embodiments, the nucleic acid comprises a nucleotide sequence that is at least 90% identical to SEQ ID NO:1, e.g., at least 91%, 92%, 93%, 94%, 95%, 96%, 97%, 98%, 99%, 99.5%, or 99.9% identical to SEQ ID NO:1. In some embodiments, the nucleic acid comprises, consists essentially of, or consists of the nucleotide sequence of SEQ ID NO:1.

```
                                                    SEQ ID NO: 1
   1 ATGCGACCTC TGAGGCCACG GGCTGCGTTG TTGGCTCTTT TGGCGTCCCT

  51 GTTGGCCGCA CCGCCTGTCG CTCCAGCAGA AGCACCCCAC CTCGTGCATG

 101 TTGATGCAGC ACGAGCACTG TGGCCGCTTC GGAGGTTTTG GAGGTCAACG

 151 GGGTTCTGTC CTCCATTGCC ACACTCTCAA GCGGATCAGT ATGTGTTGTC

 201 TTGGGATCAG CAACTGAACC TGGCCTATGT CGGTGCCGTA CCTCATCGCG

 251 GAATTAAACA GGTTCGAACC CATTGGCTCC TTGAGTTGGT TACGACACGG

 301 GGCAGCACAG GAAGGGGACT CTCTTACAAT TTCACTCACT TGGACGGATA

 351 CCTTGACCTC CTGCGAGAGA ATCAGCTGCT TCCCGGTTTC GAGTTGATGG

 401 GGTCAGCTAG CGGACACTTC ACTGATTTCG AGGATAAGCA ACAAGTTTTT

 451 GAGTGGAAAG ACCTCGTGTC ATCACTTGCC CGGAGGTATA TAGGGCGCTA

 501 CGGGCTTGCG CACGTAAGTA AGTGGAACTT TGAGACGTGG AATGAGCCTG

 551 ATCACCACGA TTTTGACAAT GTTTCTATGA CGATGCAGGG CTTTCTCAAC

 601 TACTATGACG CGTGTTCTGA AGGACTGAGA GCAGCCAGTC CGGCACTCCG

 651 CCTGGGGGGC CCAGGGGACT CCTTCCACAC ACCGCCTCGG TCCCCGCTTT

 701 CTTGGGGGCT GTTGCGACAC TGTCATGACG GTACGAACTT TTTTACAGGA

 751 GAAGCGGGCG TCCGCCTCGA TTATATTTCT CTGCATCGAA AAGGTGCGAG

 801 GTCCTCAATC TCTATCCTGG AGCAGGAGAA GGTCGTGGCA CAACAAATTA

 851 GACAACTCTT TCCTAAATTT GCCGACACCC CTATCTATAA TGATGAGGCC

 901 GACCCTCTTG TGGGTTGGTC ACTTCCGCAA CCCTGGCGGG CGGATGTGAC

 951 ATATGCAGCA ATGGTAGTCA AAGTGATCGC GCAACATCAA AACTTGCTCC

1001 TGGCAAACAC GACATCCGCT TTTCCGTATG CCTTGCTTTC AAACGATAAC

1051 GCTTTCCTTT CATACCACCC GCATCCCTTT GCACAGCGAA CCCTCACAGC

1101 GCGGTTCCAG GTCAATAACA CACGACCTCC TCACGTCCAG TTGTTGAGAA

1151 AACCTGTGCT TACTGCCATG GGACTTCTGG CACTTCTCGA CGAGGAACAG

1201 CTGTGGGCGG AGGTATCTCA AGCAGGGACT GTATTGGATA GCAACCACAC

1251 CGTAGGGGTC CTCGCCTCCG CGCACAGGCC ACAAGGACCT GCTGATGCTT

1301 GGCGAGCTGC AGTTCTGATC TACGCCAGTG ACGACACTAG GGCCCATCCG
```

-continued

```
1351 AACAGATCAG TCGCGGTGAC GCTGAGGCTC CGCGGAGTGC CCCCTGGTCC
1401 CGGTCTCGTT TACGTCACTC GCTACCTCGA CAACGGACTC TGTTCTCCGG
1451 ATGGCGAGTG GAGAAGACTT GGACGGCCTG TTTTCCCGAC CGCGGAACAA
1501 TTCCGGCGAA TGAGGGCCGC TGAGGACCCA GTAGCGGCAG CGCCAAGACC
1551 TCTCCCCGCT GGGGGCCGCC TCACCCTTAG ACCCGCTCTC AGGCTCCCCA
1601 GTCTTCTCTT GGTACACGTA TGTGCCCGAC CTGAGAAACC CCCTGGCCAG
1651 GTCACTCGCT TGCGAGCTCT TCCTTTGACT CAAGGACAAC TTGTCCTCGT
1701 TTGGAGCGAC GAGCATGTGG GCTCTAAATG CCTCTGGACT TATGAAATAC
1751 AGTTCTCACA AGATGGCAAA GCATACACCC CGGTATCTAG GAAACCCTCA
1801 ACGTTCAACC TGTTTGTATT CTCCCCCGAC ACGGGAGCCG TGTCAGGCTC
1851 CTACCGAGTT CGGGCCTTGG ACTACTGGGC TAGGCCCGGC CCCTTCTCCG
1901 ATCCAGTCCC ATATTTGGAG GTCCCTGTTC CGCGCGGACC CCCCAGCCCG
1951 GGCAATCCCT GA
```

Another aspect of the invention relates to a recombinant nucleic acid comprising a nucleotide sequence encoding human IDUA, wherein the nucleotide sequence has been truncated (15 non-coding nucleotides are removed from near the 3' end (e.g., the 15 nucleotides ending 15 nucleotides upstream of the stop codon)) for expression in human cells. As used herein, the phrase "near the 3' end" means within 50 nucleotides of the stop codon, e.g., within 40 or 30 nucleotides of the stop codon. In some embodiments, the nucleic acid comprises a nucleotide sequence that is at least 90% identical to SEQ ID NO:2, e.g., at least 91%, 92%, 93%, 94%, 95%, 96%, 97%, 98%, 99%, 99.5%, or 99.9% identical to SEQ ID NO:2. In some embodiments, the nucleic acid comprises, consists essentially of, or consists of the nucleotide sequence of SEQ ID NO:2.

SEQ ID NO: 2

```
  1 ATGCGTCCCC TGCGCCCCCG CGCCGCGCTG CTGGCGCTCC TGGCCTCGCT
 51 CCTGGCCGCG CCCCCGGTGG CCCCGGCCGA GGCCCCGCAC CTGGTGCATG
101 TGGACGCGGC CCGCGCGCTG TGGCCCCTGC GGCGCTTCTG GAGGAGCACA
151 GGCTTCTGCC CCCCGCTGCC ACACAGCCAG GCTGACCAGT ACGTCCTCAG
201 CTGGGACCAG CAGCTCAACC TCGCCTATGT GGGCGCCGTC CCTCACCGCG
251 GCATCAAGCA GGTCCGGACC CACTGGCTGC TGGAGCTTGT CACCACCAGG
301 GGGTCCACTG GACGGGGCCT GAGCTACAAC TTCACCCACC TGGACGGGTA
351 CCTGGACCTT CTCAGGGAGA ACCAGCTCCT CCCAGGGTTT GAGCTGATGG
401 GCAGCGCCTC GGGCCACTTC ACTGACTTTG AGGACAAGCA GCAGGTGTTT
451 GAGTGGAAGG ACTTGGTCTC CAGCCTGGCC AGGAGATACA TCGGTAGGTA
501 CGGACTGGCG CATGTTTCCA AGTGGAACTT CGAGACGTGG AATGAGCCAG
551 ACCACCACGA CTTTGACAAC GTCTCCATGA CCATGCAAGG CTTCCTGAAC
601 TACTACGATG CCTGCTCGGA GGGTCTGCGC GCCGCCAGCC CCGCCCTGCG
651 GCTGGGAGGC CCCGGCGACT CCTTCCACAC CCCACCGCGA TCCCCGCTGA
701 GCTGGGGCCT CCTGCGCCAC TGCCACGACG GTACCAACTT CTTCACTGGG
751 GAGGGGGGCG TGCGGCTGGA CTACATCTCC CTCCACAGGA AGGGTGCGCG
801 CAGCTCCATC TCCATCCTGG AGCAGGAGAA GGTCGTCGCG CAGCAGATCC
851 GGCAGCTCTT CCCCAAGTTC GCGGACACCC CCATTTACAA CGACGAGGCG
901 GACCCGCTGG TGGGCTGGTC CCTGCCACAG CCGTGGAGGG CGGACGTGAC
951 CTACGCGGCC ATGGTGGTGA AGGTCATCGC GCAGCATCAG AACCTGCTAC
```

-continued

```
1001 TGGCCAACAC CACCTCCGCC TTCCCCTACG CGCTCCTGAG CAACGACAAT

1051 GCCTTCCTGA GCTACCACCC GCACCCCTTC GCGCAGCGCA CGCTCACCGC

1101 GCGCTTCCAG GTCAACAACA CCCGCCCGCC GCACGTGCAG CTGTTGCGCA

1151 AGCCGGTGCT CACGGCCATG GGGCTGCTGG CGCTGCTGGA TGAGGAGCAG

1201 CTCTGGGCCG AAGTGTCGCA GGCCGGGACC GTCCTGGACA GCAACCACAC

1251 GGTGGGCGTC CTGGCCAGCG CCCACCGCCC CCAGGGCCCG GCCGACGCCT

1301 GGCGCGCCGC GGTGCTGATC TACGCGAGCG ACGACACCCG CGCCCACCCC

1351 AACCGCAGCG TCGCGGTGAC CCTGCGGCTG CGCGGGGTGC CCCCCGGCCC

1401 GGGCCTGGTC TACGTCACGC GCTACCTGGA CAACGGGCTC TGCAGCCCCG

1451 ACGGCGAGTG GCGGCGCCTG GGCCGGCCCG TCTTCCCCAC GGCAGAGCAG

1501 TTCCGGCGCA TGCGCGCGGC TGAGGACCCG GTGGCCGCGG CGCCCCGCCC

1551 CTTACCCGCC GGCGGCCGCC TGACCCTGCG CCCCGCGCTG CGGCTGCCGT

1601 CGCTTTTGCT GGTGCACGTG TGTGCGCGCC CCGAGAAGCC GCCCGGGCAG

1651 GTCACGCGGC TCCGCGCCCT GCCCCTGACC CAAGGGCAGC TGGTTCTGGT

1701 CTGGTCGGAT GAACACGTGG GCTCCAAGTG CCTGTGGACA TACGAGATCC

1751 AGTTCTCTCA GGACGGTAAG GCGTACACCC CGGTCAGCAG GAAGCCATCG

1801 ACCTTCAACC TCTTTGTGTT CAGCCCAGAC ACAGGTGCTG TCTCTGGCTC

1851 CTACCGAGTT CGAGCCCTGG ACTACTGGGC CCGACCAGGC CCCTTCTCGG

1901 ACCCTGTGCC GTACCTGGAG GTCCCTGTGT CCCCGGGCAA TCCATGA
```

Another aspect of the invention relates to a recombinant nucleic acid comprising a nucleotide sequence encoding human IDUA, wherein the nucleotide sequence has been codon-optimized and truncated (15 non-coding nucleotides are removed from near the 3' end) for expression in human cells. In some embodiments, the nucleic acid comprises a nucleotide sequence that is at least 90% identical to SEQ ID NO:3, e.g., at least 91%, 92%, 93%, 94%, 95%, 96%, 97%, 98%, 99%, 99.5%, or 99.9% identical to SEQ ID NO:3. In some embodiments, the nucleic acid comprises, consists essentially of, or consists of the nucleotide sequence of SEQ ID NO:3.

SEQ ID NO: 3

```
  1 ATGCGACCTC TGAGGCCACG GGCTGCGTTG TTGGCTCTTT TGGCGTCCCT

 51 GTTGGCCGCA CCGCCTGTCG CTCCAGCAGA AGCACCCCAC CTCGTGCATG

101 TTGATGCAGC ACGAGCACTG TGGCCGCTTC GGAGGTTTTG GAGGTCAACG

151 GGGTTCTGTC CTCCATTGCC ACACTCTCAA GCGGATCAGT ATGTGTTGTC

201 TTGGGATCAG CAACTGAACC TGGCCTATGT CGGTGCCGTA CCTCATCGCG

251 GAATTAAACA GGTTCGAACC CATTGGCTCC TTGAGTTGGT TACGACACGG

301 GGCAGCACAG GAAGGGGACT CTCTTACAAT TTCACTCACT TGGACGGATA

351 CCTTGACCTC CTGCGAGAGA ATCAGCTGCT TCCCGGTTTC GAGTTGATGG

401 GGTCAGCTAG CGGACACTTC ACTGATTTCG AGGATAAGCA ACAAGTTTTT

451 GAGTGGAAAG ACCTCGTGTC ATCACTTGCC CGGAGGTATA TAGGGCGCTA

501 CGGGCTTGCG CACGTAAGTA AGTGGAACTT TGAGACGTGG AATGAGCCTG

551 ATCACCACGA TTTTGACAAT GTTTCTATGA CGATGCAGGG CTTTCTCAAC

601 TACTATGACG CGTGTTCTGA AGGACTGAGA GCAGCCAGTC CGGCACTCCG

651 CCTGGGGGGC CCAGGGGACT CCTTCCACAC ACCGCCTCGG TCCCCGCTTT

701 CTTGGGGGCT GTTGCGACAC TGTCATGACG GTACGAACTT TTTTACAGGA

751 GAAGCGGGCG TCCGCCTCGA TTATATTTCT CTGCATCGAA AAGGTGCGAG
```

-continued

```
 801 GTCCTCAATC TCTATCCTGG AGCAGGAGAA GGTCGTGGCA CAACAAATTA
 851 GACAACTCTT TCCTAAATTT GCCGACACCC CTATCTATAA TGATGAGGCC
 901 GACCCTCTTG TGGGTTGGTC ACTTCCGCAA CCCTGGCGGG CGGATGTGAC
 951 ATATGCAGCA ATGGTAGTCA AAGTGATCGC GCAACATCAA AACTTGCTCC
1001 TGGCAAACAC GACATCCGCT TTTCCGTATG CCTTGCTTTC AAACGATAAC
1051 GCTTTCCTTT CATACCACCC GCATCCCTTT GCACAGCGAA CCCTCACAGC
1101 GCGGTTCCAG GTCAATAACA CACGACCTCC TCACGTCCAG TTGTTGAGAA
1151 AACCTGTGCT TACTGCCATG GGACTTCTGG CACTTCTCGA CGAGGAACAG
1201 CTGTGGGCGG AGGTATCTCA AGCAGGGACT GTATTGGATA GCAACCACAC
1251 CGTAGGGGTC CTCGCCTCCG CGCACAGGCC ACAAGGACCT GCTGATGCTT
1301 GGCGAGCTGC AGTTCTGATC TACGCCAGTG ACGACACTAG GGCCCATCCG
1351 AACAGATCAG TCGCGGTGAC GCTGAGGCTC CGCGGAGTGC CCCCTGGTCC
1401 CGGTCTCGTT TACGTCACTC GCTACCTCGA CAACGGACTC TGTTCTCCGG
1451 ATGGCGAGTG GAGAAGACTT GGACGGCCTG TTTTCCCGAC CGCGGAACAA
1501 TTCCGGCGAA TGAGGGCCGC TGAGGACCCA GTAGCGGCAG CGCCAAGACC
1551 TCTCCCCGCT GGGGGCCGCC TCACCCTTAG ACCCGCTCTC AGGCTCCCCA
1601 GTCTTCTCTT GGTACACGTA TGTGCCCGAC CTGAGAAACC CCCTGGCCAG
1651 GTCACTCGCT TGCGAGCTCT TCCTTTGACT CAAGGACAAC TTGTCCTCGT
1701 TTGGAGCGAC GAGCATGTGG GCTCTAAATG CCTCTGGACT TATGAAATAC
1751 AGTTCTCACA AGATGGCAAA GCATACACCC CGGTATCTAG GAAACCCTCA
1801 ACGTTCAACC TGTTTGTATT CTCCCCCGAC ACGGGAGCCG TGTCAGGCTC
1851 CTACCGAGTT CGGGCCTTGG ACTACTGGGC TAGGCCCGGC CCCTTCTCCG
1901 ATCCAGTCCC ATATTTGGAG GTCCCTGTTA GCCCGGGCAA TCCCTGA
```

Methods of codon optimizing a nucleotide sequence to maximize expression in an organism are well known in the art and can be carried out using software available to the public. The wild-type sequence of human IDUA is known in the art and can be found in databases such as GenBank. Examples of human IDUA accession numbers include A26494, AK291816, and AH002600, incorporated by reference herein in their entirety.

The invention also provides a viral vector genome comprising the IDUA nucleic acid of the invention. In certain embodiments, the IDUA nucleic acid is the wild-type human IDUA sequence or the codon-optimized sequence. The viral vector genome may be a parvovirus vector genome, e.g., an AAV vector genome. In one embodiment, a scAAV vector has a mCMV promoter, a sNRP-1 Poly A signal, and hIDUA$^{op}$, which is codon optimized and miniaturized by deleting 15 nucleotides of non-conserved sequence (ΔhIDUA$^{op}$) near the 3'-end and has a sequence at least 90% identical to SEQ ID NO:4 (ptrs-mCMV-ΔhIDUA$^{op}$), e.g., at least 91%, 92%, 93%, 94%, 95%, 96%, 97%, 98%, 99%, 99.5%, or 99.9% identical to SEQ ID NO:4.

```
                                                        SEQ ID NO: 4
  1 CAGCAGCTGC GCGCTCGCTC GCTCACTGAG GCCGCCCGGG CAAAGCCCGG
 51 GCGTCGGGCG ACCTTTGGTC GCCCGGCCTC AGTGAGCGAG CGAGCGCGCA
101 GAGAGGGAGT GGGGTTATTT CGTATTTTAT TTAGATCTGA TGGTCAGGGA
151 TTGCCCGGGC TAACAGGGAC CTCCAAATAT GGGACTGGAT CGGAGAAGGG
201 GCCGGGCCTA GCCCAGTAGT CCAAGGCCCG AACTCGGTAG GAGCCTGACA
251 CGGCTCCCGT GTCGGGGGAG AATACAAACA GGTTGAACGT TGAGGGTTTC
301 CTAGATACCG GGGTGTATGC TTTGCCATCT TGTGAGAACT GTATTTCATA
351 AGTCCAGAGG CATTTAGAGC CCACATGCTC GTCGCTCCAA ACGAGGACAA
```

-continued

401 GTTGTCCTTG AGTCAAAGGA AGAGCTCGCA AGCGAGTGAC CTGGCCAGGG

451 GGTTTCTCAG GTCGGGCACA TACGTGTACC AAGAGAAGAC TGGGGAGCCT

501 GAGAGCGGGT CTAAGGGTGA GGCGGCCCCC AGCGGGGAGA GGTCTTGGCG

551 CTGCCGCTAC TGGGTCCTCA GCGGCCCTCA TTCGCCGGAA TTGTTCCGCG

601 GTCGGGAAAA CAGGCCGTCC AAGTCTTCTC CACTCGCCAT CCGGAGAACA

651 GAGTCCGTTG TCGAGGTAGC GAGTGACGTA AACGAGACCG GGACCAGGGG

701 GCACTCCGCG GAGCCTCAGC GTCACCGCGA CTGATCTGTT CGGATGGGCC

751 CTAGTGTCGT CACTGGCGTA GATCAGAACT GCAGCTCGCC AAGCATCAGC

801 AGGTCCTTGT GGCCTGTGCG CGGAGGCGAG GACCCCTACG GTGTGGTTGC

851 TATCCAATAC AGTCCCTGCT TGAGATACCT CCGCCCACAG CTGTTCCTCG

901 TCGAGAAGTG CCAGAAGTCC CATGGCAGTA AGCACAGGTT TTCTCAACAA

951 CTGGACGTGA GGAGGTCGTG TGTTATTGAC CTGGAACCGC GCTGTGAGGG

1001 TTCGCTGTGC AAAGGGATGC GGGTGGTATG AAAGGAAAGC GTTATCGTTT

1051 GAAAGCAAGG CATACGGAAA AGCGGATGTC GTGTTTGCCA GGAGCAAGTT

1101 TTGATGTTGC GCGATCACTT TGACTACCAT TGCTGCATAT GTCACATCCG

1151 CCCGCCAGGG TTGCGGAAGT GACCAACCCA CAAGAGGGTC GGCCTCATCA

1201 TTATAGATAG GGGTGTCGGC AAATTTAGGA AAGAGTTGTC TAATTTGTTG

1251 TGCCACGACC TTCTCCTGCT CCAGGATAGA GATTGAGGAC CTCGCACCTT

1301 TTCGATGCAG AGAAATATAA TCGAGGCGGA CGCCCGCTTC TCCTGTAAAA

1351 AAGTTCGTAC CGTCATGACA GTGTCGCAAC AGCCCCCAAG AAAGCGGGGA

1401 CCGAGGCGGT GTGTGGAAGG AGTCCCCTGG GCCCCCCAGG CGGAGTGCCG

1451 GACTGGCTGC TCTCAGTCCT TCAGAACACG CGTCATAGTA GTTGAGAAAG

1501 CCCTGCATCG TCATAGAAAC ATTGTCAAAA TCGTGGTGAT CAGGCTCATT

1551 CCACGTCTCA AAGTTCCACT TACTTACGTG CGCAAGCCCG TAGCGCCCTA

1601 TATACCTCCG GGCAAGTGAT GACACGAGGT CTTTCCACTC AAAAACTTGT

1651 TGCTTATCCT CGAAATCAGT GAAGTGTCCG CTAGCTGACC CCATCAACTC

1701 GAAACCGGGA AGCAGCTGAT TCTCTCGCAG GAGGTCAAGG TATCCGTCCA

1751 AGTGAGTGAA ATTGTAAGAG AGTCCCCTTC CTGTGCTGCC CCGTGTCGTA

1801 ACCAACTCAA GGAGCCAATG GGTTCGAACC TGTTTAATTC CGCGATGAGG

1851 TACGGCACCG ACATAGGCCA GGTTCAGTTG CTGATCCCAA GACAACACAT

1901 ACTGATCCGC TTGAGAGTGT GGCAATGGAG GACAGAACCC CGTTGACCTC

1951 CAAAACCTCC GAAGCGGCCA CAGTGCTCGT GCTGCATCAA CATGCACGAG

2001 GTGGGGTGCT TCTGCTGGAG CGACAGGCGG TGCGGCCAAC AGGGACGCCA

2051 AAAGAGCCAA CAACGCAGCC CGTGGCCTCA GAGGTCGCAT GGCGACCGGT

2101 CGAGCGGTTC ACTAAACGAG CTCTGCTTAT ATAGACCTCC CACCGTACAC

2151 GCCTACCGCC CATTTGCGTC AATGGGGCGG AGTTGTTACG ACATTTTGGA

2201 AAGTCCCGTT GATTTTGGTG CCAAAACAAA CTCCCATTGA CGTCAATGGG

2251 GTGGAGACTT GGAAATCCCC GTGAGTCCGG GGGTCGTTGG GCGGTCAGCC

2301 AGGCGGGCCA TTTACCGTAA GTTATGTAAC GAAAGCTTCC TAGGAACCCC

2351 TAGTGATGGA GTTGGCCACT CCCTCTCTGC GCGCTCGCTC GCTCACTGAG

2401 GCCGGGCGAC CAAAGGTCGC CCGACGCCCG GGCTTTGCCC GGGCGGCCTC

-continued

2451 AGTGAGCGAG CGAGCGCGCA GCTGGCGTAA TAGCGAAGAG GCCCGCACCG

2501 ATCGCCCTTC CCAACAGTTG CGCAGCCTGA ATGGCGAATG GCGATTCCGT

2551 TGCAATGGCT GGCGGTAATA TTGTTCTGGA TATTACCAGC AAGGCCGATA

2601 GTTTGAGTTC TTCTACTCAG GCAAGTGATG TTATTACTAA TCAAAGAAGT

2651 ATTGCGACAA CGGTTAATTT GCGTGATGGA CAGACTCTTT TACTCGGTGG

2701 CCTCACTGAT TATAAAAACA CTTCTCAGGA TTCTGGCGTA CCGTTCCTGT

2751 CTAAAATCCC TTTAATCGGC CTCCTGTTTA GCTCCCGCTC TGATTCTAAC

2801 GAGGAAAGCA CGTTATACGT GCTCGTCAAA GCAACCATAG TACGCGCCCT

2851 GTAGCGGCGC ATTAAGCGCG GCGGGTGTGG TGGTTACGCG CAGCGTGACC

2901 GCTACACTTG CCAGCGCCCT AGCGCCCGCT CCTTTCGOTT TCTTCCCTTC

2951 CTTTCTCGCC ACGTTCGCCG GCTTTCCCCG TCAAGCTCTA AATCGGGGGC

3001 TCCCTTTAGG GTTCCGATTT AGTGCTTTAC GGCACCTCGA CCCCAAAAAA

3051 CTTGATTAGG GTGATGGTTC ACGTAGTGGG CCATCGCCCT GATAGACGGT

3101 TTTTCGCCCT TTGACGTTGG AGTCCACGTT CTTTAATAGT GGACTCTTGT

3151 TCCAAACTGG AACAACACTC AACCCTATCT CGGTCTATTC TTTTGATTTA

3201 TAAGGGATTT TGCCGATTTC GGCCTATTGG TTAAAAAATG AGCTGATTTA

3251 ACAAAAATTT AACGCGAATT TTAACAAAAT ATTAACGCTT ACAATTTAAA

3301 TATTTGCTTA TACAATCTTC CTGTTTTTGG GGCTTTTCTG ATTATCAACC

3351 GGGGTACATA TGATTGACAT GCTAGTTTTA CGATTACCGT TCATCGATTC

3401 TCTTGTTTGC TCCAGACTCT CAGGCAATGA CCTGATAGCC TTTGTAGAGA

3451 CCTCTCAAAA ATAGCTACCC TCTCCGGCAT GAATTTATCA GCTAGAACGG

3501 TTGAATATCA TATTGATGGT GATTTGACTG TCTCCGGCCT TTCTCACCCG

3551 TTTGAATCTT TACCTACACA TTACTCAGGC ATTGCATTTA AAATATATGA

3601 GGGTTCTAAA AATTTTTATC CTTGCGTTGA AATAAAGGCT TCTCCCGCAA

3651 AAGTATTACA GGGTCATAAT GTTTTTGGTA CAACCGATTT AGCTTTATGC

3701 TCTGAGGCTT TATTGCTTAA TTTTGCTAAT TCTTTGCCTT GCCTGTATGA

3751 TTTATTGGAT GTTGGAATCG CCTGATGCGG TATTTTCTCC TTACGCATCT

3801 GTGCGGTATT TCACACCGCA TATGGTGCAC TCTCAGTACA ATCTGCTCTG

3851 ATGCCGCATA GTTAAGCCAG CCCCGACACC CGCCAACACC CGCTGACGCG

3901 CCCTGACGGG CTTGTCTGCT CCCGGCATCC GCTTACAGAC AAGCTGTGAC

3951 CGTCTCCGGG AGCTGCATGT GTCAGAGGTT TTCACCGTCA TCACCGAAAC

4001 GCGCGAGACG AAAGGGCCTC GTGATACGCC TATTTTTATA GGTTAATGTC

4051 ATGATAATAA TGGTTTCTTA GACGTCAGGT GGCACTTTTC GGGGAAATGT

4101 GCGCGGAACC CCTATTTGTT TATTTTTCTA AATACATTCA AATATGTATC

4151 CGCTCATGAG ACAATAACCC TGATAAATGC TTCAATAATA TTGAAAAAGG

4201 AAGAGTATGA GTATTCAACA TTTCCGTGTC GCCCTTATTC CCTTTTTTGC

4251 GGCATTTTGC CTTCCTGTTT TTGCTCACCC AGAAACGCTG GTGAAAGTAA

4301 AAGATGCTGA AGATCAGTTG GGTGCACGAG TGGGTTACAT CGAACTGGAT

4351 CTCAACAGCG GTAAGATCCT TGAGAGTTTT CGCCCCGAAG AACGTTTTCC

4401 AATGATGAGC ACTTTTAAAG TTCTGCTATG TGGCGCGGTA TTATCCCGTA

-continued

```
4451 TTGACGCCGG GCAAGAGCAA CTCGGTCGCC GCATACACTA TTCTCAGAAT

4501 GACTTGGTTG AGTACTCACC AGTCACAGAA AAGCATCTTA CGGATGGCAT

4551 GACAGTAAGA GAATTATGCA GTGCTGCCAT AACCATGAGT GATAACACTG

4601 CGGCCAACTT ACTTCTGACA ACGATCGGAG GACCGAAGGA GCTAACCGCT

4651 TTTTTGCACA ACATGGGGGA TCATGTAACT CGCCTTGATC GTTGGGAACC

4701 GGAGCTGAAT GAAGCCATAC CAAACGACGA GCGTGACACC ACGATGCCTG

4751 TAGCAATGGC AACAACGTTG CGCAAACTAT TAACTGGCGA ACTACTTACT

4801 CTAGCTTCCC GGCAACAATT AATAGACTGG ATGGAGGCGG ATAAAGTTGC

4851 AGGACCACTT CTGCGCTCGG CCCTTCCGGC TGGCTGGTTT ATTGCTGATA

4901 AATCTGGAGC CGGTGAGCGT GGGTCTCGCG GTATCATTGC AGCACTGGGG

4951 CCAGATGGTA AGCCCTCCCG TATCGTAGTT ATCTACACGA CGGGGAGTCA

5001 GGCAACTATG GATGAACGAA ATAGACAGAT CGCTGAGATA GGTGCCTCAC

5051 TGATTAAGCA TTGGTAACTG TCAGACCAAG TTTACTCATA TATACTTTAG

5101 ATTGATTTAA AACTTCATTT TTAATTTAAA AGGATCTAGG TGAAGATCCT

5151 TTTTGATAAT CTCATGACCA AAATCCCTTA ACGTGAGTTT TCGTTCCACT

5201 GAGCGTCAGA CCCCGTAGAA AAGATCAAAG GATCTTCTTG AGATCCTTTT

5251 TTTCTGCGCG TAATCTGCTG CTTGCAAACA AAAAAACCAC CGCTACCAGC

5301 GGTGGTTTGT TTGCCGGATC AAGAGCTACC AACTCTTTTT CCGAAGGTAA

5351 CTGGCTTCAG CAGAGCGCAG ATACCAAATA CTGTTCTTCT AGTGTAGCCG

5401 TAGTTAGGCC ACCACTTCAA GAACTCTGTA GCACCGCCTA CATACCTCGC

5451 TCTGCTAATC CTGTTACCAG TGGCTGCTGC CAGTGGCGAT AAGTCGTGTC

5501 TTACCGGGTT GGACTCAAGA CGATAGTTAC CGGATAAGGC GCAGCGGTCG

5551 GGCTGAACGG GGGGTTCGTG CACACAGCCC AGCTTGGAGC GAACGACCTA

5601 CACCGAACTG AGATACCTAC AGCGTGAGCT ATGAGAAAGC GCCACGCTTC

5651 CCGAAGGGAG AAAGGCGGAC AGGTATCCGG TAAGCGGCAG GGTCGGAACA

5701 GGAGAGCGCA CGAGGGAGCT TCCAGGGGGA AACGCCTGGT ATCTTTATAG

5751 TCCTGTCGGG TTTCGCCACC TCTGACTTGA GCGTCGATTT TTGTGATGCT

5801 CGTCAGGGGG GCGGAGCCTA TGGAAAAACG CCAGCAACGC GGCCTTTTTA

5851 CGGTTCCTGG CCTTTTGCTG GCCTTTTGCT CACATGTTCT TTCCTGCGTT

5901 ATCCCCTGAT TCTGTGGATA ACCGTATTAC CGCCTTTGAG TGAGCTGATA

5951 CCGCTCGCCG CAGCCGAACG ACCGAGCGCA GCGAGTCAGT GAGCGAGGAA

6001 GCGGAAGAGC GCCCAATACG CAAACCGCCT CTCCCCGCGC GTTGGCCGAT

6051 TCATTAATG
```

In one embodiment, a scAAV vector has a mCMV promoter, a sNRP-1 Poly A signal, and hIDUA$^{op}$, which is codon optimized and has a sequence at least 90% identical to SEQ DD NO:5 (ptrs-mCMV-hIDUA$^{op}$), e.g., at least 91%, 92%, 93%, 94%, 95%, 96%, 97%, 98%, 99%, 99.5%, or 99.9% identical to SEQ ID NO:5.

SEQ ID NO: 5

```
  1 CAGCAGCTGC GCGCTCGCTC GCTCACTGAG GCCGCCCGGG CAAAGCCCGG

 51 GCGTCGGGCG ACCTTTGGTC GCCCGGCCTC AGTGAGCGAG CGAGCGCGCA

101 GAGAGGGAGT GGGGTTATTT CGTATTTTAT TTAGATCTGA TGGTCAGGGA

151 TTGCCCGGGC TGGGGGGTCC GCGCGGAACA GGGACCTCCA AATATGGGAC
```

-continued

201 TGGATCGGAG AAGGGGCCGG GCCTAGCCCA GTAGTCCAAG GCCCGAACTC

251 GGTAGGAGCC TGACACGGCT CCCGTGTCGG GGGAGAATAC AAACAGGTTG

301 AACGTTGAGG GTTTCCTAGA TACCGGGGTG TATGCTTTGC CATCTTGTGA

351 GAACTGTATT TCATAAGTCC AGAGGCATTT AGAGCCCACA TGCTCGTCGC

401 TCCAAACGAG GACAAGTTGT CCTTGAGTCA AAGGAAGAGC TCGCAAGCGA

451 GTGACCTGGC CAGGGGGTTT CTCAGGTCGG GCACATACGT GTACCAAGAG

501 AAGACTGGGG AGCCTGAGAG CGGGTCTAAG GGTGAGGGGG CCCCCAGCGG

551 GGAGAGGTCT TGGCGCTGCC GCTACTGGGT CCTCAGCGGC CCTCATTCGC

601 CGGAATTGTT CCGCGGTCGG GAAAACAGGC CGTCCAAGTC TTCTCCACTC

651 GCCATCCGGA GAACAGAGTC CGTTGTCGAG GTAGCGAGTG ACGTAAACGA

701 GACCGGGACC AGGGGGCACT CCGCGGAGCC TCAGCGTCAC CGCGACTGAT

751 CTGTTCGGAT GGGCCCTAGT GTCGTCACTG GCGTAGATCA GAACTGCAGC

801 TCGCCAAGCA TCAGCAGGTC CTTGTGGCCT GTGCGCGGAG GCGAGGACCC

851 CTACGGTGTG GTTGCTATCC AATACAGTCC CTGCTTGAGA TACCTCCGCC

901 CACAGCTGTT CCTCGTCGAG AAGTGCCAGA AGTCCCATGG CAGTAAGCAC

951 AGGTTTTCTC AACAACTGGA CGTGAGGAGG TCGTGTGTTA TTGACCTGGA

1001 ACCGCGCTGT GAGGGTTCGC TGTGCAAAGG GATGCGGGTG GTATGAAAGG

1051 AAAGCGTTAT CGTTTGAAAG CAAGGCATAC GGAAAAGCGG ATGTCGTGTT

1101 TGCCAGGAGC AAGTTTTGAT GTTGCGCGAT CACTTTGACT ACCATTGCTG

1151 CATATGTCAC ATCCGCCCGC CAGGGTTGCG GAAGTGACCA ACCCACAAGA

1201 GGGTCGGCCT CATCATTATA GATAGGGGTG TCGGCAAATT TAGGAAAGAG

1251 TTGTCTAATT TGTTGTGCCA CGACCTTCTC CTGCTCCAGG ATAGAGATTG

1301 AGGACCTCGC ACCTTTTCGA TGCAGAGAAA TATAATCGAG GCGGACGCCC

1351 GCTTCTCCTG TAAAAAAGTT CGTACCGTCA TGACAGTGTC GCAACAGCCC

1401 CCAAGAAAGC GGGGACCGAG GCGGTGTGTG GAAGGAGTCC CCTGGGCCCC

1451 CCAGGCGGAG TGCCGGACTG GCTGCTCTCA GTCCTTCAGA ACACGCGTCA

1501 TAGTAGTTGA GAAAGCCCTG CATCGTCATA GAAACATTGT CAAAATCGTG

1551 GTGATCAGGC TCATTCCACG TCTCAAAGTT CCACTTACTT ACGTGCGCAA

1601 GCCCGTAGCG CCCTATATAC CTCCGGGCAA GTGATGACAC GAGGTCTTTC

1651 CACTCAAAAA CTTGTTGCTT ATCCTCGAAA TCAGTGAAGT GTCCGCTAGC

1701 TGACCCCATC AACTCGAAAC CGGGAAGCAG CTGATTCTCT CGCAGGAGGT

1751 CAAGGTATCC GTCCAAGTGA GTGAAATTGT AAGAGAGTCC CCTTCCTGTG

1801 CTGCCCCGTG TCGTAACCAA CTCAAGGAGC CAATGGGTTC GAACCTGTTT

1851 AATTCCGCGA TGAGGTACGG CACCGACATA GGCCAGGTTC AGTTGCTGAT

1901 CCCAAGACAA CACATACTGA TCCGCTTGAG AGTGTGGCAA TGGAGGACAG

1951 AACCCCGTTG ACCTCCAAAA CCTCCGAAGC GGCCACAGTG CTCGTGCTGC

2001 ATCAACATGC ACGAGGTGGG GTGCTTCTGC TGGAGCGACA GGGGGTGCGG

2051 CCAACAGGGA CGCCAAAAGA GCCAACAACG CAGCCCGTGG CCTCAGAGGT

2101 CGCATGGCGA CCGGTCGAGC GGTTCACTAA ACGAGCTCTG CTTATATAGA

2151 CCTCCCACCG TACACGCCTA CCGCCCATTT GCGTCAATGG GGCGGAGTTG

-continued

2201 TTACGACATT TTGGAAAGTC CCGTTGATTT TGGTGCCAAA ACAAACTCCC

2251 ATTGACGTCA ATGGGGTGGA GACTTGGAAA TCCCCGTGAG TCCGGGGGTC

2301 GTTGGGCGGT CAGCCAGGCG GGCCATTTAC CGTAAGTTAT GTAACGAAAG

2351 CTTCCTAGGA ACCCCTAGTG ATGGAGTTGG CCACTCCCTC TCTGCGCGCT

2401 CGCTCGCTCA CTGAGGCCGG GCGACCAAAG GTCGCCCGAC GCCCGGGCTT

2451 TGCCCGGGCG GCCTCAGTGA GCGAGCGAGC GCGCAGCTGG CGTAATAGCG

2501 AAGAGGCCCG CACCGATCGC CCTTCCCAAC AGTTGCGCAG CCTGAATGGC

2551 GAATGGCGAT TCCGTTGCAA TGGCTGGCGG TAATATTGTT CTGGATATTA

2601 CCAGCAAGGC CGATAGTTTG AGTTCTTCTA CTCAGGCAAG TGATGTTATT

2651 ACTAATCAAA GAAGTATTGC GACAACGGTT AATTTGCGTG ATGGACAGAC

2701 TCTTTTACTC GGTGGCCTCA CTGATTATAA AAACACTTCT CAGGATTCTG

2751 GCGTACCGTT CCTGTCTAAA ATCCCTTTAA TCGGCCTCCT GTTTAGCTCC

2801 CGCTCTGATT CTAACGAGGA AAGCACGTTA TACGTGCTCG TCAAAGCAAC

2851 CATAGTACGC GCCCTGTAGC GGCGCATTAA GCGCGGCGGG TGTGGTGGTT

2901 ACGCGCAGCG TGACCGCTAC ACTTGCCAGC GCCCTAGCGC CCGCTCCTTT

2951 CGCTTTCTTC CCTTCCTTTC TCGCCACGTT CGCCGGCTTT CCCCGTCAAG

3001 CTCTAAATCG GGGGCTCCCT TTAGGGTTCC GATTTAGTGC TTTACGGCAC

3051 CTCGACCCCA AAAAACTTGA TTAGGGTGAT GGTTCACGTA GTGGGCCATC

3101 GCCCTGATAG ACGGTTTTTC GCCCTTTGAC GTTGGAGTCC ACGTTCTTTA

3151 ATAGTGGACT CTTGTTCCAA ACTGGAACAA CACTCAACCC TATCTCGGTC

3201 TATTCTTTTG ATTTATAAGG GATTTTGCCG ATTTCGGCCT ATTGGTTAAA

3251 AAATGAGCTG ATTTAACAAA AATTTAACGC GAATTTTAAC AAAATATTAA

3301 CGCTTACAAT TTAAATATTT GCTTATACAA TCTTCCTGTT TTTGGGGCTT

3351 TTCTGATTAT CAACCGGGGT ACATATGATT GACATGCTAG TTTTACGATT

3401 ACCGTTCATC GATTCTCTTG TTTGCTCCAG ACTCTCAGGC AATGACCTGA

3451 TAGCCTTTGT AGAGACCTCT CAAAAATAGC TACCCTCTCC GGCATGAATT

3501 TATCAGCTAG AACGGTTGAA TATCATATTG ATGGTGATTT GACTGTCTCC

3551 GGCCTTTCTC ACCCGTTTGA ATCTTTACCT ACACATTACT CAGGCATTGC

3601 ATTTAAAATA TATGAGGGTT CTAAAAATTT TTATCCTTGC GTTGAAATAA

3651 AGGCTTCTCC CGCAAAAGTA TTACAGGGTC ATAATGTTTT TGGTACAACC

3701 GATTTAGCTT TATGCTCTGA GGCTTTATTG CTTAATTTTG CTAATTCTTT

3751 GCCTTGCCTG TATGATTTAT TGGATGTTGG AATCGCCTGA TGCGGTATTT

3801 TCTCCTTACG CATCTGTGCG GTATTTCACA CCGCATATGG TGCACTCTCA

3851 GTACAATCTG CTCTGATGCC GCATAGTTAA GCCAGCCCCG ACACCCGCCA

3901 ACACCCGCTG ACGCGCCCTG ACGGGCTTGT CTGCTCCCGG CATCCGCTTA

3951 CAGACAAGCT GTGACCGTCT CCGGGAGCTG CATGTGTCAG AGGTTTTCAC

4001 CGTCATCACC GAAACGCGCG AGACGAAAGG GCCTCGTGAT ACGCCTATTT

4051 TTATAGGTTA ATGTCATGAT AATAATGGTT TCTTAGACGT CAGGTGGCAC

4101 TTTTCGGGGA AATGTGCGCG GAACCCCTAT TTGTTTATTT TTCTAAATAC

4151 ATTCAAATAT GTATCCGCTC ATGAGACAAT AACCCTGATA AATGCTTCAA

4201 TAATATTGAA AAAGGAAGAG TATGAGTATT CAACATTTCC GTGTCGCCCT

-continued

4251 TATTCCCTTT TTTGCGGCAT TTTGCCTTCC TGTTTTTGCT CACCCAGAAA

4301 CGCTGGTGAA AGTAAAAGAT GCTGAAGATC AGTTGGGTGC ACGAGTGGGT

4351 TACATCGAAC TGGATCTCAA CAGCGGTAAG ATCCTTGAGA GTTTTCGCCC

4401 CGAAGAACGT TTTCCAATGA TGAGCACTTT TAAAGTTCTG CTATGTGGCG

4451 CGGTATTATC CCGTATTGAC GCCGGGCAAG AGCAACTCGG TCGCCGCATA

4501 CACTATTCTC AGAATGACTT GGTTGAGTAC TCACCAGTCA CAGAAAAGCA

4551 TCTTACGGAT GGCATGACAG TAAGAGAATT ATGCAGTGCT GCCATAACCA

4601 TGAGTGATAA CACTGCGGCC AACTTACTTC TGACAACGAT CGGAGGACCG

4651 AAGGAGCTAA CCGCTTTTTT GCACAACATG GGGGATCATG TAACTCGCCT

4701 TGATCGTTGG GAACCGGAGC TGAATGAAGC CATACCAAAC GACGAGCGTG

4751 ACACCACGAT GCCTGTAGCA ATGGCAACAA CGTTGCGCAA ACTATTAACT

4801 GGCGAACTAC TTACTCTAGC TTCCCGGCAA CAATTAATAG ACTGGATGGA

4851 GGCGGATAAA GTTGCAGGAC CACTTCTGCG CTCGGCCCTT CCGGCTGGCT

4901 GGTTTATTGC TGATAAATCT GGAGCCGGTG AGCGTGGGTC TCGCGGTATC

4951 ATTGCAGCAC TGGGGCCAGA TGGTAAGCCC TCCCGTATCG TAGTTATCTA

5001 CACGACGGGG AGTCAGGCAA CTATGGATGA ACGAAATAGA CAGATCGCTG

5051 AGATAGGTGC CTCACTGATT AAGCATTGGT AACTGTCAGA CCAAGTTTAC

5101 TCATATATAC TTTAGATTGA TTTAAAACTT CATTTTTAAT TTAAAAGGAT

5151 CTAGGTGAAG ATCCTTTTTG ATAATCTCAT GACCAAAATC CCTTAACGTG

5201 AGTTTTCGTT CCACTGAGCG TCAGACCCCG TAGAAAAGAT CAAAGGATCT

5251 TCTTGAGATC CTTTTTTTCT GCGCGTAATC TGCTGCTTGC AAACAAAAAA

5301 ACCACCGCTA CCAGCGGTGG TTTGTTTGCC GGATCAAGAG CTACCAACTC

5351 TTTTTCCGAA GGTAACTGGC TTCAGCAGAG CGCAGATACC AAATACTGTT

5401 CTTCTAGTGT AGCCGTAGTT AGGCCACCAC TTCAAGAACT CTGTAGCACC

5451 GCCTACATAC CTCGCTCTGC TAATCCTGTT ACCAGTGGCT GCTGCCAGTG

5501 GCGATAAGTC GTGTCTTACC GGGTTGGACT CAAGACGATA GTTACCGGAT

5551 AAGGCGCAGC GGTCGGGCTG AACGGGGGGT TCGTGCACAC AGCCCAGCTT

5601 GGAGCGAACG ACCTACACCG AACTGAGATA CCTACAGCGT GAGCTATGAG

5651 AAAGCGCCAC GCTTCCCGAA GGGAGAAAGG CGGACAGGTA TCCGGTAAGC

5701 GGCAGGGTCG GAACAGGAGA GCGCACGAGG GAGCTTCCAG GGGGAAACGC

5751 CTGGTATCTT TATAGTCCTG TCGGGTTTCG CCACCTCTGA CTTGAGCGTC

5801 GATTTTTGTG ATGCTCGTCA GGGGGGCGGA GCCTATGGAA AAACGCCAGC

5851 AACGCGGCCT TTTTACGGTT CCTGGCCTTT TGCTGGCCTT TTGCTCACAT

5901 GTTCTTTCCT GCGTTATCCC CTGATTCTGT GGATAACCGT ATTACCGCCT

5951 TTGAGTGAGC TGATACCGCT CGCCGCAGCC GAACGACCGA GCGCAGCGAG

6001 TCAGTGAGCG AGGAAGCGGA AGAGCGCCCA ATACGCAAAC CGCCTCTCCC

6051 CGCGCGTTGG CCGATTCATT AATG

In one embodiment, a scAAV vector has a mCMV promoter, a sNRP-1 Poly A signal, and hIDUA, which has a sequence at least 90% identical to SEQ ID NO:6 (ptrs-mCMV-hIDUA), e.g., at least 91%, 92%, 93%, 94%, 95%, 96%, 97%, 98%, 99%, 99.5%, or 99.9% identical to SEQ ID NO:6.

SEQ ID NO: 6

```
   1 CAGCAGCTGC GCGCTCGCTC GCTCACTGAG GCCGCCCGGG CAAAGCCCGG
  51 GCGTCGGGCG ACCTTTGGTC GCCCGGCCTC AGTGAGCGAG CGAGCGCGCA
 101 GAGAGGGAGT GGGGTTATTT CGTATTTTAT TTAGATCTGA TGGTCATGGA
 151 TTGCCCGGGG ATGGGGGCCC TCTTGGCACA GGGACCTCCA GGTACGGCAC
 201 AGGGTCCGAG AAGGGGCCTG GTCGGGCCCA GTAGTCCAGG GCTCGAACTC
 251 GGTAGGAGCC AGAGACAGCA CCTGTGTCTG GGCTGAACAC AAAGAGGTTG
 301 AAGGTCGATG GCTTCCTGCT GACCGGGGTG TACGCCTTAC CGTCCTGAGA
 351 GAACTGGATC TCGTATGTCC ACAGGCACTT GGAGCCCACG TGTTCATCCG
 401 ACCAGACCAG AACCAGCTGC CCTTGGGTCA GGGGCAGGGC GCGGAGCCGC
 451 GTGACCTGCC CGGGCGGCTT CTCGGGGCGC GCACACACGT GCACCAGCAA
 501 AAGCGACGGC AGCCGCAGCG CGGGGCGCAG GGTCAGGGGG CCGCCGGCGG
 551 GTAAGGGGCG GGGCGCCGCG GCCACCGGGT CCTCAGCCGC GCGCATGCGC
 601 CGGAACTGCT CTGCCGTGGG GAAGACGGGC CGGCCCAGGC GCCGCCACTC
 651 GCCGTCGGGG CTGCAGAGCC CGTTGTCCAG GTAGCGCGTG ACGTAGACCA
 701 GGCCCGGGCC GGGGGGCACC CCGCGCAGCC GCAGGGTCAC CGCGACGCTG
 751 CGGTTGGGGT GGGCGCGGGT GTCGTCGCTC GCGTAGATCA GCACCGCGGC
 801 GCGCCAGGCG TCGGCCGGGC CCTGGGGGCG GTGGGCGCTG GCCAGGACGC
 851 CCACCGTGTG GTTGCTGTCC AGGACGGTCC CGGCCTGCGA CACTTCGGCC
 901 CAGAGCTGCT CCTCATCCAG CAGCGCCAGC AGCCCCATGG CCGTGAGCAC
 951 CGGCTTGCGC AACAGCTGCA CGTGCGGCGG GCGGGTGTTG TTGACCTGGA
1001 AGCGCGCGGT GAGCGTGCGC TGCGCGAAGG GGTGCGGGTG GTAGCTCAGG
1051 AAGGCATTGT CGTTGCTCAG GAGCGCGTAG GGGAAGGCGG AGGTGGTGTT
1101 GGCCAGTAGC AGGTTCTGAT GCTGCGCGAT GACCTTCACC ACCATGGCCG
1151 CGTAGGTCAC GTCCGCCCTC CACGGCTGTG GCAGGGACCA GCCCACCAGC
1201 GGGTCCGCCT CGTCGTTGTA AATGGGGGTG TCCGCGAACT TGGGGAAGAG
1251 CTGCCGGATC TGCTGCGCGA CGACCTTCTC CTGCTCCAGG ATGGAGATGG
1301 AGCTGCGCGC ACCCTTCCTG TGGAGGGAGA TGTAGTCCAG CCGCACGCCC
1351 GCCTCCCCAG TGAAGAAGTT GGTACCGTCG TGGCAGTGGC GCAGGAGGCC
1401 CCAGCTCAGC GGGGATCGCG GTGGGGTGTG GAAGGAGTCG CCGGGGCCTC
1451 CCAGCCGCAG GGCGGGGCTG GCGGCGCGCA GACCCTCCGA GCAGGCATCG
1501 TAGTAGTTCA GGAAGCCTTG CATGGTCATG GAGACGTTGT CAAAGTCGTG
1551 GTGGTCTGGC TCATTCCACG TCTCGAAGTT CCACTTGGAA ACATGCGCCA.
1601 GTCCGTACCT ACCGATGTAT CTCCTGGCCA GGCTGGAGAC CAAGTCCTTC
1651 CACTCAAACA CCTGCTGCTT GTCCTCAAAG TCAGTGAAGT GGCCCGAGGC
1701 GCTGCCCATC AGCTCAAACC CTGGGAGGAG CTGGTTCTCC CTGAGAAGGT
1751 CCAGGTACCC GTCCAGGTGG GTGAAGTTGT AGCTCAGGCC CCGTCCAGTG
1801 GACCCCCTGG TGGTGACAAG CTCCAGCAGC CAGTGGGTCC GGACCTGCTT
1851 GATGCCGCGG TGAGGGACGG CGCCCACATA GGCGAGGTTG AGCTGCTGGT
```

-continued

1901 CCCAGCTGAG GACGTACTGG TCAGCCTGGC TGTGTGGCAG CGGGGGGCAG
1951 AAGCCTGTGC TCCTCCAGAA GCGCCGCAGG GGCCACAGCG CGCGGGCCGC
2001 GTCCACATGC ACCAGGTGCG GGGCCTCGGC CGGGGCCACC GGGGGCGCGG
2051 CCAGGAGCGA GGCCAGGAGC GCCAGCAGCG CGGCGCGGGG GCGCAGGGGA
2101 CGCATGGCGA CCGGTCGAGC GGTTCACTAA ACGAGCTCTG CTTATATAGA
2151 CCTCCCACCG TACACGCCTA CCGCCCATTT GCGTCAATGG GGCGGAGTTG
2201 TTACGACATT TTGGAAAGTC CCGTTGATTT TGGTGCCAAA ACAAACTCCC
2251 ATTGACGTCA ATGGGGTGGA GACTTGGAAA TCCCCGTGAG TCCGGGGGTC
2301 GTTGGGGGGT CAGCCAGGCG GGCCATTTAC CGTAAGTTAT GTAACGAAAG
2351 CTTCCTAGGA ACCCCTAGTG ATGGAGTTGG CCACTCCCTC TCTGCGCGCT
2401 CGCTCGCTCA CTGAGGCCGG GCGACCAAAG GTCGCCCGAC GCCCGGGCTT
2451 TGCCCGGGCG GCCTCAGTGA GCGAGCGAGC GCGCAGCTGG CGTAATAGCG
2501 AAGAGGCCCG CACCGATCGC CCTTCCCAAC AGTTGCGCAG CCTGAATGGC
2551 GAATGGCGAT TCCGTTGCAA TGGCTGGCGG TAATATTGTT CTGGATATTA
2601 CCAGCAAGGC CGATAGTTTG AGTTCTTCTA CTCAGGCAAG TGATGTTATT
2651 ACTAATCAAA GAAGTATTGC GACAACGGTT AATTTGCGTG ATGGACAGAC
2701 TCTTTTACTC GGTGGCCTCA CTGATTATAA AAACACTTCT CAGGATTCTG
2751 GCGTACCGTT CCTGTCTAAA ATCCCTTTAA TCGGCCTCCT GTTTAGCTCC
2801 CGCTCTGATT CTAACGAGGA AAGCACGTTA TACGTGCTCG TCAAAGCAAC
2851 CATAGTACGC GCCCTGTAGC GGCGCATTAA GCGCGGGGGG TGTGGTGGTT
2901 ACGCGCAGCG TGACCGCTAC ACTTGCCAGC GCCCTAGCGC CCGCTCCTTT
2951 CGCTTTCTTC CCTTCCTTTC TCGCCACGTT CGCCGGCTTT CCCCGTCAAG
3001 CTCTAAATCG GGGGCTCCCT TTAGGGTTCC GATTTAGTGC TTTACGGCAC
3051 CTCGACCCCA AAAAACTTGA TTAGGGTGAT GGTTCACGTA GTGGGCCATC
3101 GCCCTGATAG ACGGTTTTTC GCCCTTTGAC GTTGGAGTCC ACGTTCTTTA
3151 ATAGTGGACT CTTGTTCCAA ACTGGAACAA CACTCAACCC TATCTCGGTC
3201 TATTCTTTTG ATTTATAAGG GATTTTGCCG ATTTCGGCCT ATTGGTTAAA
3251 AAATGAGCTG ATTTAACAAA AATTTAACGC GAATTTTAAC AAAATATTAA
3301 CGCTTACAAT TTAAATATTT GCTTATACAA TCTTCCTGTT TTTGGGGCTT
3351 TTCTGATTAT CAACCGGGGT ACATATGATT GACATGCTAG TTTTACGATT
3401 ACCGTTCATC GATTCTCTTG TTTGCTCCAG ACTCTCAGGC AATGACCTGA
3451 TAGCCTTTGT AGAGACCTCT CAAAAATAGC TACCCTCTCC GGCATGAATT
3501 TATCAGCTAG AACGGTTGAA TATCATATTG ATGGTGATTT GACTGTCTCC
3551 GGCCTTTCTC ACCCGTTTGA ATCTTTACCT ACACATTACT CAGGCATTGC
3601 ATTTAAAATA TATGAGGGTT CTAAAAATTT TTATCCTTGC GTTGAAATAA
3651 AGGCTTCTCC CGCAAAAGTA TTACAGGGTC ATAATGTTTT TGGTACAACC
3701 GATTTAGCTT TATGCTCTGA GGCTTTATTG CTTAATTTTG CTAATTCTTT
3751 GCCTTGCCTG TATGATTTAT TGGATGTTGG AATCGCCTGA TGCGGTATTT
3801 TCTCCTTACG CATCTGTGCG GTATTTCACA CCGCATATGG TGCACTCTCA
3851 GTACAATCTG CTCTGATGCC GCATAGTTAA GCCAGCCCCG ACACCCGCCA

-continued

3901 ACACCCGCTG ACGCGCCCTG ACGGGCTTGT CTGCTCCCGG CATCCGCTTA

3951 CAGACAAGCT GTGACCGTCT CCGGGAGCTG CATGTGTCAG AGGTTTTCAC

4001 CGTCATCACC GAAACGCGCG AGACGAAAGG GCCTCGTGAT ACGCCTATTT

4051 TTATAGGTTA ATGTCATGAT AATAATGGTT TCTTAGACGT CAGGTGGCAC

4101 TTTTCGGGGA AATGTGCGCG GAACCCCTAT TTGTTTATTT TTCTAAATAC

4151 ATTCAAATAT GTATCCGCTC ATGAGACAAT AACCCTGATA AATGCTTCAA

4201 TAATATTGAA AAAGGAAGAG TATGAGTATT CAACATTTCC GTGTCGCCCT

4251 TATTCCCTTT TTTGCGGCAT TTTGCCTTCC TGTTTTTGCT CACCCAGAAA

4301 CGCTGGTGAA AGTAAAAGAT GCTGAAGATC AGTTGGGTGC ACGAGTGGGT

4351 TACATCGAAC TGGATCTCAA CAGCGGTAAG ATCCTTGAGA GTTTTCGCCC

4401 CGAAGAACGT TTTCCAATGA TGAGCACTTT TAAAGTTCTG CTATGTGGCG

4451 CGGTATTATC CCGTATTGAC GCCGGGCAAG AGCAACTCGG TCGCCGCATA

4501 CACTATTCTC AGAATGACTT GGTTGAGTAC TCACCAGTCA CAGAAAAGCA

4551 TCTTACGGAT GGCATGACAG TAAGAGAATT ATGCAGTGCT GCCATAACCA

4601 TGAGTGATAA CACTGCGGCC AACTTACTTC TGACAACGAT CGGAGGACCG

4651 AAGGAGCTAA CCGCTTTTTT GCACAACATG GGGGATCATG TAACTCGCCT

4701 TGATCGTTGG GAACCGGAGC TGAATGAAGC CATACCAAAC GACGAGCGTG

4751 ACACCACGAT GCCTGTAGCA ATGGCAACAA CGTTGCGCAA ACTATTAACT

4801 GGCGAACTAC TTACTCTAGC TTCCCGGCAA CAATTAATAG ACTGGATGGA

4851 GGCGGATAAA GTTGCAGGAC CACTTCTGCG CTCGGCCCTT CCGGCTGGCT

4901 GGTTTATTGC TGATAAATCT GGAGCCGGTG AGCGTGGGTC TCGCGGTATC

4951 ATTGCAGCAC TGGGGCCAGA TGGTAAGCCC TCCCGTATCG TAGTTATCTA

5001 CACGACGGGG AGTCAGGCAA CTATGGATGA ACGAAATAGA CAGATCGCTG

5051 AGATAGGTGC CTCACTGATT AAGCATTGGT AACTGTCAGA CCAAGTTTAC

5101 TCATATATAC TTTAGATTGA TTTAAAACTT CATTTTTAAT TTAAAAGGAT

5151 CTAGGTGAAG ATCCTTTTTG ATAATCTCAT GACCAAAATC CCTTAACGTG

5201 AGTTTTCGTT CCACTGAGCG TCAGACCCCG TAGAAAAGAT CAAAGGATCT

5251 TCTTGAGATC CTTTTTTTCT GCGCGTAATC TGCTGCTTGC AAACAAAAAA

5301 ACCACCGCTA CCAGCGGTGG TTTGTTTGCC GGATCAAGAG CTACCAACTC

5351 TTTTTCCGAA GGTAACTGGC TTCAGCAGAG CGCAGATACC AAATACTGTT

5401 CTTCTAGTGT AGCCGTAGTT AGGCCACCAC TTCAAGAACT CTGTAGCACC

5451 GCCTACATAC CTCGCTCTGC TAATCCTGTT ACCAGTGGCT GCTGCCAGTG

5501 GCGATAAGTC GTGTCTTACC GGGTTGGACT CAAGACGATA GTTACCGGAT

5551 AAGGCGCAGC GGTCGGGCTG AACGGGGGGT TCGTGCACAC AGCCCAGCTT

5601 GGAGCGAACG ACCTACACCG AACTGAGATA CCTACAGCGT GAGCTATGAG

5651 AAAGCGCCAC GCTTCCCGAA GGGAGAAAGG CGGACAGGTA TCCGGTAAGC

5701 GGCAGGGTCG GAACAGGAGA GCGCACGAGG GAGCTTCCAG GGGGAAACGC

5751 CTGGTATCTT TATAGTCCTG TCGGGTTTCG CCACCTCTGA CTTGAGCGTC

5801 GATTTTTGTG ATGCTCGTCA GGGGGGCGGA GCCTATGGAA AAACGCCAGC

5851 AACGCGGCCT TTTTACGGTT CCTGGCCTTT TGCTGGCCTT TTGCTCACAT

5901 GTTCTTTCCT GCGTTATCCC CTGATTCTGT GGATAACCGT ATTACCGCCT

-continued

```
5951 TTGAGTGAGC TGATACCGCT CGCCGCAGCC GAACGACCGA GCGCAGCGAG

6001 TCAGTGAGCG AGGAAGCGGA AGAGCGCCCA ATACGCAAAC CGCCTCTCCC

6051 CGCGCGTTGG CCGATTCATT AATG
```

The viral vector may further comprise a promoter operably linked to the IDUA nucleic acid. In some embodiments, the promoter may be a constitutive promoter, e.g., a CMV promoter. In other embodiments, the promoter may be a tissue-specific or preferred promoter. In some embodiments, the preferred promoter is as cytomegalovirus (CMV) promoter, optionally the preferred promoter is a truncated miniature CMV promoter (mCMV), further optionally the preferred promoter is a 228 bp mCMV having a sequence identical to SEQ ID NO:7. In some embodiments, the nucleic acid is operably linked to a polyadenylation signal, optionally wherein the polyadenylation signal is less than 25 nucleotides in length, optionally wherein the polyadenylation signal is 16 nucleotides in length having a sequence identical to SEQ ID NO:8. In some embodiments, the polyadenylation signal is a sNRP-1 polyadenylation signal. The invention further provides a cell in vitro comprising the AAV vector genome of the invention stably incorporated into the genome of the cell. The invention further provides a recombinant parvovirus particle (e.g., a recombinant AAV particle) comprising the viral vector genome of the invention. Viral vectors and viral particles are discussed further below.

In some embodiments, the recombinant parvovirus template comprises an ITR that is not resolved by Rep to make duplexed AAV vectors as described in international patent publication WO 01/92551.

The parvovirus template and parvovirus rep and cap sequences are provided under conditions such that virus vector comprising the parvovirus template packaged within the parvovirus capsid is produced in the cell. The method can further comprise the step of collecting the virus vector from the cell. The virus vector can be collected from the medium and/or by lysing the cells.

In some embodiments, an AAV particle is provided comprising an AAV vector genome.

The cell can be a cell that is permissive for parvoviral viral replication. Any suitable cell known in the art may be employed. In particular embodiments, the cell is a mammalian cell (e.g., a primate or human cell). As another option, the cell can be a trans-complementing packaging cell line that provide functions deleted from a replication-defective helper virus, e.g., 293 cells or other E1a trans-complementing cells.

The parvovirus replication and capsid sequences may be provided by any method known in the art. Current protocols typically express the parvovirus rep/cap genes on a single plasmid. The parvovirus replication and packaging sequences need not be provided together, although it may be convenient to do so. The parvovirus rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the parvovirus cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski, (1992) *Curr. Top. Microbiol. Immun.* 158:67).

As a further alternative, the rep/cap sequences may be stably incorporated into a cell.

Typically the parvovirus rep/cap sequences will not be flanked by the TRs, to prevent rescue and/or packaging of these sequences.

The parvovirus template can be provided to the cell using any method known in the art. For example, the template can be supplied by a non-viral (e.g., plasmid) or viral vector. In

```
                                                    SEQ ID NO: 7
  1 CGGTTCACTA AACGAGCTCT GCTTATATAG ACCTCCCACC GTACACGCCT

 51 ACCGCCCATT TGCGTCAATG GGGCGGAGTT GTTACGACAT TTTGGAAAGT

101 CCCGTTGATT TTGGTGCCAA AACAAACTCC CATTGACGTC AATGGGGTGG

151 AGACTTGGAA ATCCCCGTGA GTCCGGGGGT CGTTGGGGGG TCAGCCAGGC

201 GGGCCATTTA CCGTAAGTTA TGTAACGA

                                                    SEQ ID NO: 8
  1 AAATAAAATA CGAAAT
```

Methods of Producing Virus Vectors

The present invention further provides methods of producing virus vectors. In one particular embodiment, the present invention provides a method of producing a recombinant parvovirus particle, comprising providing to a cell permissive for parvovirus replication: (a) a recombinant parvovirus template comprising (i) a nucleic acid encoding IDUA, and (ii) a parvovirus ITR; (b) a polynucleotide comprising Rep and Cap coding sequences; under conditions sufficient for the replication and packaging of the recombinant parvovirus template; whereby recombinant parvovirus particles are produced in the cell. Conditions sufficient for the replication and packaging of the recombinant parvovirus template can be, e.g., the presence of AAV sequences sufficient for replication of the parvovirus template and encapsidation into parvovirus capsids (e.g., parvovirus rep sequences and parvovirus cap sequences) and helper sequences from adenovirus and/or herpesvirus. In particular embodiments, the parvovirus template comprises two parvovirus ITR sequences, which are located 5' and 3' to the heterologous nucleic acid sequence, although they need not be directly contiguous thereto.

particular embodiments, the parvovirus template is supplied by a herpesvirus or adenovirus vector (e.g., inserted into the E1a or E3 regions of a deleted adenovirus). As another illustration, Palombo et al., (1998) *J. Virology* 72:5025, describes a baculovirus vector carrying a reporter gene flanked by the AAV TRs. EBV vectors may also be employed to deliver the template, as described above with respect to the rep/cap genes.

In another representative embodiment, the parvovirus template is provided by a replicating rAAV virus. In still other embodiments, an AAV provirus comprising the parvovirus template is stably integrated into the chromosome of the cell.

To enhance virus titers, helper virus functions (e.g., adenovirus or herpesvirus) that promote a productive parvovirus infection can be provided to the cell. Helper virus sequences necessary for parvovirus replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes that promote efficient parvovirus production as described by Ferrari et al., (1997) *Nature Med.* 3:1295, and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into AAV virions, e.g., are not flanked by ITRs.

Those skilled in the art will appreciate that it may be advantageous to provide the parvovirus replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the AAV rep/cap genes.

In one particular embodiment, the parvovirus rep/cap sequences and the adenovirus helper sequences are supplied by a single adenovirus helper vector. This vector can further comprise the parvovirus template. The parvovirus rep/cap sequences and/or the parvovirus template can be inserted into a deleted region (e.g., the E1a or E3 regions) of the adenovirus.

In a further embodiment, the parvovirus rep/cap sequences and the adenovirus helper sequences are supplied by a single adenovirus helper vector. According to this embodiment, the parvovirus template can be provided as a plasmid template.

In another illustrative embodiment, the parvovirus rep/cap sequences and adenovirus helper sequences are provided by a single adenovirus helper vector, and the parvovirus template is integrated into the cell as a provirus. Alternatively, the parvovirus template is provided by an EBV vector that is maintained within the cell as an extrachromosomal element (e.g., as an EBV based nuclear episome).

In a further exemplary embodiment, the parvovirus rep/cap sequences and adenovirus helper sequences are provided by a single adenovirus helper. The parvovirus template can be provided as a separate replicating viral vector. For example, the parvovirus template can be provided by a parvovirus particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The parvovirus rep/cap sequences and, if present, the AAV template are embedded in the adenovirus backbone and are flanked by the 5' and 3' cis sequences, so that these sequences may be packaged into adenovirus capsids. As described above, the adenovirus helper sequences and the parvovirus rep/cap sequences are generally not flanked by ITRs so that these sequences are not packaged into the parvovirus virions.

Zhang et al., ((2001) *Gene Ther.* 18:704-12) describe a chimeric helper comprising both adenovirus and the AAV rep and cap genes.

Herpesvirus may also be used as a helper virus in parvovirus packaging methods. Hybrid herpesviruses encoding the parvovirus Rep protein(s) may advantageously facilitate scalable parvovirus vector production schemes. A hybrid herpes simplex virus type I (HSV-1) vector expressing the AAV-2 rep and cap genes has been described (Conway et al., (1999) *Gene Ther.* 6:986 and WO 00/17377.

As a further alternative, the virus vectors of the invention can be produced in insect cells using baculovirus vectors to deliver the rep/cap genes and parvovirus template as described, for example, by Urabe et al., (2002) *Human Gene Ther.* 13:1935-43.

Parvovirus vector stocks free of contaminating helper virus may be obtained by any method known in the art. For example, parvovirus and helper virus may be readily differentiated based on size. Parvovirus may also be separated away from helper virus based on affinity for a heparin substrate (Zolotukhin et al., (1999) *Gene Therapy* 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of parvovirus. Adenovirus mutants defective for late gene expression are known in the art (e.g., ts100K and ts149 adenovirus mutants).

Recombinant Virus Vectors

The virus vectors of the present invention are useful for the delivery of nucleic acids to cells in vitro, ex vivo, and in vivo. In particular, the virus vectors can be advantageously employed to deliver or transfer nucleic acids to animal, including mammalian, cells. In particular, the virus vectors of the present invention are useful for the delivery of a nucleic acid encoding IDUA to a subject.

It will be understood by those skilled in the art that the nucleic acid encoding IDUA can be operably associated with appropriate control sequences. For example, the nucleic acid can be operably associated with expression control elements, such as transcription/translation control signals, origins of replication, polyadenylation signals, internal ribosome entry sites (IRES), promoters, and/or enhancers, and the like.

Those skilled in the art will appreciate that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In particular embodiments, the promoter/enhancer elements can be native to the target cell or subject to be treated. In representative embodiments, the promoters/enhancer element can be native to the IDUA nucleic acid sequence. The promoter/enhancer element is generally chosen so that it functions in the target cell(s) of interest. Further, in particular embodiments the promoter/enhancer element is a mammalian promoter/enhancer element. The promoter/enhancer element may be constitutive or inducible.

Inducible expression control elements are typically advantageous in those applications in which it is desirable to provide regulation over expression of the nucleic acid sequence. Inducible promoters/enhancer elements for gene delivery can be tissue-specific or -preferred promoter/enhancer elements, and include eye specific or preferred (including retina-specific and cornea-specific) promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In some embodiments, the promoter is 250 base pairs or less in length. In other embodiments, the promoter is a mCMV promoter. In some embodiments, the mCMV promoter is 228 nucleotides in length. In embodiments wherein the nucleic acid sequence is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

In some embodiments, the AAV vector genome is self-complementary.

The virus vectors of the invention can be parvovirus vectors, e.g., AAV vectors. The AAV vectors may be any AAV serotype. In some embodiments, the AAV vector is an AAV2, AAV8, or AAV9 vector. In some embodiments, the AAV vector is a chimeric AAV8/AAV9 particle.

The virus vectors according to the present invention provide a means for delivering IDUA nucleic acids into a broad range of cells, including dividing and non-dividing cells. The virus vectors can be employed to deliver the nucleic acid to a cell in vitro, e.g., to produce IDUA in vitro or for ex vivo gene therapy. The virus vectors are additionally useful in a method of delivering the nucleic acid to a subject in need thereof, e.g., to express IDUA. In this manner, IDUA can be produced in vivo in the subject. The subject can be in need of IDUA because the subject has a deficiency of functional IDUA. Further, the method can be practiced because the production of IDUA in the subject may impart some beneficial effect.

In some embodiments, the AAV vector genome is stably incorporated into the cell genome.

The virus vectors can also be used to produce IDUA in cultured cells or in a subject (e.g., using the subject as a bioreactor to produce the polypeptide or to observe the effects of the polypeptide on the subject, for example, in connection with screening methods).

The virus vectors of the present invention can be employed to deliver a nucleic acid encoding IDUA to treat and/or prevent any disease state for which it is beneficial to deliver IDUA, e.g., MPS I.

Virus vectors according to the instant invention find use in diagnostic and screening methods, whereby the IDUA nucleic acid is transiently or stably expressed in a cell culture system, in an organ or organ culture, or alternatively, a transgenic animal model.

The virus vectors of the present invention can also be used for various non-therapeutic purposes, including but not limited to use in protocols to assess gene targeting, clearance, transcription, translation, etc., as would be apparent to one skilled in the art. The virus vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

Alternatively, the virus vector may be administered to a cell ex vivo and the altered cell is administered to the subject. The virus vector comprising the IDUA nucleic acid is introduced into the cell, and the cell is administered to the subject, where the nucleic acid can be expressed.

Subjects, Pharmaceutical Formulations, and Modes of Administration

Virus vectors according to the present invention find use in both veterinary and medical applications. Suitable subjects include both avians and mammals. The term “avian” as used herein includes, but is not limited to, chickens, ducks, geese, quail, turkeys, pheasant, parrots, parakeets, and the like. The term “mammal” as used herein includes, but is not limited to, humans, non-human primates, bovines, ovines, caprines, equines, felines, canines, lagomorphs, etc. Human subjects include neonates, infants, juveniles, and adults.

In particular embodiments, the present invention provides a pharmaceutical composition comprising a virus vector of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form.

By “pharmaceutically acceptable” it is meant a material that is not toxic or otherwise undesirable, i.e., the material may be administered to a subject without causing any undesirable biological effects.

One aspect of the present invention is a method of transferring a nucleic acid to a cell in vitro. The virus vector may be introduced into the cells at the appropriate multiplicity of infection according to standard transduction methods suitable for the particular target cells. Titers of virus vector to administer can vary, depending upon the target cell type and number, and the particular virus vector, and can be determined by those of skill in the art without undue experimentation. In representative embodiments, at least about $10^3$ infectious units, more preferably at least about $10^5$ infectious units are introduced to the cell.

The cell(s) into which the virus vector is introduced can be of any type. Moreover, the cell can be from any species of origin, as indicated above.

The virus vector can be introduced into cells in vitro for the purpose of administering the modified cell to a subject. In particular embodiments, the cells have been removed from a subject, the virus vector is introduced therein, and the cells are then administered back into the subject. Methods of removing cells from subject for manipulation ex vivo, followed by introduction back into the subject are known in the art (see, e.g., U.S. Pat. No. 5,399,346). Alternatively, the recombinant virus vector can be introduced into cells from a donor subject, into cultured cells, or into cells from any other suitable source, and the cells are administered to a subject in need thereof (i.e., a “recipient” subject).

Suitable cells for ex vivo gene delivery are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ cells or at least about $10^3$ to about $10^6$ cells will be administered per dose in a pharmaceutically acceptable carrier. In particular embodiments, the cells transduced with the virus vector are administered to the subject in a treatment effective or prevention effective amount in combination with a pharmaceutical carrier.

In some embodiments, IDUA is delivered to a cell in vitro or ex vivo by contacting the cell with an effective amount of the AAV particle, thereby delivering IDUA to the cell. In some embodiments, the cells are then transplanted to a subject in need thereof.

A further aspect of the invention is a method of administering the virus vector to subjects. Administration of the virus vectors according to the present invention to a human subject or an animal in need thereof can be by any means known in the art. Optionally, the virus vector is delivered in a treatment effective or prevention effective dose in a pharmaceutically acceptable carrier.

Dosages of the virus vector to be administered to a subject depend upon the mode of administration, the disease or condition to be treated and/or prevented, the individual subject's condition, the particular virus vector, and the nucleic acid to be delivered, and the like, and can be determined in a routine manner. Exemplary doses for achieving therapeutic effects are titers of at least about $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$ transducing units, optionally about $10^8$ to about $10^{15}$ transducing units.

In particular embodiments, more than one administration (e.g., two, three, four or more administrations) may be employed to achieve the desired level of gene expression over a period of various intervals, e.g., daily, weekly, monthly, yearly, etc.

In particular embodiments, a virus vector according to the present invention is administered to the subject to treat, delay the onset of and/or prevent MPS I.

Thus, as one aspect, the invention further encompasses a method of delivering IDUA to a subject, comprising administering to the subject an effective amount of an AAV particle that expresses IDUA, thereby delivering IDUA to the subject.

In another aspect, the invention further encompasses a method of treating, delaying the onset of, and/or preventing MPS I in a subject in need thereof, comprising administering to the subject a therapeutically effective amount of an AAV particle that expresses IDUA, thereby treating or delaying the onset of MPS I in the subject.

In some embodiments, the AAV particle is administered to the subject by injection. In other embodiments, the AAV particle is administered to the subject orally or topically. In the methods of the invention, the subject may be one has been diagnosed with MPS I or is suspected of having MPS I. In certain embodiments, the subject is an infant or child, e.g., less than 18 years old, e.g., less than 18, 17, 16, 15, 14, 13, 12, 11, 10, 9, 8, 7, 6, 5, 4, 3, 2, or 1 years old.

Exemplary modes of administration include oral, rectal, transmucosal, topical, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration), intro-lymphatic, and the like, as well as direct tissue or organ injection (e.g., to liver, skeletal muscle, cardiac muscle, diaphragm muscle or brain). The most suitable route in any given case will depend on the nature and severity of the condition being treated and on the nature of the particular vector that is being used.

In some embodiments, the viral vector is administered directly to the CNS, e.g., the brain or the spinal cord. Any method known in the art to administer vectors directly to the CNS can be used. The vector may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes, cortex, basal ganglia, hippocampus and amygdala), limbic system, neocortex, corpus striatum, cerebrum, and inferior colliculus. The vector may also be administered to different regions of the eye such as the retina, cornea or optic nerve. The vector may be delivered into the cerebrospinal fluid (e.g., by lumbar puncture) for more disperse administration of the vector.

The delivery vector may be administered to the desired region(s) of the CNS by any route known in the art, including but not limited to, intrathecal, intracerebral, intraventricular, intranasal, intra-aural, intra-ocular (e.g., intravitreous, sub-retinal, anterior chamber) and peri-ocular (e.g., sub-Tenon's region) delivery or any combination thereof.

Typically, the viral vector will be administered in a liquid formulation by direct injection (e.g., stereotactic injection) to the desired region or compartment in the CNS. In some embodiments, the vector can be delivered via a reservoir and/or pump. In other embodiments, the vector may be provided by topical application to the desired region or by intra-nasal administration of an aerosol formulation. Administration to the eye or into the ear, may be by topical application of liquid droplets. As a further alternative, the vector may be administered as a solid, slow-release formulation. Controlled release of parvovirus and AAV vectors is described by international patent publication WO 01/91803.

The virus vector can be delivered to skeletal muscle by any suitable method including without limitation intravenous administration, intra-arterial administration, intraperitoneal administration, isolated limb perfusion (of leg and/or arm; see, e.g. Arruda et al., (2005) *Blood* 105:3458-3464), and/or direct intramuscular injection.

Injectables can be prepared in conventional forms, either as liquid solutions or suspensions, solid forms suitable for solution or suspension in liquid prior to injection, or as emulsions. Alternatively, one may administer the virus vector and/or virus capsids of the invention in a local manner, for example, in a depot or sustained-release formulation. Further, the virus vector and/or virus capsid can be delivered adhered to a surgically implantable matrix (e.g., as described in U.S. Patent Publication No. 2004-0013645).

Having described the present invention, the same will be explained in greater detail in the following examples, which are included herein for illustration purposes only, and which are not intended to be limiting to the invention.

Example 1

Construction and Testing of IDUA Vectors

Vector Constructs: Two rAAV vector plasmids were constructed, ptrs-mCMV-hIDUA (SEQ ID NO:6) (FIG. 1, construct a) and ptrs-mCMV-hIDUA$^{op}$ (SEQ ID NO:5) (FIG. 1, construct b), to produce scAAV vectors and enhance the transduction efficiency by codon-optimization such that effective gene therapy products for treating MPS I were developed. These vectors contain a full-length hIDUA cDNA (1962 bp) or a codon-optimized full-length hIDUA cDNA (hIDUA$^{op}$, 1962 bp). A 228 bp truncated miniature CMV promoter (mCMV), and a 16 bp soluble neuropilin-1 (sNRP-1) Poly A signal were used to accommodate the vector genome size limit. These resulted in the 4,850 bp vector genome, which is slightly beyond the ideal size limit for a scAAV vector (~4,700 bp) and, as such, may not generate the desired scAAV vector. In other words, the vector may not package into a self-complementary state. In vitro testing showed that codon-optimization led to improvement in the expression and secretion of rIDUA in cell cultures (FIG. 3).

Figure 1:
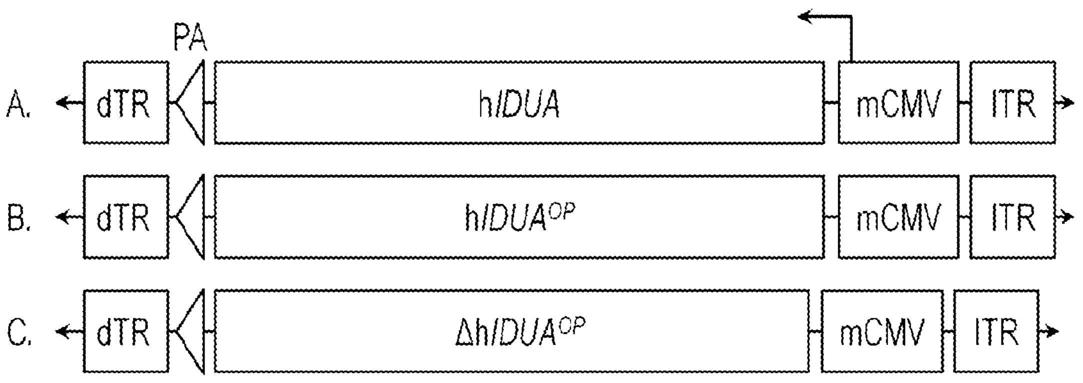
FIG. 1 is a schematic structure of the rAAV9-mCMV-hIDUA viral vector genome. ITR: wt AAV2 terminal repeat.

The hIDUA$^{op}$ cDNA was miniaturized by deleting 15 nucleotides of non-conserved sequence (ΔhIDUA$^{op}$) near the 3'-end and constructed a scAAV vector plasmid, ptrs-mCMV-ΔhIDUA$^{op}$ (SEQ ID NO:4) to further accommodate the vector genome for the generation of scAAV vector expressing hIDUA. The vector genome of this construct was 4,820 bp, containing ITRs, a miniaturized 1,947 bp mIDUA$^{op}$, a mCMV promoter and a sNRP-1 Poly A signal. FIG. 1, construct c illustrates the structure of the scAAV-mCMV-ΔhIDUA$^{op}$ viral vector genome.

Self-Complementary AAV Viral Vector: Three separate plasmid cotransfections were performed in HEK293 cells to produce AAV9-mCMV-hIDUA, AAV9-mCMV-hIDUA$^{op}$ or AAV9-mCMV-ΔhIDUA viral vectors to determine whether the AAV-hIDUA vector constructs would generate scAAV vectors. The purified vector products were analyzed by alkaline denaturing gel electrophoresis. The results showed that the majority (>70%) of the AAV-hIDUA and AAV-hIDUA$^{op}$ viral vector products were ssAAV, likely because their vector genome sizes are beyond the AAV packaging capacity (FIG. 2A). However, the majority of the vector generated from the ptrs-mCMV-ΔhIDUA$^{op}$ were scAAV (FIG. 2B) based on the mobility of the viral genome on the denaturing gel, indicating that miniaturizing hIDUA$^{op}$ by deleting 15 bp from the 3'-end non-coding sequence enabled the vg to be packaged successfully into the scAAV-mCMV-ΔhIDUA$^{op}$ vector.

Codon-optimization and Miniaturization Enhance the Expression and Secretion of rIDUA: A side-by-side comparison of the therapeutic potential of the three AAV-hIDUA vector constructs, independent of vector transduction, was made after in vitro transfection. While all three constructs mediated above normal levels of IDUA activity in both the cell lysates (FIG. 3A) and media (FIG. 3B), ptrs-mCMV-hIDUA$^{op}$ resulted in higher IDUA activity in both cell lysate (FIG. 3A) and media (FIG. 3B), by approximately 25% in total IDUA activity (FIG. 3C), compared to ptrs-mCMV-hIDUA. Surprisingly, the ptrs-mCMV-ΔhIDUA$^{op}$ led to further a significant increase in IDUA activity in both cell lysate (3.1 fold) (FIG. 3A) and in media (11.1 fold) (FIG. 3B), with total 8.0 fold increase (FIG. 3C) over ptrs-mCMV-hIDUA$^{op}$. Importantly, these improvements were from transfected plasmids, all of which enter the cell as dsDNA. The enhanced transduction capability of the scAAV vector is expected to multiply this differential benefit. These data demonstrate that the codon-optimization and especially the miniaturization of hIDUA cDNA significantly enhanced the expression and secretion of the recombinant enzyme, strongly supporting the therapeutic potential of the scAAV9-mCMV-ΔhIDUA gene therapy product for treating MPS I.

scAAV-ΔhIDUA$^{op}$ Gene Delivery Mediates the Correction and Cross-correction of GAG Storage in vitro in MPS I Cells: Human MPS I skin fibroblasts (GM01257) were transfected in duplicate with ptrs-mCMV-ΔhIDUA$^{op}$ plasmid to demonstrate the functionality of the scAAV-mediated recombinant ΔhIDUA (plasmid transfection was used because the AAV9 serotype in which the first batch of scAAV-ΔhIDUA$^{op}$ vector was produced did not effectively transduce fibroblasts). At 48 hours post-transfection, the media from transfected cells were applied to non-treated GM01257 cells for 48 hours incubation. At 48 hours post transfection or media incubation, cell lysates were assayed in duplicate for GAG content. The results showed reduction of GAG content to normal levels in MPS I cells transduced with the vector construct or incubated with the media from ΔhIDUA$^{op}$-transfected GM01257 cells (FIG. 4). The data demonstrated that the AAV-mediated rΔIDUA is fully functional and led to the correction and cross-correction of GAG storage in MPS I cells. The data further supported the therapeutic potential of the proposed scAAV9-mCMV-ΔhIDUA$^{op}$ vector for treating MPS I in humans.

Example 2

Pre-Clinical Studies of rAAV-mCMV-hIDUA Vector without Codon-Optimization

Therapeutic impact of systemic rAAV9-hIDUA gene delivery for treating MPS I in mice: The rAAV9-mCMV-hIDUA vector has been tested in pre-clinical studies in MPS I mice via systemic delivery (Table 2). MPS I mice at age 1 month were treated with an IV injection of rAAV9-mCMV-hIDUA vector at $2\times10^{12}$ vg/kg (n=11) or $5\times10^{12}$ vg/kg (n=17), or at age 6 months with $1\times10^{13}$ vg/kg (n=29). Mice were tested for behavior performance in a hidden task in Morris water maze at age 8 months (n=8-29/group). Necropsies were performed for tissue analyses at 7 days, 1 month, 7 months, or 12 months post vector injection, or humane endpoint. Subsets of mice per cohort were observed for longevity. Controls were non-treated MPS I and wild-type littermates.

TABLE 2

Study design: systemic rAAV9-mCMV-h/DUA gene delivery in MPS I mice

| | | Vector | Number of animals (n) | | | | | | |
|---|---|---|---|---|---|---|---|---|---|
| | | | | | Necropsy | | | | |
| Cohort | AOJ (m) | dose (vg/kg) | Total | Behavior test | 7 d pi | 1 m pi | 7 m pi | End-point | Longevity |
| 1. MPS I | 1 | $2 \times 10^{12}$ | 11 | 11* | — | — | — | 1 | 11 |
| 2. MPS I | 1 | $5 \times 10^{12}$ | 17 | 8* | 2 | 4 | 4 | 1 | 6 |
| 3. MPS I | 6 | $1 \times 10^{13}$ | 29 | 29* | — | — | — | 9 | 29 |

TABLE 2-continued

Study design: systemic rAAV9-mCMV-h/DUA gene delivery in MPS I mice

| | | | | | Number of animals (n) | | | | |
|---|---|---|---|---|---|---|---|---|---|
| | | Vector | | | Necropsy | | | | |
| Cohort | AOJ (m) | dose (vg/kg) | Total | Behavior test | 7 d pi | 1 m pi | 7 m pi | End-point | Longevity |
| 4. MPS I | — | NT | 40 | 21* | — | 3 | 4 | — | 23 |
| 5. WT | — | NT | 27 | 21* | — | 3 | 3 | — | 21 |

AOJ: age of injection;
NT: non-treated;
pi: post vector injection;
*behavior test at age 7 m.

Rapid and Persistent Global Restoration of Functional IDUA Protein in the CNS, PNS and Somatic Tissues: The levels and persistence of transgene expression were assessed. Tissues from the mice in Table 2 were assayed for IDUA activity at 7d pi, 1 m pi, 7 m pi, or humane endpoint. An IV injection of $5\times10^{12}$ vg/kg rAAV9-mCMV-hIDUA vector resulted in rapid and persistent restoration of IDUA activity to supranormal levels in the liver, close to wild-type levels in the heart, sub-normal levels in lung, skeletal muscle, spleen and intestine, and up to 14% of wild-type levels in the brain at all time points (FIG. 5A). There was a decrease over time between 1 month post vector injection, 8 months, and endpoint. At endpoint, IDUA activity was detected at subnormal levels in the majority of the tested tissues and about 5% of wild-type levels in the brain in MPS I mice treated at age 6 months with $1\times10^{13}$ vg/kg of the vector (FIG. 5B). The results also showed low IDUA activity in MPS I mice, who received an IV injection of $2\times10^{12}$ vg/kg rAAV9-mCMV-hIDUA at age 1 month. The mice had IDUA activity <2% of wild-type level in the brain, <25% of wild-type level in the liver and heart, and <5% of wild-type level in 5 other peripheral tissues when assayed at 12 months post vector injection (FIG. 5C). The data demonstrated that the vector treatment led to the quick and persistent restoration of functional IDUA in the CNS and broad peripheral tissues. Importantly, the AAV-mediated IDUA activity persisted to the endpoints in all tissues (FIGS. 5A-5C). The rIDUA expression is dose dependent and $2\times10^{12}$ vg/kg may not mediate sufficient rIDUA expression for functional neurological benefit. Notably, there was no detectable IDUA activity in tissues from non-treated MPS I mice.

Clearance of Lysosomal GAG Storage Pathology and Astrocytosis: Tissues were assayed for GAG contents at different time points post vector injection to further assess the functionality of AAV9-mediated rIDUA. The results showed that an IV injection of $5\times10^{12}$ vg/kg rAAV9-mCMV-hIDUA vector at age 1 month or $1\times10^{13}$ vg/kg at age 6 months resulted in significant reduction of GAG content to normal levels in all vector treated MPS I mice for the brain and the majority of the tested peripheral tissues, except the kidney (FIGS. 6A-6B). The clearance of tissue GAGs was rapid and persisted to the endpoint, correlating to the tissue rIDUA levels in FIGS. 5A-5C. The data demonstrated that the AAV-mediated rIDUA is functional and led to the correction of lysosomal storage pathology at effective doses.

Figure 7A:
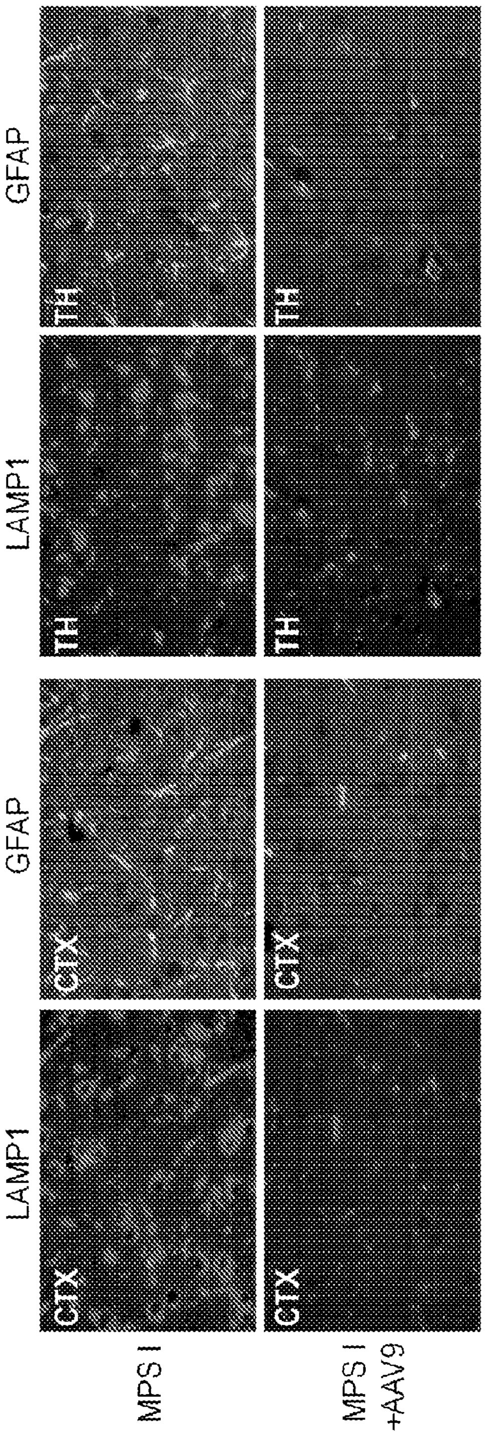
Figure 7B:
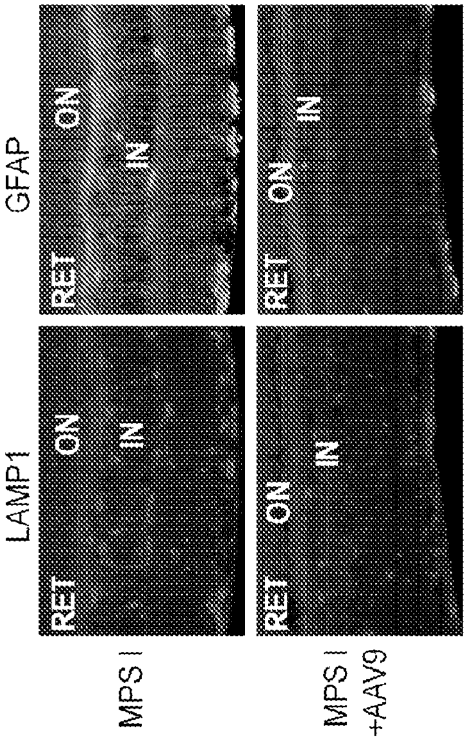
Figure 7C:
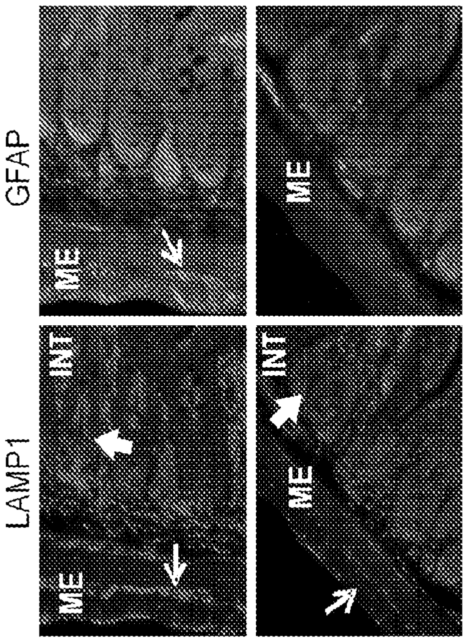
Figure 7D:
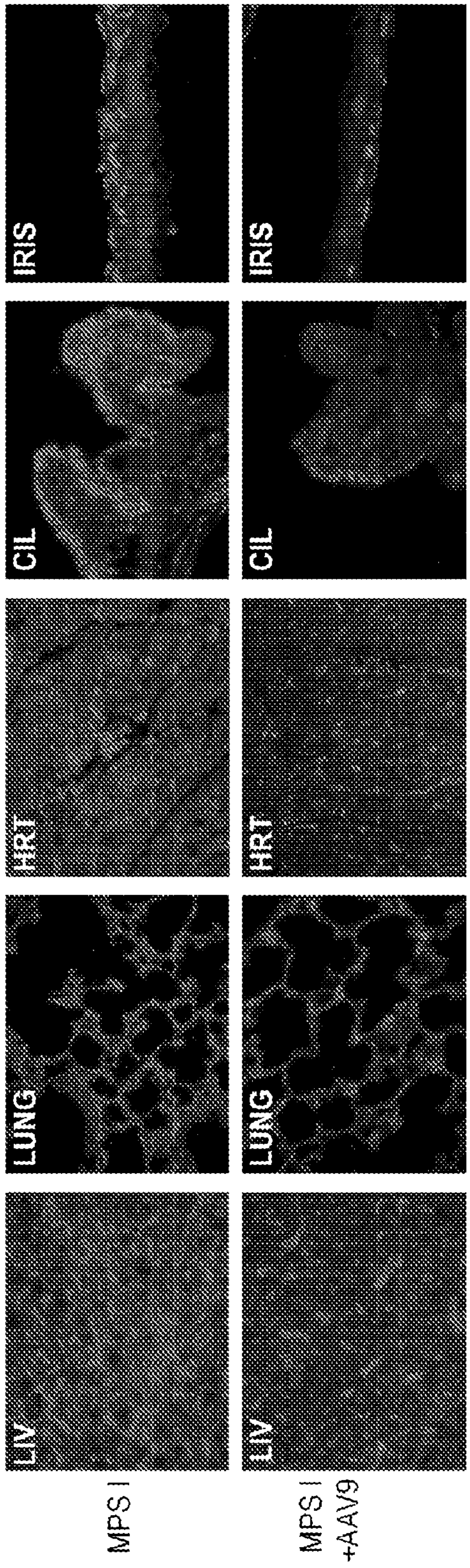

Further, immunofluorescence (IF) staining showed clearance of the LAMP1 lysosomal marker throughout the brain (FIG. 7A), intestinal nerves (FIG. 7B) and eye (FIG. 7C), and the majority of the tested somatic tissues (FIG. 7D). The data further supported that rAAV9-mediated rIDUA is functional and led to rapid and complete clearance of GAG storage in the CNS, peripheral nervous system (PNS) and optical nervous system (ONS), as well as broad peripheral tissues. IF staining also showed the clearance of GFAP-positive signals in the brain, intestine and retina (FIGS. 7A-7C), indicating amelioration of astrocytosis and neuroinflammation in the CNS, PNS and ONS.

Functional Benefits: Correction of Behavior Deficits and Extension of Survival: Vector-treated MPS I mice and controls were tested for cognitive ability and motor function in a hidden task in the Morris water maze at 8 months to assess the functional impacts of systemic rAAV9-hIDUA gene delivery. The results showed normalized latency to find a hidden platform (FIG. 8A) and swimming ability (FIG. 8B) in MPS I mice that received an IV injection of $5\times10^{12}$ vg/kg rAAV9-mCMV-hIDUA at age 1 month, indicating the correction of cognitive and motor functions. However, MPS I mice treated at age 1 month with the vector at $2\times10^{12}$ vg/kg did not show detectable improvement in either the latency to the target (FIG. 8A) or the swimming speed (FIG. 8B), indicating that $2\times10^{12}$ vg/kg is below the minimal effective dose. Furthermore, improved, though not normalized, swimming ability (FIG. 8B) and latency to the find the hidden platform (FIG. 8A) was observed in MPS I mice that were treated at age 6 months with $1\times10^{13}$ vg/kg vector. When the test results were analyzed for the 8 months cohort, only 2 months post vector injection (FIGS. 8A-8B), it was hypothesized that the full scale of functional benefits may require more time when treated at very advance disease stages. Notably, the majority of non-treated MPS I mice >8 months of age are not testable in water maze due to disease severity. The data demonstrated that a single IV injection of rAAV9-mCMV-hIDUA at an effective dose does not only prevent but may also reverse the cognitive and motor function deficits to a certain extent in MPS I mice.

A subset of each cohort was observed for longevity to further assess the functional benefits of the vector treatments. Significant extension of survival was observed in MPS I mice treated at age 1 month with $5\times10^{12}$ vg/kg rAAV9-mCMV-hIDUA or at age 6 months with $1\times10^{13}$ vg/kg vector compared to non-treated MPS I mice ($p<0.05$) (FIG. 8C). Notably, the majority of these vector treated MPS I mice survived to within the normal lifespan range (FIG. 8C). Given that neurological manifestation is one of the major causes of premature death in MPS I, the significantly extended survival of treated MPS I mice further supports the functional therapeutic benefits of systemic rAAV9-mCMV-hIDUA gene delivery for treating MPS I.

However, vector treatment at $2\times10^{12}$ vg/kg did not show significant impact on the survival of MPS I mice, further supporting that vector treatment at $2\times10^{12}$ vg/kg is below the minimal effective dose, because it did not mediate sufficient rIDUA expression for the functional correction of MPS I.

Differential Biodistribution of rAAV9-mCMV-hIDUA Vector Genome: Total DNA isolated from tissues was assayed by qPCR to determine the biodistribution of the systemically delivered rAAV9-mCMV-hIDUA and to quantify scAAV9-hIDUA vector genome copy numbers in tissues at different time points post vector injection (n≥4/group). The results showed differential biodistribution of the vector DNA among different tissues with the highest concentration detected in the liver, followed by heart, skeletal muscle, lung, intestine, kidney, spleen, and brain (FIGS. 9A-9H). Copies of the vector genome persisted in tissues, though decreased in some tissues over time between age 2 months and 8 months.

In Summary: Three gene replacement therapy vectors for treating MPS I, rAAV-mCMV-hIDUA, rAAV-mCMV-hIDUA$^{op}$, and scAAV-mCMV-ΔhIDUA$^{op}$, were developed. The data demonstrated that codon-optimization enhanced both the expression and secretion of rIDUA. Importantly, the deletion of 15 bp from the 3'-end non-conserved sequence enabled the packaging of scAAV vector, scAAV-mCMV-ΔhIDUA$^{op}$, which led to a further 11-fold improvement in rIDUA expression and secretion. Administration of the vector, rAAV-mCMV-hIDUA, was tested in MPS I mice. The preclinical study results reinforced the view that systemic delivery of the trans-BBB-neurotropic AAV9 gene therapy vector can prevent and reverse the global neuropathy and broad somatic manifestations of the disease. The minimal effective dose of rAAV-mCMV-hIDUA was determined to be $5\times10^{12}$ vg/kg. It is believed that scAAV-mCMV-ΔhIDUA$^{op}$ will offer much greater therapeutic benefits, given the demonstrated higher transduction efficiency of scAAV vector, over the single-stranded rAAV-mCMV-hIDUA vector. Moreover, it is believed that much less scAAV-mCMV-ΔhIDUA$^{op}$ vector will be needed for maximal efficacy, which will reduce the challenge in scale-up manufacture and potential toxicity.

Example 3

Pre-Clinical Studies of scAAV-mCMV-ΔhIDUA$^{op}$ Vector in MPS I Mouse Model Preclinical studies were initiated to test the therapeutic potential of systemic delivery of scAAV9-mCMV-ΔhIDUA$^{op}$ vector for treating MPS IIIC in mice. MPS I mice were treated at age 1 month with an IV injection of scAAV9-mCMV-ΔhIDUA$^{op}$ vector at $2\times10^{12}$ vg/kg (n=12), $5\times10^{12}$ vg/kg (n=20), or $1\times10^{13}$ vg/kg (n=16). For tissue analyses, necropsies were performed at 1 month post injection (pi) (n=4), and will be performed at 7 months pi (n=4) and humane endpoint. Mice will be tested for behavior performance in a hidden task in Morris water maze at age 8 months (n≥8/group). Subsets of mice per cohort will be observed for longevity. Controls were non-treated MPS I and wt littermates. The following are the results obtained so far.

Rapid restoration of functional IDUA protein in the CNS and peripheral tissues: To assess the levels and persistence of transgene expression, tissues were assayed for IDUA activity at 1 month pi. An IV injection of $2\times10^{12}$ vg/kg scAAV9-mCMV-ΔhIDUA$^{op}$ vector resulted in rapid restoration of IDUA activity to normal or close to normal levels in the liver, heart, kidney, lung, intestine and supranormal levels in brain and muscle, and sub-normal levels in spleen (FIG. 1*a*). The vector treatment at $5\times10^{12}$ vg/kg led to the restoration of IDUA activity to supranomal levels in the liver, to or close to normal levels in the brain, heart, kidney, lung, intestine, spleen and muscle (FIG. 10A). Notably, there was no detectable IDUA activity in tissues from non-treated MPS II mice. These data demonstrate that an IV scAAV9-mCMV-ΔhIDUA$^{op}$ vector delivery mediated efficient expression of functional rIDUA protein leading to the quick restoration of IDUA activity in the CNS and broad peripheral tissues.

Clearance of GAG contents in the CNS and peripheral tissues: Tissues were also assayed for GAG contents at 1 month pi, to further assess the functionality of AAV9-mediated rIDUA. The results showed significant reduction of GAG contents in MPS I mice that an IV injection of scAAV9-mCMV-ΔhIDUA$^{op}$ at both $2\times10^{12}$ vg/kg and $5\times10^{12}$ vg/kg resulted in significant reduction of GAG content to normal levels in the brain and the majority of the tested peripheral tissues, including liver, heart, kidney and spleen, in all vector treated MPS I mice (FIG. 10B). The GAG reduction was seen to be inconsistent in lung, intestine and muscle, due to the individual variation (FIG. 10B). These data further demonstrate that the AAV-mediated rIDUA is functional, leading to the quick tissue GAG clearance, supporting the correction of lysosomal storage pathology in the CNS and peripheral organs.

Differential biodistribution of rAAV9-mCMV-hIDUA vector genome: Total DNA isolated from tissues was assayed by qPCR to quantify scAAV9-hIDUA vector genome copy numbers in tissues at different time points post vector injection (n=4/group), to determine the biodistribution of the systemically delivered rAAV9-mCMV-hIDUA. The results showed differential biodistribution of the vector DNA among different tissues, with the highest concentration detected in the liver, followed by spleen, heart, lung, intestine, kidney, skeletal muscle, and brain (FIG. 11). The tissue vector copy levels were largely dose-responsive in the majority of tested tissues, including brain, liver, heart, spleen, and lung (FIG. 11).

In summary, preclinical studies demonstrate that the scAAV-mCMV-ΔhIDUA$^{op}$ vector via an IV injection mediated the efficient expression of functional rIDUA protein, leading to the correction of lysosomal storage pathology in an MPS I mouse model. These can be achieved at a dose as low as $2\times10^{12}$ vg/kg, strongly supporting the therapeutic potential of scAAV-mCMV-ΔhIDUA$^{op}$ for treating MPS I via a systemic delivery.

All publications, patents, and patent applications are herein incorporated by reference to the same extent as if each individual publication, patent, or patent application was specifically and individually indicated to be incorporated by reference.

Although the foregoing invention has been described in some detail by way of illustration and example for purposes of clarity of understanding, it will be obvious that certain changes and modifications may be practiced within the scope of the list of the foregoing embodiments and the appended claims.

That which is claimed is:

1. A recombinant nucleic acid comprising a nucleotide sequence encoding human alpha-L-iduronidase (IDUA), wherein the nucleotide sequence has been codon-optimized for expression in human cells and wherein the nucleotide sequence is at least 90% identical to SEQ ID NO: 1.

2. The recombinant nucleic acid of claim 1, wherein the nucleotide sequence has been truncated by removing 15 nucleotides of the non-coding sequence from near the 3' end and wherein the nucleotide sequence is at least 90% identical to SEQ ID NO:3.

3. The recombinant nucleic acid of claim 2 comprising the nucleotide sequence of SEQ ID NO:3.

4. The recombinant nucleic acid of claim 1 comprising the nucleotide sequence of SEQ ID NO:1.

5. An adeno-associated virus (AAV) vector genome comprising the nucleic acid of claim 1.

6. The AAV vector genome of claim 5, wherein the nucleic acid is operably linked to a promoter, optionally wherein the promoter is 250 base pairs or less in length.

7. The AAV vector genome of claim 6, wherein the promoter is a mCMV promoter, optionally wherein the mCMV promoter sequence is identical to SEQ ID NO: 7.

8. The AAV vector genome of claim 5, wherein the nucleic acid is operably linked to a polyadenylation signal, optionally wherein the polyadenylation signal is less than 25 base pairs in length.

9. The AAV vector genome of claim 8, wherein the polyadenylation signal is a sNRP-1 polyadenylation signal, optionally wherein the sNRP-1 polyadenylation signal is identical to SEQ ID NO:8.

10. The AAV vector genome of claim 5, wherein the AAV vector genome is self-complementary.

11. A cell in vitro comprising the AAV vector genome of claim 5.

12. An AAV particle comprising the AAV vector genome of claim 5.

13. The AAV particle of claim 12, wherein the AAV particle is an AAV2, AAV8, AAV9, or chimeric AAV8/AAV9 particle.

14. A pharmaceutical formulation comprising the AAV particle of claim 12 in a pharmaceutically acceptable carrier.

15. A method of delivering IDUA to a subject, comprising administering to the subject an effective amount of the AAV particle of claim 12, thereby delivering IDUA to the subject.

16. A method of treating or delaying the onset of mucopolysaccharidosis I (MPS I) in a subject in need thereof, comprising administering to the subject a therapeutically effective amount of the AAV particle of claim 12, thereby treating or delaying the onset of MPS I in the subject.

17. A method of delivering IDUA to a cell in vitro or ex vivo, comprising contacting the cell with an effective amount of the AAV particle of claim 12, thereby delivering IDUA to the cell.

18. The method of claim 17, further comprising transplanting the cell to a subject in need thereof.

19. A recombinant nucleic acid comprising a nucleotide sequence encoding human alpha-L-iduronidase (IDUA), wherein the nucleotide sequence has been truncated by removing 15 nucleotides of the non-coding sequence from near the 3' end and wherein the nucleotide sequence comprises the nucleotide sequence of SEQ ID NO:2.

* * * * *